US009834804B2

(12) United States Patent
Dufresne et al.

(10) Patent No.: US 9,834,804 B2
(45) Date of Patent: Dec. 5, 2017

(54) FUNGAL CELLS AND FERMENTATION PROCESSES

(71) Applicant: Iogen Energy Corporation, Ottawa (CA)

(72) Inventors: Philippe J. Dufresne, Baie-d'Urfé (CA); Adam H. Colville, Ottawa (CA); Barbara Fryzuk, Nepean (CA); Loreta Gudynaite-Savitch, Kanata (CA); Christopher M. D. Hindle, Gloucester (CA); Boguslaw Ploch, Ottawa (CA); John J. Tomashek, Ottawa (CA)

(73) Assignee: Iogen Energy Corporation, Ottawa (CA)

(*) Notice: Subject to any disclaimer, the term of this patent is extended or adjusted under 35 U.S.C. 154(b) by 130 days.

(21) Appl. No.: 14/353,916

(22) PCT Filed: Dec. 12, 2012

(86) PCT No.: PCT/CA2012/050891
§ 371 (c)(1),
(2) Date: Apr. 24, 2014

(87) PCT Pub. No.: WO2013/086633
PCT Pub. Date: Jun. 20, 2013

(65) Prior Publication Data
US 2014/0295504 A1    Oct. 2, 2014

Related U.S. Application Data

(60) Provisional application No. 61/570,545, filed on Dec. 14, 2011.

(51) Int. Cl.
| | |
|---|---|
| C12N 1/14 | (2006.01) |
| C12N 9/24 | (2006.01) |
| C12P 19/14 | (2006.01) |
| C07K 14/37 | (2006.01) |
| C07K 14/38 | (2006.01) |
| C12P 19/00 | (2006.01) |
| C12N 9/14 | (2006.01) |
| C12N 9/42 | (2006.01) |
| C12P 19/02 | (2006.01) |

(52) U.S. Cl.
CPC .............. *C12P 19/14* (2013.01); *C07K 14/37* (2013.01); *C07K 14/38* (2013.01); *C12N 1/14* (2013.01); *C12N 9/14* (2013.01); *C12N 9/24* (2013.01); *C12N 9/2437* (2013.01); *C12P 19/00* (2013.01); *C12P 19/02* (2013.01)

(58) Field of Classification Search
None
See application file for complete search history.

(56) References Cited

U.S. PATENT DOCUMENTS

| 6,015,703 A | 1/2000 | White et al. |
| 2004/0121446 A1 | 6/2004 | England et al. |

OTHER PUBLICATIONS

GenBank Accession No. EFQ32984 (Nov. 2010).*
GenBank Accession No. EGR46093 (Jul. 2011).*
H.V. Colot et al. "A high-throughput gene knockout procedure for Neurospora reveals functions for multiple transcription factors", PNAS 103(27):10352-10357 (Jul. 2006).*
FGSC #19486, http://www.fgsc.net/scripts/StrainSearchReturnPage.asp?OrgID=22246, retrieved Jun. 3, 2016.*
GenBank Accession XP_956246 (Apr. 2008).*
B. Seiboth et al. Trichoderma reesei: A Fungal Enzyme Producer for Cellulosic Biofuels, Biofuel Production-Recent Developments and Prospects, Dr. Marco Aurelio Dos Santos Bernardes (Ed.), ISBN: 978-953-307-478-8, InTech pp. 309-340. (Sep. 2011).*
Ahamed et al., "Effect of culture medium composition on Trichoderma reesei's mophology and cellulase production", Bioresource Technology, vol. 100 (2009) 5979-87.
Aro et al., "ACEII, a Novel Transcriptional Activator Involved in Regulation of Cellulase and Xylanase Genes of Trichoderma reesei", J. Biological Chemistry, vol. 276 (2001) 24309-14.
Aro et al., "ACEI of Trichoderma reesei is a Repressor of Cellulase and Xylanase Expression", Appl. Environmental Microbiology, vol. 69, No. 1 (2003) 56-65.
Bailey et al., "Induction, isolation, and testing of stable Trichoderma reesei mutants with improved production of solubilizing cellulase", Enzyme Microb. Technol., vol. 3 (1981) 153-57.
Durand et al, "Genetic improvement of Trichoderma reesei for large scale cellulase production", Enzyme Microb. Technol., vol. 10 (1988) 341-46.
Eveleigh et al., "Increasing Yields of Extracellular Enzymes", Adv. Appl. Mlcrobiol., vol. 25 (1979) 57-74.
Foreman et al., "Transcriptional Regulation of Biomass-degrading Enzymes in the Filamentous Fungus *Trichoderma reesei*", J. Biol. Chem., vol. 278 (2003) 31988-97.
Ilmén et al., "The glucose repressor gene cre1 of Trichoderma: Isolation and expression of a full-length and a truncated mutant form", Mol. Gen. Genet., vol. 251 (1996) 451-60.
Ilmén et al., "Regulation of cellulase gene expression in the filamentous fungus *Trichoderma reesei*", Appl. Environ. Microbiol., vol. 63, No. 4 (1997) 1298-1306.
Kruszewska, et al., "Overexpression of the *Saccharomyces cerevisiae* Mannosylphosphodolichol Synthase-Encoding Gene in Trichoderma reesei Results in an Increased Level of Protein Secretion and Abnormal Cell Ultrastructure", Appl. Environ. Microbiol., vol. 65, No. 6 (1999) 2382-87.
Kruszewska, et al., "Alterations in protein secretion caused by metabolic engineering of glycosylation pathways in fungi", Acta Biochima Polonica, vol. 55, No. 3 (2008) 447-56.

(Continued)

*Primary Examiner* — Rebecca Prouty
(74) *Attorney, Agent, or Firm* — Fitzpatrick, Cella, Harper & Scinto

(57) ABSTRACT

The present invention provides an isolated fungal cell that is capable of producing one or more biomass-degrading enzymes and that exhibits increased or decreased expression or copy number of a polynucleotide encoding a PtaB-like protein. Also provided is a fermentation processes for producing one or more biomass-degrading enzymes comprising a fungal cells exhibiting increased or decreased expression or copy number of a polynucleotide encoding a PtaB-like protein. The biomass-degrading enzymes produced by the isolate fungal cell and fermentation processes of the present invention may be used in a process to produce soluble sugars from biomass.

11 Claims, 13 Drawing Sheets

(56) References Cited

OTHER PUBLICATIONS

Kubicek et al., "Triggering of Cellulase Biosynthesis by Cellulose in Trichoderma reesei", J. Biol. Chem., vol. 268, No. 26 (1993) 19364-68.
Kubicek et al., "Metabolic engineering strategies for the improvement of cellulase production by Hypocrea jecorina", Biotechnol. Biofuels., vol. 2, No. 19 (2009) 1-14.
Le Crom et al., "Tracking the roots of cellulase hyperproduction by the fungus *Trichoderma reesei* using massively parallel DNA sequencing", PNAS, vol. 106, No. 38 (2009) 16151-56.
Lockington et al., "Regulation by carbon and nitrogen sources of a family of cellulases in Aspergillus nidulans", Fungal Genet. Biol., vol. 37 (2002) 190-96.
Mach et al., "Regulation of gene expression in industrial fungi: *Trichoderma*", Appl. Microbiol. Biotechnol., vol. 60 (2003) 515-22.
Mandels et al., "Problems and Challenges in the Cellulose to Cellulase Fermentation", Process Biochemistry, vol. 13, No. 5 (1978) 6-11.
Mandels et al., "Sophorose as an Inducer of Cellulase in Trichoderma viride", J. Bacteriol., vol. 83, No. 2 (1962) 400-8.
Mandels, et al., "Enhanced Cellulase Production by a Mutant of Trichoderma viride", Appl. Mlcriobiol., vol. 21, No. 1 (1971) 152-54.
Nakari-Setälä et al., "Genetic Modification of Carbon Catabolite Repression in Trichoderma reesei for Improved Production", Appl. Environ. Microbiol., vol. 75, No. 14 (2009) 4853-60.
Nevalainen et al., "Production of Extracellular Enzymes in Mutants Isolated from Trichoderma viride Unable to Hydrolyze Cellulose", Appl. Environ. Microbiol., vol. 35, No. 1 (1978) 11-16.
Pakula et al., "The effect of specific growth rate on protein synthesis and secretion in the filamentous fungus *Trichoderma reesei*", Microbiology, vol. 151 (2005) 135-43.
Portnoy et al., "Differential Regulation of the Cellulase Transcription Factors XYR1, ACE2, and ACE1 in Trichoderma reesei Strains Producing High and Low Levels of Cellulase", Eukaryotic Cell, vol. 10, No. 1 (2011) 262-71.
Royer et al., "Interrelationship of Xylanase Induction and Cellulase Induction of Trichoderma longibrachiatum", Appl. Environ. Microbiol., vol. 56, No. 8 (1990) 2535-39.
Saloheimo et al., "The protein disulfide isomerase gene of the fungus *Trichoderma reesei* is induced by endoplasmic reticulum stress and regulated by the carbon source", Mol. Genet. Genomics, vol. 262 (1999) 35-45.
Saloheimo et al, "Activation mechanisms of the HACI-mediated unfolded protein response in filamentous fungi", Mol. Microbiol., vol. 47, No. 4 (2003) 1149-61.
Saloheimo et al, "Characterization of secretory genes ypt1/yptA and nsf1/nsfA from Two filamentous Fungi: Induction of Secretory Pathway Genes of Trichoderma reesei under Secretion Stress Conditions", Appl. Environ. Microbiol., vol. 70, No. 1 (2004) 459-67.
Seidl et al., "The Hypocrea jecorina (Trichoderma reesei) hypercellulolytic mutant RUT C30 lacks a 85 kb (29 gene-encoding) region of the wild-type genome", BMC Genomics, vol. 9, Article 327 (2008) 1-15.
Sternberg et al., "Induction of Cellulolytic Enzymes in Trichoderma reesei by Sophorose", J. Bacteriol., vol. 139, No. 3 (1979) 761-69.
Steyaert et al., "Isolate-specific condition in Trichoderma in response to different nitrogen sources", Fungal Biology, vol. 114 (2010) 179-88.
Steyaert et al., "Reproducion without sex: conidiation in the filamentous fungus *Trichoderma*", Microbiology, vol. 156 (2010) 2887-900.
Stricker et al., "Xyr1 (Xylanase Regulator 1) Regulates both the Hydrolytic Enzyme System and D-Xylose Metabolism in Hypocrea jecorina", Eukaryotic Cell, vol. 5, No. 12 (2006) 2128-37.
Stricker et al., "Xyr1 receives the lactose induction signal and regulates lactose metabolism in Hypocrea jecorina", FEBS Letters, vol. 581 (2007) 3915-20.
Stricker et al., "Regulation of transcription of cellulases- and hemicellulases-encoding genes in Aspergillus niger and Hypocrea jecorina (Trichoderma reesei)", Appl. Microbiol. Biotechnol. vol. 78 (2008) 211-20.
Torigoi et al., "Mutants of Trichoderma reesei are defective in cellulose induction, but not basal expression of cellulase-encoding genes", Gene vol. 173 (1996) 199-203.
Valkonen et al, "The ire1 and ptc2 genes involved in the unfolded protein response pathway in the filamentous fungus *Trichoderma reesei*", Mol. Genet. Genomics, vol. 272 (2004) 443-51.
Vitikainen et al., "Array comparative genomics hybridization analysis of Trichoderma reesei strains with enhanced cellulase production properties", BMC Genomics vol. 11, Article 441 (2010) 1-16.
Zeilinger et al., "Differential Inducibility of Expression of the Two Xylanase Genes xyn1 and xyn2 in Trichoderma reesei", J. Biol. Chem., vol. 271 (1996) 25624-29.
Zeilinger et al., "The Hypocrea jecorina HAP 2/3/5 protein complex binds to the inverted CCAAT-box (ATTGG) within the cbh2 (cellobiohydrolase II-gene) activating element", Mol. Genet. Genom., vol. 266 (2001) 56-63.
B.N. Chakaborty, et al., "Transformation of filamentous fungi by electroporation", Nucleic Acids Research, vol. 18, No. 22, p. 6737 (1990).
H. Conlon, et al., "The Aspergillus nidulans GATA transcription factor gene areB encodes at least three proteins and features three classes of mutation", Molecular Microbiology, 40(2), pp. 361-375 (2001).
G.H. Goldman, et al., "Transformation of Trichoderma harzianum by high-voltage electric pulse", Curr. Genet. 17, pp. 169-174 (1990).
B.W. Hazell, et al, "Rapid transformation of high cellulase-producing mutant strains of Trichoderma reesei by microprojectile bombardment", Letters in Applied Microbiology, 30, pp. 282-286 (2000).
M.G. Steiger, et al., "Transformation System for Hypocrea jecorina (Trichoderma reesei) That Favors Homologous Integration and Employs Reusable Bidirectionally Selectable Markers", Applied and Environmental Microbiology, vol. 77, No. 1, pp. 114-121 (2011).
P.L. Suominen, et al., "High frequency one-step gene replacement in Trichoferma reesei. II.Effects of deletions of Individual cellulase genes", Mol. Gen. Genet. 241, pp. 523-530 (1993).
J.C. Dunlap, et al., "Enabling a Community to Dissect an Organism: Overview of the Neurospora Functional Genomic Project," Adv. Genet., 57, pp. 49-96 (2007).
M.L. Nielsen, et al., "A genome-wide polyketide synthase deletion library uncovers novel genetic links to polyketides and meroterpenoids in Aspergillus nidulans," FEMS Microbial. Lett., 321, pp. 157-166 (2011).
A. Schuster, et al., "A versatile toolkit for high throughput functional genomics with Trichoderma reesei," Biotechnology for Biofuels, 5:1, pp. 1-10 (2012).
J.S. Tolan and B. Foody, "Cellulase from Submerged Fermentation," Advances in Biochemical Engineering/Biotechnology, 65, pp. 42-67 (1999).

* cited by examiner

|  | T. rees | N. hea | F. oxy | G. gra | C. mil | V. dahl | T. terr | V. albo | N. cras | Ch. ther | M. oryz | B. fuck | S. ther |
|---|---|---|---|---|---|---|---|---|---|---|---|---|---|
| T. rees |  | 61.6 | 62.3 | 55.0 | 35.2 | 49.0 | 40.1 | 43.4 | 38.0 | 34.8 | 39.6 | 34.6 | 40.3 |
| N. hea | 61.6 |  | 85.9 | 62.0 | 38.5 | 55.1 | 40.5 | 43.5 | 42.8 | 40.0 | 43.8 | 39.7 | 39.6 |
| F. oxy | 62.3 | 85.9 |  | 60.7 | 37.9 | 52.0 | 45.9 | 42.9 | 40.4 | 40.2 | 38.9 | 35.4 | 41.7 |
| G. gra | 55.0 | 62.0 | 60.7 |  | 36.8 | 74.4 | 49.3 | 57.0 | 48.6 | 35.8 | 44.4 | 43.9 | 53.1 |
| C. mil | 35.2 | 38.5 | 37.9 | 36.8 |  | 35.6 | 27.9 | 27.5 | 26.1 | 26.1 | 28.9 | 26.0 | 31.8 |
| V. dahl | 49.0 | 55.1 | 52.0 | 74.4 | 35.6 |  | 50.0 | 69.7 | 45.3 | 35.0 | 45.6 | 43.9 | 50.6 |
| T. terr | 40.1 | 40.5 | 45.9 | 49.3 | 27.9 | 50.0 |  | 42.0 | 48.5 | 53.6 | 42.4 | 35.4 | 63.4 |
| V. albo | 43.4 | 43.5 | 42.9 | 57.0 | 27.5 | 69.7 | 42.0 |  | 36.7 | 23.7 | 35.8 | 31.8 | 41.0 |
| N. cras | 38.0 | 42.8 | 40.4 | 48.6 | 26.1 | 45.3 | 48.5 | 36.7 |  | 43.0 | 45.4 | 34.2 | 44.8 |
| Ch. ther | 34.8 | 40.4 | 40.2 | 35.8 | 26.1 | 35.0 | 53.6 | 23.7 | 43.0 |  | 16.3 | 29.3 | 47.6 |
| M. oryz | 39.6 | 43.8 | 38.9 | 44.4 | 28.9 | 45.6 | 42.4 | 35.8 | 45.4 | 16.3 |  | 36.0 | 47.6 |
| B. fuck | 34.6 | 39.7 | 35.4 | 43.9 | 26.0 | 43.9 | 35.4 | 31.8 | 34.2 | 29.3 | 36.0 |  | 33.4 |
| S. ther | 40.3 | 39.6 | 41.7 | 53.1 | 31.8 | 50.6 | 63.4 | 41.0 | 44.8 | 47.6 | 47.6 | 33.4 |  |

Figure 11

FUNGAL CELLS AND FERMENTATION PROCESSES

RELATED APPLICATIONS

This application is a national phase of PCT/CA2012/050891 filed Dec. 12, 2012 which in turn claims the benefit of priority from U.S. Provisional Patent Application No. 61/570,545 filed Dec. 14, 2011, the content of which is hereby incorporated by reference herein in its entirety.

FIELD OF THE INVENTION

The present invention relates to fungal cells and fermentation processes for the production of biomass-degrading enzymes.

BACKGROUND OF THE INVENTION

Filamentous fungi are used for the production of enzymes and proteins for a variety of industrial biotechnology applications. Of the fungi used for enzyme production, strains of *Trichoderma reesei* (the asexual anamorph of *Hypocrea jecorina*) are particularly prominent due to their ability to secret large amounts (>50 g/L) of useful enzymes in industrial fermentations. Different high-productivity (and "hyperproductive") *Trichoderma* strain lineages have been developed by different groups, almost all originating from QM6a, the "wild-type" environmental strain (Bailey and Nevalainen, 1981, *Enzyme Microb. Technol.* 3: 153; Vitikainen et al., 2010, *BMC Genomics* 11: 441, and references therein). Reported examples of high-productivity strains include QM9414 (Mandels and Andreotti, 1978, *Process Biochemistry* 13: 6), Rut-C30 (Eveleigh and Montenecourt, 1979, *Adv. Appl. Microbiol.* 25: 57), CL847 (Durand et al., 1988, *Enzyme Microb. Technol.* 10: 341) and M2C38 (U.S. Pat. No. 6,015,703). High-productivity strains are used to express both enzymes endogenous to the organism as well as heterologously expressed and secreted proteins. Such enzymes and proteins include cellulases, hemicellulases, amylases, proteases, laccases and esterases—all of which have been expressed for commercial purposes. Efforts continue to identify factors that regulate protein productivity so that further improvements can be made (Le Crom et al., 2009, *P.N.A.S. USA* 106: 16151).

High productivity is dependent upon multiple factors. Depending upon the particular strain, the carbon source and feed rate will determine which genes for secreted enzymes are induced and/or repressed, as well as the growth and enzyme production rates observed. The carbon source acts through transcription factors and their cognate promoters that are either activated or repressed under certain feed conditions. Expression of proteins is typically driven by promoters for the major cellulases and hemicellulases (e.g., Cel6A, Cel7A, Xyn11B) or hybrids thereof, e.g., a hybrid of the Cel7A and Xyn11B promoter regions and secretion signals (U.S. Pat. No. 6,015,703). The transcription factors that regulate these promoters have been partially identified and characterized. Once transcribed and translation is initiated, secretion depends upon the particular signal sequence and the secretion apparatus of the cell, both of which have been manipulated to improve productivity. All steps from carbon source through secretion can be manipulated to improve productivity by identifying and altering the regulatory proteins and networks that control the cascade of functions.

Cellulase and hemicellulase expression can be controlled, in part, by the choice of carbon source (Ilmén et al., 1997, *Appl. Environ. Microbiol.* 63: 1298; Mach and Zeilinger, 2003, *Appl. Microbiol. Biotechnol.* 60: 515; Schmoll and Kubicek, 2003, *Acta Microbiologica et Immunologica Hungarica* 50: 125; Ahamed and Vermette, 2009, *Bioresources Technology* 100: 5979). Typically, cellulose and beta-linked gluco-oligosaccharides (e.g., cellobiose, sophorose, gentiobiose, laminaribiose, lactose) induce expression of cellulases and their accessory enzymes (Mandels et al., 1962, *J. Bacteriology* 83: 400; Sternberg and Mandels, 1979, *J. Bacteriology* 139:761; Foreman et al., 2003, *J. Biol. Chem.* 278: 31988). Similarly, xylan, xylose and xylo-oligosaccharides will induce hemicellulases and their accessory enzymes (Royer and Nakas, 1990, *Appl. Environ. Microbiol.* 56: 2535; Zeilinger et al., 1996, *J. Biol. Chem.* 271: 25624). Glucose represses (hemi)cellulase expression in cells with a functioning cre1 gene (Ilmen et al., 1996, *Mol. Gen. Genet.* 251: 451). Nitrogen has well documented effects on cellular reproduction and morphology (Steyaert et al., 2010a, *Fungal Biology* 114: 179; 2010b, Microbiology 156: 2887), which in turn effects large scale production results (Ahamed and Vermette, 2009, *Bioresources Technology* 100: 5979). Nitrogen may also play a role in cellulase production. For example, it has been reported that cellulase production is elevated in an *A. niger* strain containing a constitutively activated nitrogen regulator AreA, while cellulase production is reduced in an AreA loss-of-function mutant grown in cellulose-induced cultures using ammonium as a nitrogen source (Lockinton et al., 2002, Fungal Genet. Biol. 37: 190).

Several major transcription factors have been identified that interact with the promoter regions of cellulase and hemicellulase genes and regulate their expression (Mach and Zeilinger, 2003, *Appl. Microbiol. Biotechnol.* 60: 515; Schmoll and Kubicek, 2003, *Acta Microbiologica et Immunologica Hungarica* 50:1 25; Kubicek et al., 2009, *Biotechnology for Biofuels* 2:19 and references therein). Cre1 (catabolite repression) mediates carbon catabolite repression and blocks cellulase expression when the cells are grown on glucose and other non-inducing carbohydrates (Ilmen et al., 1996, *Mol. Gen. Genet.* 251: 451). The gene for Cre1 is often defective or deleted in high-productivity strains (Seidl et al., 2008, *BMC Genomics* 9:327; Nakari-Setälä et al., 2009, *Appl. Environ. Microbiol.* 75: 4853). However, recent data suggest that Cre1 may also have a role in upregulation by other factors involved in cellulase and hemicellulase expression (Portnoy et al., 2011, *Eukaryotic Cell* 10: 262). Xyr1 (xylanase regulator) is an essential transcriptional activator that promotes expression of cellulases and hemicellulases (Stricker et al., 2006, *Eukaryotic Cell* 5: 2128; Stricker et al., 2007, *FEBS Letters* 581: 3915; Stricker et al., 2008, *Appl. Microbiol. Biotechnol.* 78: 211). Ace1 (activator of cellulase expression) has been identified as a repressor of cellulases and xylanases (Aro et al., 2003, *Appl. Environ. Microbiol.* 69: 56). Ace2, in contrast, appears to be an activator of cellulase expression under certain conditions (Aro et al., 2001, *J. Biol. Chem.* 276: 24309). The Hap complex (heme activator protein, named after homologous proteins originally identified in *Saccharomyces cerevisiae*) has been shown to interact with regulatory regions in cellulase promoters that are necessary for expression (Zeilinger et al., 2001, *Mol. Genet. Genom.* 266:56). Strains of *Trichoderma* have been isolated that cannot be induced to produce cellulases at more than basal levels, presumably due to defects in one or more of these global regulators of cellulase expression (Nevalainen and Palva, 1978, *Appl. Environ. Microbiol.* 35: 11; Torigoi et al., 1996, Gene 173: 199).

While feed choice and the transcription factors associated with induction and repression will determine the levels of particular mRNAs transcribed, the feed rate and secretory capacity of a particular strain will determine how much carbon in the feed goes to secreted protein versus diversion into biomass, and how much and how long protein can be secreted from the cell before feedback signals cause secretion rates to diminish. Increasing feed rate will increase protein productivity up to a point past which productivity will decrease precipitously and feed will go primarily to making biomass (Pakula et al., 2005, *Microbiology* 151: 135). Strains fermented under conditions leading to high productivity may be limited by the capacity of the secretory pathway. Fungal cells respond naturally by increasing expression of secretory pathway components (Saloheimo et al., 1999, *Mol. Gen. Genet.* 262: 35; 2004, *Appl. Environ. Microbiol.* 70: 459). Improvement of secretion can be achieved by intentionally over-expressing genes involved in the secretory pathway (Kruszewska et al., 1999, *Appl. Environ. Microbiol.* 65: 2382; 2008, *Acta Biochimica Polonica* 55:447). Ultimately, secretion stress can result in misfolding of proteins in the secretory pathway which will activate the unfolded protein response (UPR) and in turn down-regulate the expression of secreted proteins (Saloheimo et al., 2003, *Molecular Microbiology* 47: 1149; Valkonen et al., 2004, *Mol. Genet. Genom.* 272:443). An additional response in *Trichoderma*—repression under secretion stress (RESS)—further down-regulates expression of secreted proteins (Pakula et al., 2003, *Mol. Genet. Genom.* 272:443).

*Trichoderma* isolates resulting from mutagenesis that are unable to produce cellulases have been reported in the literature. Torigoi et al. (1996) have previously characterized four cellulase deficient *Trichoderma* mutants (QM9136, QM9977, QM9978 and QM9979) obtained by UV irradiation of QM6a (Mandels et al., 1971). All of the described mutants fail produce detectable cel5A, cel6A, cel7A and cel7B transcripts when induced with sophorose or cellulose. Failure to produce cellulase in one of these mutants (QM9979) was linked to its inability to uptake cellulase di-saccharide inducer, and postulated through functional analysis to carry a defective/mutated β-glycoside permease (Kubicek et al., 1993). Still, identity of the specific gene involved and nature of mutation involved was not described The present invention is based on the identification of a gene encoding a polypeptide involved in moderating the development of a heritable cellulase deficient phenotype that arises after prolonged fermentation of filamentous fungi. The identified gene also regulates the ability of the fungi to tolerate aggressive fermentation conditions that enable high productivity. Disclosed herein is a means for modifying or tailoring fungal cells to meet the specific requirements of different enzyme production conditions by decreasing or increasing the expression of the gene.

SUMMARY OF THE INVENTION

The present invention relates to fungal cells and fermentation processes for the production of biomass-degrading enzymes.

In a first aspect, the present invention provides an isolated fungal cell capable of producing one or more biomass-degrading enzyme and comprising an increase in copy number or expression of a polynucleotide encoding a polypeptide exhibiting from about 40% to 100% identity to SEQ ID NO: 1 or from about 50% to about 100% identity to the amino acid sequence of SEQ ID NO: 3, SEQ ID NO: 4, SEQ ID NO: 5, SEQ ID NO: 7, SEQ ID NO: 9, SEQ ID NO: 11, or SEQ ID NO: 14, relative to a parental fungal cell from which the isolated fungal cell is derived.

In one embodiment, the fungal cell comprises an increase in copy number or expression, relative to a parental fungal cell from which the isolated fungal cell is derived, of a polynucleotide that hybridizes under at least high stringency conditions to any one of (i) the polypeptide coding sequence of SEQ ID NO: 2, (ii) a genomic DNA sequence comprising the polypeptide coding sequence of SEQ ID NO: 2, and (iii) a full-length complementary strand of (i) or ii), wherein high stringency conditions are prehybridization and hybridization at 42° C. for 12 to 24 hours in 5×SSPE, 0.3% SDS, 200 ng/mL sheared and denatured salmon sperm DNA, and 50% formamide followed by post-hybridization washes of three times each for 15 minutes using 2×SSC, 0.2% SDS at 65° C.

In another embodiment, the fungal cell is a species of *Trichoderma*, *Hypocrea*, *Aspergillus*, *Fusarium*, *Penicillium*, *Neurospora*, *Chaetomium*, *Acremonium*, *Glomerella*, *Myceliophthora*, *Sporotrichum*, *Thielavia*, *Chrysosporium*, *Corynascus*, *Ctenomyces*, *Verticillium*, *Cordyceps*, *Nectria*, or *Magnaporthe*. For example, the fungal cell may be *T. reesei*, *H. jecorina*, *A. niger*, *A. fumigatus*, *A. oryzae*, *A. nidulans*, *F. oxysporum*, *N. crassa*, *C. thermophilum*, *A. thermophilum*, *G. graminicola*, *M. thermophila*, *S. thermophile*, *T. terrestris*, *T. heterothallica*, *C. thermophile*, *V. dahlia*, *C. militaris*, *N. heamatococca*, or *M. oryzae*.

In another aspect, the present invention provides a fermentation process for the production of one or more biomass-degrading enzyme comprising providing the isolated fungal cell as described above, culturing the isolated fungal cell in a submerged liquid fed-batch or continuous culture; and providing the fed-batch or continuous culture with a feed solution comprising a carbon source. Such fermentation process results in a population of fungal cells with a 50% reduction in cel-phenotype relative to an equivalent process utilizing a parental fungal cell.

In one embodiment, the fermentation process as described above is characterized by at least a 50% increase in sustained productivity relative to an equivalent process utilizing a parental fungal cell from which the isolated fungal cell is derived In a third aspect, the present invention relates to an isolated fungal cell capable of producing one or more biomass-degrading enzyme, comprising a decrease in copy number or expression, relative to a parental fungal cell from which the isolated fungal cell is derived, of a polynucleotide encoding a polypeptide exhibiting from about 40% to 100% identity to SEQ ID NO: 1 or from about 50% to about 100% identity to the amino acid sequence of SEQ ID NO: 3, SEQ ID NO: 4, SEQ ID NO: 5, SEQ ID NO: 7, SEQ ID NO: 9, SEQ ID NO: 11, or SEQ ID NO: 14.

In one embodiment, the fungal cell comprises a decrease in copy number or expression, relative to a parental fungal cell from which the isolated fungal cell is derived, of a polynucleotide that hybridizes under at least high stringency conditions to any one of (i) the polypeptide coding sequence of SEQ ID NO: 2, (ii) a genomic DNA sequence comprising the polypeptide coding sequence of SEQ ID NO: 2, and (iii) a full-length complementary strand of (i) or (ii), wherein high stringency conditions are prehybridization and hybridization at 42° C. for 12 to 24 hours in 5×SSPE, 0.3% SDS, 200 µg/mL sheared and denatured salmon sperm DNA, and 50% formamide followed by post-hybridization washes of three times each for 15 minutes using 2×SSC, 0.2% SDS at 65° C.

In another embodiment, the fungal cell is a species of *Trichoderma*, *Hypocrea*, *Aspergillus*, *Fusarium*, *Penicil-*

*lium, Neurospora, Chaetomium, Acremonium, Glomerella, Myceliophthora, Sporotrichum, Thielavia, Chrysosporium, Corynascus, Ctenomyces, Verticillium, Cordyceps, Nectria,* or *Magnaporthe*. For example, the fungal cell may be *T. reesei, H. jecorina, A. niger, A. fumigatus, A. oryzae, A. nidulans, F. oxysporum, N. crassa, C. thermophilum, A. thermophilum, G. graminicola, M. thermophila, S. thermophile, T. terrestris, T. heterothallica, C. thermophile, V. dahlia, C. militaris, N. heamatococca,* or *M. orzyae*.

In a fourth aspect, the present invention provides a fermentation process for the production of one or more biomass-degrading enzyme comprising: providing the isolated fungal cell of the third aspect; culturing the isolated fungal cell in a submerged liquid fed-batch or continuous culture; and providing the fed-batch or continuous culture with a feed solution comprising a carbon source. Such fermentation process exhibits at least about a 50% increase in maximal specific productivity ($q_p$) relative to an equivalent process utilizing a parental fungal cell. In one embodiment of this fermentation process, the feed solution is provided at a carbon addition rate is at least 0.4 grams carbon per liter per hour. In another embodiment, the feed solution is provided at a carbon addition rate is at least 0.8 grams carbon per liter per hour.

In yet another embodiment of either of the fermentation processes described above, the carbon source in the feed solution provided during the step of culturing consists of one or more cellulase-inducing carbohydrate (such as cellulose, lactose, cellobiose, sophorose, gentiobiose, and a combination thereof), one or more hemicellulose-derived carbohydrate (such as xylan, arabinoxylan, xylo-oligosaccharides, arabinoxylo-oligosaccharides, D-xylose, xylobiose, L-arabinose, D-mannose D-galactose and combinations thereof), one or more non-inducing carbohydrate (such as glucose, dextrose, sucrose, molasses, fructose, and any combination thereof); a mixture of cellulase-inducing and hemicellulose-derived carbohydrates, a mixture of cellulase-inducing and non-inducing carbohydrate, a mixture of hemicellulose-derived and non-inducing, carbohydrates, or a mixture of cellulase-inducing, hemicellulose-derived, and non-inducing carbohydrates.

The isolated fungal cells and fermentation processes of the present invention produce one or more biomass-degrading enzymes. In some embodiments, the one or more biomass-degrading enzyme is selected from the group consisting of a cellulase, a cellobiohydrolase, an endoglucanase, a beta-glucosidase, a cellulase-enhancing protein, a xylanase, a beta-xylosidase, an alpha-arabinofuranosidase, a beta-mannanase, an alpha-glucuronidase, an acetyl xylan esterase, a ferulic acid esterase, a lignin-degrading enzyme, and any combinations thereof.

In some embodiments, at least one of the one or more biomass-degrading enzymes is endogenous to the fungal cell. In other embodiments, at least one of the one or more biomass-degrading enzymes is heterologous to the fungal cell.

In a final aspect, the present invention provides a process for treating a biomass substrate with the biomass-degrading enzyme(s) produced by the fermentation processes or isolated fungal cells as describe hereinabove. In some embodiments, the biomass substrate is a lignocellulosic feedstock.

Specific productivity (dotted lines and closed triangles) was measured as mg of protein produced per g of fungal cells per hour.

Figure 8:
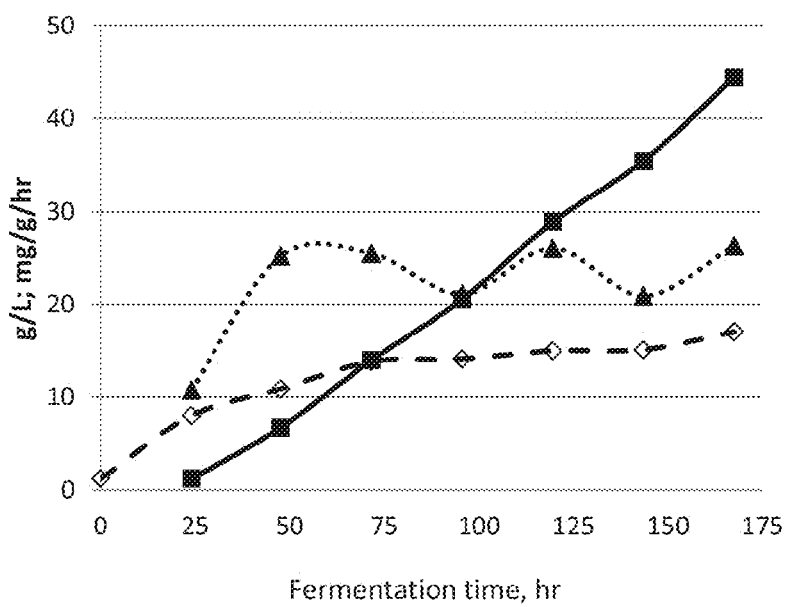
Figure 8:
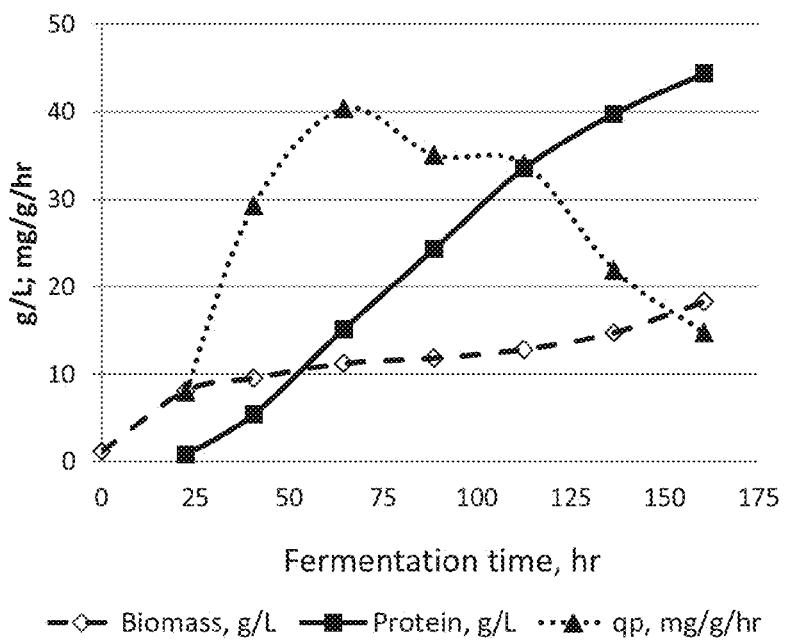

FIG. 8 shows pilot fermentation profiles of a PtaB overexpression strain (A) and its parental strain (B). Fed-batch fermentations were performed as described in Example 5 at a carbon addition rate of ~0.4 g of carbon per liter per h using a mixture of cellulase-inducing and hemicellulose-derived carbohydrates. Accumulation of biomass (dotted lines, open diamonds) and total protein (solid lines, closed circles) were measured every 24 h after fermentation start. Specific productivity (dotted lines and closed triangles) was measured as mg of protein produced per g of fungal cells per hour.

Figure 9:
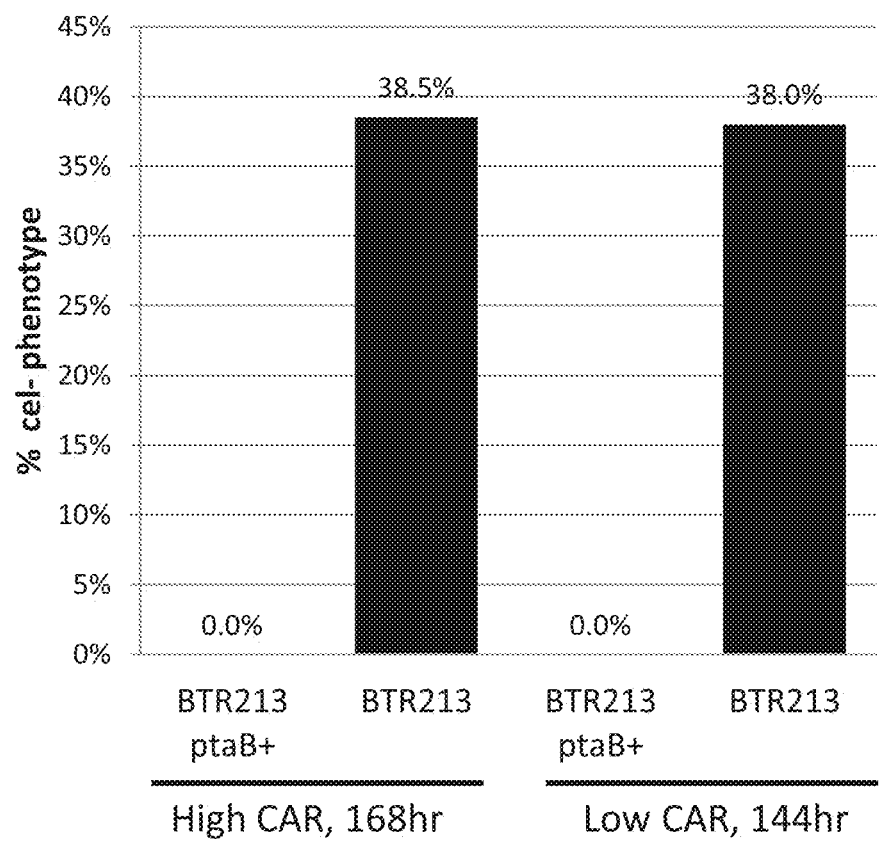

FIG. 9 shows the accumulation of cellulase non-producing (cel-) phenotype at the end of fed-batch fermentations of PtaB-overexpressing strain and its parental strain. Biomass samples were collected after 168 h and 144 h from fermentation start for High and low CAR fermentations, respectively. Cellulase production phenotype was assessed as described in Example 6.

Figures 1, 10:
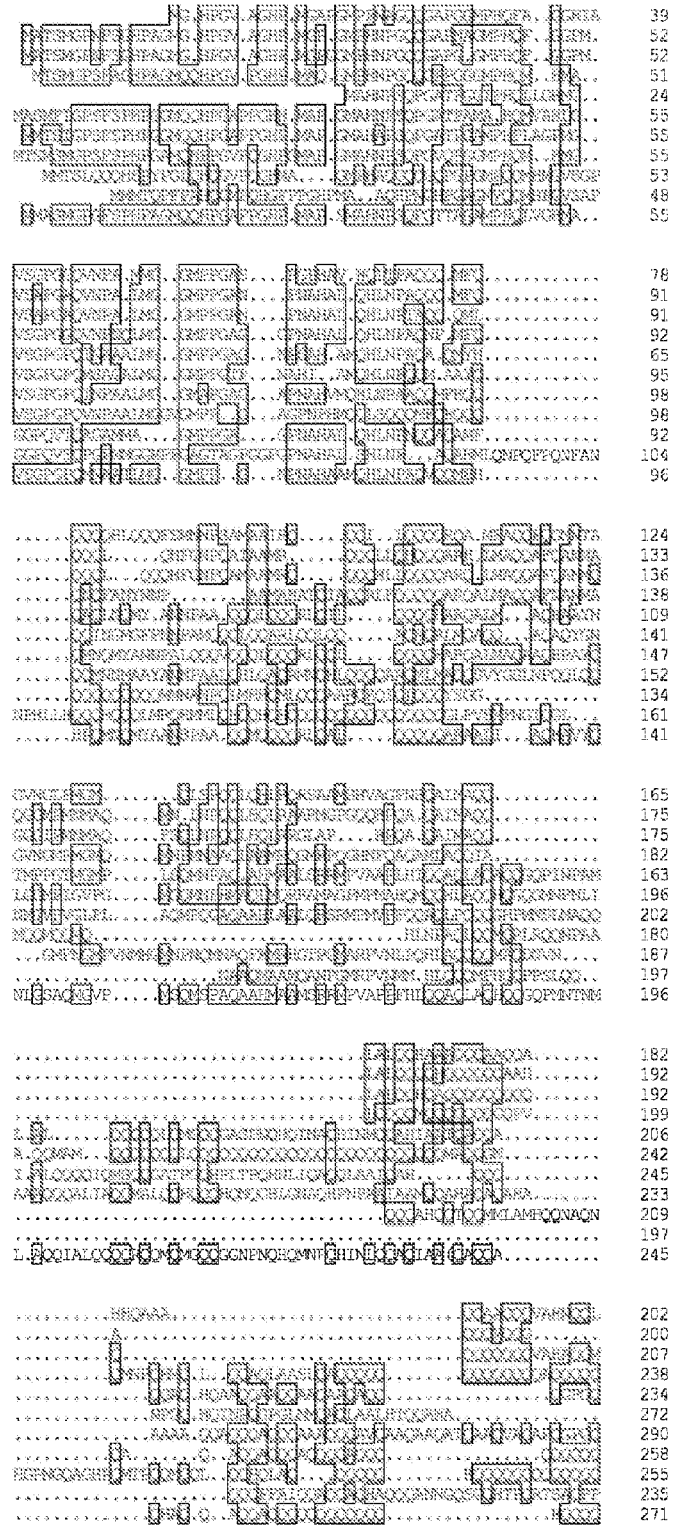

FIG. 10 shows an alignment of SEQ ID NO: 1 with homologous amino acid sequences from other fungal species. Overall identity is 42.77%. Identical amino acids are shown in boxes, and a consensus sequence is shown under alignment. Alignment was made using DNAman program, gap penalty 3, K-tuple 2.

FIG. 11 shows an identity matrix for the amino acid sequences of thirteen fungal PtaB-like proteins to each other.

DETAILED DESCRIPTION OF THE INVENTION

The present invention relates to fungal cells and fermentation processes for the production of biomass-degrading enzymes.

More specifically, the present invention relates to isolated fungal cells that exhibit enhanced or decreased expression or activity of the polypeptide encoded by SEQ ID NO: 1 and fermentation processes utilizing the isolated fungal cells for the production of one or more biomass-degrading enzyme.

The following description is of a preferred embodiment by way of example only and without limitation to the combination of features necessary for carrying the invention into effect. The headings provided are not meant to be limiting of the various embodiments of the invention. Terms such as "comprises", "comprising", "comprise", "includes", "including" and "include" are not meant to be limiting. In addition, the use of the singular includes the plural, and "or" means "and/or" unless otherwise stated. Numeric ranges are inclusive of the numbers defining the range.

Unless otherwise defined herein, the practice of the present invention involves conventional techniques commonly used in molecular biology, fermentation, microbiology, and related fields, which are known to those of skill in the art. Although any methods and materials similar or equivalent to those described herein can be used in the practice or testing of the present invention, some suitable methods and materials are described. Unless otherwise defined herein, all technical and scientific terms used herein have the same meaning as commonly understood by one of ordinary skill in the art. Unless otherwise indicated, nucleic acids are written left to right in 5' to 3' orientation; amino acid sequences are written left to right in amino to carboxy orientation, respectively.

All patents and publications, including all sequences disclosed within such patents and publications, referred to herein are expressly incorporated by reference.

Isolated Fungal Cells

As used herein, an "isolated fungal cell" is a fungal cell that has been modified so as to exhibit either increased or decreased expression or copy number of a polynucleotide encoding PtaB-like protein, or increased or decreased expression of a PtaB-like protein, relative to a parental fungal cell from which it is derived.

As used herein, a "parental fungal cell" is a fungal cell which has not been modified so to exhibit either increased or decreased expression or copy number of a polynucleotide encoding PtaB-like protein, or increased or decreased expression of a PtaB-like protein. A parental fungal cell may be a "wild-type" or "native" fungal cell as found in nature without any mutations or genetic modifications or it may be a fungal cell comprising one or more genetic modifications, including but not limited to a recombinant fungal cell. For example, the parental fungal cell may comprise one or more mutation that allow for enhanced production of biomass degrading enzymes under inducing conditions or in the presence of a repressing carbohydrates such as glucose (including, for example, mutations in the cre gene) or under secretion stress (including, for example, mutations in the hac1 or ire1 genes).

The parental fungal cell may also be modified for enhanced or reduced production of one or more biomass-degrading enzymes or for reduced production of proteases. Therefore, "a parental fungal cell from which the isolated fungal cell is derived" is essentially identical to the isolated fungal cell except for the increased or decreased expression or copy number of a polynucleotide encoding PtaB-like protein, or increased or decreased expression of a PtaB-like protein"

As used herein, "a recombinant fungal cell" is a fungal cell into which one or more polynucleotides have been introduced by deliberate human intervention or "recombinant means."

As used herein, a "genetic modification" or "mutation" includes, but is not limited to, (a) heritable changes to the sequence or structure of the fungal cell's genomic DNA resulting, for example, from random mutagenesis and selection, adaptation, or epigenetic changes and (b) genetic modification to introduce polynucleotide sequences into the fungal cell using recombinant means.

For the purposes described herein, the term "increased copy number" means at least one extra copy of at least the polypeptide coding sequence of a given gene is present in the isolated fungal cell as compared to the number of copies of the same gene in a parental fungal cell from which the isolated fungal cell is derived. For example, the isolated fungal cell may contain 1, 2, 3, 4, 5, 10, or more extra copies of at least the polypeptide coding sequence of a given gene relative to the number of copies of that same gene in the parental fungal cell. The extra copies of a given gene may be integrated into the genome of the isolated fungal cell or may be present on one or more autonomously replicating vectors or plasmids present in the isolated fungal cell.

For the purposes described herein, the term "decreased copy number" means at least one less copy of at least the polypeptide coding sequence of a given gene is present in the genome of the isolated fungal cell as compared to the copy number of the same gene present in a parental fungal cell from which the isolated fungal cell is derived.

The modulation of copy numbers of genes can be measured by one of ordinary skill in the art through well-known means, for example, comparative genomic hybridization (CGH), Southern blot hybridization, or quantitative real-time PCR (qRT-PCR) from genomic DNA.

For the purposes described herein, the term "increased expression" or "overexpression" means at least about a 1.2-fold increase in the level of transcript or polypeptide encoded by a given gene, or in the activity of the resulting polypeptide, in the isolated fungal cell as compared to that exhibited by the parental fungal cell, when grown under identical or nearly identical conditions of medium composition, temperature, pH, cell density and age of culture. For example, the level of transcript or polypeptide encoded by a given gene, or in the activity of the resulting polypeptide, in the isolated fungal cell can be increased by at least 1.3-, 1.5-, 2.0-, 2.5-, 3.0-, 4.0-, 5.0-, or 10-fold, or more, as compared to that exhibited by the parental fungal cell when grown or cultured under identical or nearly identical culture conditions.

For the purposes described herein, the term "decreased expression" means at least about a 20% decrease in the level of transcript or polypeptide encoded by a given gene, or in the activity of the resulting polypeptide, in the isolated fungal cell as compared to that exhibited by the parental fungal cell when grown under identical or nearly identical conditions of medium composition, temperature, pH, cell density and age of culture. For example, the level of transcript or polypeptide encoded by a given gene, or of the activity of the resulting polypeptide, in the isolated fungal cell may be decreased by 20%, 30%, 40%, 50%, 60%, 70%, 80%, 90%, 100%, or any amount therebetween, as compared to that exhibited by the parental fungal cell when grown or cultured under essentially the same culture conditions.

The modulation of expression of genes also can be measured by one of ordinary skill in the art through analysis of selected mRNA or transcript levels by well-known means, for example, quantitative real-time PCR (qRT-PCR), Northern blot hybridization, or global gene expression profiling using cDNA or oligo array hybridization.

Increased production of a polypeptide production of a given gene can be measured, for example, with immunochemical methods such as ELISA (Van Weemen, B. K. et al. (1971) *FEBS Letters* 15: 232-236) with antibodies specific to the individual enzyme or by assays that specifically detect and measure the activity of the polypeptide In at least some embodiments of the present invention, the increase or decrease in copy number or expression of a gene encoding a PtaB-like protein in the isolated fungal cell can be produced by any of various random mutagenesis and selection techniques. For example, the parental fungal cell may be subjected to irradiation or chemical mutagenesis to create a library of mutated cells, which are then screened for the desired altered phenotype or genotype. Random mutagenesis and selection techniques also include "adaptive evolution techniques" or "evolutionary engineering techniques". As used herein, the term adaptive evolution technique refers to any method or procedure employed to influence the phenotype and genetic profile of a fungal cell or organism through the use of exposure to environmental challenges, and subsequent selection of the modified and/or isolated fungal cell with the desired altered phenotype and corresponding altered genetic profile.

As used herein, "random mutagenesis and selection" refers to the process of creating by natural or artificial means, including subjecting the fungal cell to irradiation or chemical mutagenesis, a library of mutated strains, which are then screened for a desired altered phenotype. Adaptation, also referred to as "adaptive evolution" or "evolutionary engineering", refers to any method or procedure employed to influence the phenotype and genetic profile of a fungal cell through the use of exposure to environmental challenges, and subsequent selection of a modified fungal cell with the desired altered phenotype. "Epigenetic changes" are defined as heritable changes in chromatin structure that alter the expression of one or more genes in an organism, including but not limited to, histone methylation, histone acetylation, ubiquitination, phosphorylation or sumoylation, and DNA methylation.

In at least some embodiments of the present invention, the increase or decrease in copy number or expression of a gene encoding a PtaB-like protein in the isolated fungal cell can be produced by any one of various genetic engineering techniques or recombinant means. As used herein, a "genetic engineering technique" refers to any of several well-known techniques for the direct manipulation of an organism's genes or genome. For example, gene knockout (insertion of an inoperative DNA sequence, often replacing or interrupting the endogenous operative sequence, into an organism's chromosome), gene knock-in (insertion of a protein-coding DNA sequence into an organism's chromosome), and gene knockdown (insertion of DNA sequences that encode antisense RNA or small interfering RNA, i.e., RNA interference (RNAi)) techniques are well known in the art.

Methods for decreasing or reducing gene expression are well known and can be performed using any of a variety of methods known in the art. For example, the gene can be modified to disrupt a transcription or translation initiation sequence or to introduce a frameshift mutation in the transcript encoding the polypeptide. Other methods of reducing the gene expression include post-transcriptional RNA silencing methodologies such as antisense RNA and RNA interference (RNAi). Antisense techniques involve introducing a nucleotide sequence complementary to the transcript of a target gene such that the complementary antisense nucleotide sequence hybridizes to the target gene transcript, thus reducing or eliminating the number of transcripts available to be translated into protein. Examples of expressing an antisense RNA are shown in Ngiam et al. (2000) *Appl. Environ. Microbiol.* 66(2):775-82; and Zrenner et al. (1993) *Planta.* 190(2):247-52. RNAi methodologies include double stranded RNA (dsRNA), short hairpin RNAs (shRNAs), and small interfering RNAs (siRNAs) as known to one of skill in the art, for example, the techniques of Fire et al. (1998) *Nature* 391:806-11; Paddison et al. (2002) *Genes Dev.* 16:948-58; and Miyagishi et al. (2002) *Nat. Biotechnol.* 20:497-500.

Methods for decreasing or reducing the expression of a gene also include partial or complete deletion of the gene, and disruption or replacement of the promoter of the gene such that transcription of the gene is greatly reduced or even inhibited. For example, the promoter of the gene can be replaced with a weak promoter, as exemplified by U.S. Pat. No. 6,933,133. Thus, where the weak promoter is operably linked with the coding sequence of an endogenous polypeptide, transcription of that gene will be greatly reduced or even inhibited.

In some embodiments, the isolated fungal cell has been genetically modified to at least partially delete one or more gene encoding a PtaB-like protein. As used herein, a gene deletion or deletion mutation is a mutation in one or more nucleotides making up the gene is missing. Thus, a deletion is a loss or replacement of genetic material resulting in a complete or partial disruption of the sequence of the DNA making up the gene. Any number of nucleotides can be deleted, from a single base to an entire piece of a chromosome. In some embodiments, complete or near-complete deletion of the gene sequence is contemplated. For example, deletion in a gene may be a deletion of at least 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% of the gene.

In some embodiments, the isolated fungal cell is genetically modified to increase expression of a PtaB-like protein. The PtaB-like protein may be homologous or heterologous with respect to the fungal cell. For the purposes herein, an homologous PtaB-like protein is encoded by a polynucleotide sequence that naturally occurs in, or is isolated or derived from, the same or taxonomically equivalent taxonomic species as the fungal cell. Furthermore, as is recognized by one of skill in the art, a homologous protein may contain one or more insertions, deletions and substitutions and still be considered to be "derived from" the same species as the isolated fungal cell. Such one or more insertions, deletions and substitutions may result in increased or decreased expression or activity of the homologous PtaB-like protein. Similarly, a polynucleotide encoding a homologous PtaB-like protein may contain one or more insertions, deletions and substitutions (including substitutions that optimize codon usage without altering the sequence of the encoded protein).

A heterologous PtaB-like protein is encoded by a polynucleotide sequence that naturally occurs in, or is isolated or derived from, a different taxonomic species from the fungal cell. Furthermore, as is recognized by one of skill in the art, a heterologous PtaB-like protein may contain one or more insertions, deletions and substitutions and still be considered to be "derived from" a different taxonomic species from the isolated fungal cell. Such one or more insertions, deletions and substitutions may result in increased or decreased expression or activity of the heterologous PtaB-like protein. Similarly, a polynucleotide encoding a heterologous PtaB-like protein may contain one or more insertions, deletions and substitutions (including substitutions that optimize codon usage without altering the sequence of the encoded protein).

As used herein, in respect of polynucleotide sequences, "derived from" refers to the isolation of a target polynucleotide sequence using one or more molecular biology techniques known to those of skill in the art including, but not limited to, reverse translation of a polypeptide or amino acid sequence, cloning, sub-cloning, amplification by PCR, in vitro synthesis, and the like. Furthermore, as is recognized by one of skill in the art, a polynucleotide sequence that is derived from a target polynucleotide sequence may be modified by one or more insertions, deletions and substitutions and still be considered to be "derived from" that target nucleotide sequence. Such one or more insertions, deletions and substitutions may result in increased or decreased expression or activity of the protein of interest encoded by the polynucleotide sequence and may be located within a promoter sequence, the 5' or 3' untranslated regions, or within the coding region for the protein of interest.

As used herein with respect to polynucleotide sequences, "isolated" or "isolation" means altered from its natural state by virtue of separating the nucleic acid sequence from some or all of the naturally-occurring nucleic acid sequences with which it is associated in nature.

In other embodiments, the fungal cell may be genetically modified by transformation of the fungal cell with a PtaB genetic construct. As used herein, "PtaB genetic construct" refers to an isolated polynucleotide comprising elements necessary for increasing or decreasing the expression of a PtaB-like protein. These elements may include, but are not limited to, a polynucleotide sequence encoding a PtaB-like protein (coding sequence), a promoter operably linked to the coding sequence and comprising polynucleotide sequences that direct the transcription and translation of the coding sequence.

The isolated fungal cell of the present invention may further comprise one or more genetic constructs that direct the production of one or more homologous or heterologous biomass-degrading enzymes. Such constructs comprise polynucleotide elements including, but not limited to, a coding sequence for the biomass-degrading enzyme, a promoter operably linked to the coding sequence and comprising a polynucleotide sequence that directs the transcription of the coding region, and a sequence encoding a secretion signal peptide operably linked to the coding sequence, as well as targeting polynucleotide sequences that direct homologous recombination of the construct into the genome of the fungal cell. The terms "secretion signal peptide", "secretion signal" and "signal peptide" refer to any sequence of nucleotides and/or amino acids which may participate in the secretion of the mature or precursor forms of a secreted protein. The signal sequence may be endogenous or exogenous with respect to the fungal cell. The signal sequence may be that normally associated with the protein of interest or a gene encoding another secreted protein. The signal sequence may also be a "hybrid signal sequence" containing partial sequences from two or more genes encoding secreted proteins.

As understood by one of ordinary skill in the art, the coding sequence, promoter, and/or secretion signal may be derived from the parental fungal cell, from a different organism, and/or be synthesized in vitro. For example, the promoter and secretion signal may be derived from one or more genes encoding proteins that are highly expressed and secreted when a parental fungal cell is grown in the fermentation process defined below—for example, gene(s) encoding a cellulase, beta-glucosidase, cellulase-enhancing protein, a hemicellulase, or any combination thereof. These polynucleotide elements may also be altered or engineered by replacement, substitution, addition, or elimination of one or more nucleic acids relative to a naturally-occurring polynucleotide. However, it should be understood that the practice of the present invention is not limited by the choice of promoter in the PtaB genetic construct or by the choice of promoter and secretion signal in genetic constructs expression biomass-degrading enzymes.

The genetic constructs described above may contain a selectable marker for identification of transformed host cells. The selectable marker may be present on the genetic construct or the selectable marker may be a separate isolated polynucleotide that is co-transformed with the genetic construct. Choices of selectable markers are well known to those skilled in the art and include genes (synthetic or natural) that confer to the transformed cells the ability to utilize a metabolite that is not normally metabolized by the microbe (e.g., the *A. nidulans* amdS gene encoding acetamidase and conferring the ability to grow on acetamide as the sole nitrogen source) or antibiotic resistance (e.g., the *Escherichia coli* hph gene encoding hygromycin-beta-phosphotransferanse and conferring resistance to hygromycin). Alternatively, if the fungal cell expresses little or none of a chosen marker activity, then the corresponding gene may be used as a marker. Examples of such markers include trp, pyr4, pyrG, argB, leu, and the like. The corresponding host strain would therefore have to be lacking a functional gene corresponding to the marker chosen, i.e., lacking in the expression of trp, pyr, arg, leu and the like.

A genetic construct may contain a transcriptional terminator that is functional in the fungal cell, as would be known to one of skill in the art. The transcriptional terminator may be positioned immediately downstream of a coding sequence. The practice of the invention is not constrained by the choice of transcriptional terminator that is sufficient to direct the termination of transcription in the host cell.

A genetic construct may contain additional polynucleotide sequences between the various sequence elements as described herein. These sequences, which may be natural or synthetic, may result in the addition of one or more of the amino acids to the protein encoded by the construct. The practice of the invention is not constrained by the presence of additional polynucleotide sequences between the various sequence elements of the genetic constructs present in the fungal cell.

Methods of introducing a genetic construct into a fungal cell are familiar to those skilled in the art and include, but are not limited to, calcium chloride treatment of fungal protoplasts to weaken the cell membranes, addition of polyethylene glycol to allow for fusion of cell membranes, depolarization of cell membranes by electroporation, or shooting the construct through the cell wall and membranes via microprojectile bombardment with a particle gun. The practice of the present invention is not constrained by the method of introducing the genetic constructs into the fungal cell.

In some embodiments, the isolated fungal cell may be a species of the following genera of filamentous fungi: *Trichoderma, Hypocrea, Aspergillus, Fusarium, Penicillium, Neurospora, Chaetomium, Acremonium, Glomerella, Myceliophthora, Sporotrichum, Thielavia, Chrysosporium, Corynascus, Ctenomyces, Verticillium, Cordyceps, Nectria,* or *Magnaporthe,* including anamorphs and teleomorphs thereof, as well as recognized synonymous genera. For example, the isolated fungal cell may be a strain of the following fungal species: *T. reesei, H. jecorina, A. niger, A. fumigatus, A. orzyae, A. nidulans, F. oxysporum, N. crassa, C. thermophilum, A. thermophilum, G. graminicola, M. thermophila, S. thermophile, T. terrestris, T. heterothallica, C. thermophile, V. dahlia, C. militaris, N. heamatococca,* or *M. orzyae.*

It will be understood that for the aforementioned species, the isolated fungal cell presented herein encompasses both the perfect and imperfect states, and other taxonomic equivalents, e.g., anamorphs and teleomorphs, regardless of the species name by which they are known. Further examples of taxonomic equivalents can be found, for example, in Cannon, Mycopathologica 111:75-83, 1990; Moustafa et al., Persoonia 14:173-175, 1990; Stalpers, Stud. Mycol. 24, 1984; Upadhyay et al., Mycopathologia 87:71-80, 1984; Guarro et al., Mycotaxon 23: 419-427, 1985; Awao et al., Mycotaxon 16:436-440, 1983; von Klopotek, Arch. Microbiol. 98:365-369, 1974; and Long et al., 1994, ATCC Names of Industrial Fungi, ATCC, Rockville Md. Those skilled in the art will readily recognize the identity of appropriate equivalents. Accordingly, it will be understood that, unless otherwise stated, the use of a particular genus and/or species designation in the present disclosure also refers to genera and species that are related by anamorphic or teleomorphic relationship, genera and species that are recognized as synonymous, as well as those that have been or may be reclassified into one of the claimed genera or species in the future.

PtaB-Like Proteins and PtaB Polynucleotides

As used herein, a "PtaB-like protein" (or "PtaB protein" or "PtaB") refers to a polypeptide exhibiting from about 40% to 100% identity to the amino acid sequence of SEQ ID NO: 1 or from about 50% to about 100% identity to the amino acid sequence of SEQ ID NO: 3, SEQ ID NO: 4, SEQ ID NO: 5, SEQ ID NO: 7, SEQ ID NO: 9, SEQ ID NO: 11, or SEQ ID NO: 14. For example, a Pta-B like protein may exhibit 40%, 50%, 60%, 70%, 75%, 80%, 85%, 90%, 95% or 100% identity, or any % identity therebetween, to the amino acid sequence of SEQ ID NO: 1 or may exhibit 50%, 60%, 70%, 75%, 80%, 85%, 90%, 95% or 100% identity, or any % identity therebetween, to the amino acid sequence of SEQ ID NO: 3, SEQ ID NO: 4, SEQ ID NO: 5, SEQ ID NO: 7, SEQ ID NO: 9, SEQ ID NO: 11, or SEQ ID NO: 14.

The polypeptide of SEQ ID NO: 1 exhibits significant sequence homology to the polypeptide encoded by the *Aspergillus* ptaB gene ("pta" stands for "putative transcriptional activator") identified by Conlon et al., 2001, *Molecular Microbiology* 40: 361). The pta genes in *Aspergillus* were found as fusions with areB, a gene encoding a regulator of nitrogen metabolism, in strains of *Aspergillus* selected for suppression of mutations in areA, the principal regulator of nitrogen metabolism in *Aspergillus*. The genes ptaA, ptaB and ptaC were identified as fusions with areB that enabled the suppression phenotype. As their name and history imply, the actual functions of the pta genes are unknown. Homologues in genera other than *Aspergillus*, such as *Trichoderma* and *Myceliophthora*, are named by comparison to the *Aspergillus* prototype. A listing of fungal polypeptides identified as putative PtaB homologues and their source organisms are provided in Table 1.

TABLE 1

Fungal PtaB-like proteins

| Source Organism | GenBank accession Number | SEQ ID NO: | % Identity to SEQ ID NO: 1 |
|---|---|---|---|
| Trichoderma reesei | EGR46093.1 | 1 | 100.0 |
| Nectria heamatococca | XP_003048295.1 | 3 | 61.58 |
| Fusarium oxysporum | EGU75490.1 | 4 | 62.27 |
| Glomerella graminocola | EFQ32984.1 | 5 | 54.95 |
| Cordyceps militaris | EGX90369.1 | 6 | 35.24 |
| Verticillium dahliae | EGY22518.1 | 7 | 48.96 |
| Thielavia terrestris | AEO71320.1 | 8 | 40.07 |
| Verticillium albo-atrum | XP_003006908.1 | 9 | 43.42 |
| Neurospora crassa | XP_956246.1 | 10 | 38.02 |
| Chaetomium thermophilum | EGS23794.1 | 11 | 34.76 |
| Magnaporthe oryzae | XP_368187.1 | 12 | 39.59 |
| Botryotinia fuckeliana | CCD34135.1 | 13 | 34.63 |
| Sporotrichum thermophile | AEO61562 | 14 | 40.33 |

As shown in Table 1, the fungal polypeptides of SEQ ID NO: 3, 4, 5, 6, 7, 8, 9, 12 and 14 exhibit at least about 40% amino acid sequence identity to SEQ ID NO: 1. Additionally, as shown in FIG. 11, the fungal polypeptide of SEQ ID NO: 1, 3, 4, 5, 6, 7, 9, 11 or 14 may exhibit at least about 50% amino acid sequence identity to at least of one of the fungal polypeptides of SEQ ID NO: 1, 3, 4, 5, 6, 7, 9, 11 and 14 derived from another source organism.

As used herein, "identity" and "percent identity," in the context of two or more polypeptide sequences, refers to two or more sequences or subsequences that are the same or have a specified percentage of amino acid residues that are the same (e.g., share at least about 40%, at least about 50%, at least about 60%, at least about 70%, at least about 80% identity, at least about 85%, at least about 90%, at least about 95%, or at least about 100% identity) over a specified region to a reference sequence, when compared and aligned for maximum correspondence over a comparison window, or designated region as measured using a sequence comparison algorithms or by manual alignment and visual inspection.

In some embodiments, the terms "percent identity," "% identity," "percent identical," and "% identical," are used interchangeably herein to refer to the percent amino acid or polynucleotide sequence identity that is obtained by ClustalW analysis (version W 1.8 available from European Bioinformatics Institute, Cambridge, UK), counting the number of identical matches in the alignment and dividing such number of identical matches by the length of the reference sequence, and using the following ClustalW parameters to achieve slow/more accurate pairwise optimal alignments—DNA/Protein Gap Open Penalty:15/10; DNA/Protein Gap Extension Penalty:6.66/0.1; Protein weight matrix: Gonnet series; DNA weight matrix: Identity.

Two sequences are "aligned" when they are aligned for similarity scoring using a defined amino acid substitution matrix (e.g., BLOSUM62), gap existence penalty and gap extension penalty so as to arrive at the highest score possible for that pair of sequences. Amino acid substitution matrices and their use in quantifying the similarity between two sequences are well known in the art (See, e.g., Dayhoff et al., in Dayhoff [ed.], *Atlas of Protein Sequence and Structure,*" Vol. 5, Suppl. 3, Natl. Biomed. Res. Round., Washington D.C. [1978]; pp. 345-352; and Henikoff et al., Proc. Natl. Acad. Sci. USA, 89:10915-10919 [1992]. The BLOSUM62 matrix is often used as a default scoring substitution matrix in sequence alignment protocols such as Gapped BLAST 2.0. The gap existence penalty is imposed for the introduction of a single amino acid gap in one of the aligned sequences, and the gap extension penalty is imposed for each additional empty amino acid position inserted into an already opened gap. The alignment is defined by the amino acid position of each sequence at which the alignment begins and ends, and optionally by the insertion of a gap or multiple gaps in one or both sequences so as to arrive at the highest possible score. While optimal alignment and scoring can be accomplished manually, the process is facilitated by the use of a computer-implemented alignment algorithm (e.g., gapped BLAST 2.0; See, Altschul et al., Nucleic Acids Res., 25:3389-3402 [1997], which is incorporated herein by reference), and made available to the public at the National Center for Biotechnology Information Website). Optimal alignments, including multiple alignments can be prepared using readily available programs such as PSI-BLAST (e.g, Altschul et al., supra).

In some embodiments, the isolated fungal cell comprises an increase or decrease in copy number or expression of a "PtaB-encoding polynucleotide." As used herein, a "PtaB-encoding polynucleotide" or "PtaB polynucleotide" (as well as the terms "ptaB" and "PtaB gene") refers to a polynucleotide that hybridizes under at least high stringency conditions to any one of (i) the polypeptide coding sequence of SEQ ID NO: 2, (ii) a genomic DNA sequence comprising the polypeptide coding sequence of SEQ ID NO: 2, and (iii) a full-length complementary strand of (i) or ii), wherein high stringency conditions are prehybridization and hybridization at 42° C. for 12 to 24 hours in 5×SSPE, 0.3% SDS, 200 µg/mL sheared and denatured salmon sperm DNA, and 50% formamide followed by post-hybridization washes of three times each for 15 minutes using 2×SSC, 0.2% SDS at 65° C.

Polynucleotides and nucleic acids "hybridize" when they associate, typically in solution, due to a variety of well-characterized physico-chemical forces such as hydrogen bonding, solvent exclusion, base stacking, and the like. As used herein, the term "stringent hybridization wash conditions" in the context of hybridization experiments, such as Southern and Northern hybridizations, are sequence dependent, and are different under different environmental parameters. An extensive guide to the hybridization of nucleic acids is found in Tijssen, 1993, *Laboratory Techniques in Biochemistry and Molecular Biology—Hybridization with Nucleic Acid Probes,* Part I, Chapter 2 (Elsevier, New York), which is incorporated herein by reference. For polynucleotides of at least 100 nucleotides in length, low to very high stringency conditions are defined as follows: prehybridization and hybridization at 42° C. in 5×SSPE, 0.3% SDS, 200 µg/mL sheared and denatured salmon sperm DNA, and either 25% formamide for low stringencies, 35% formamide for medium and medium-high stringencies, or 50% formamide for high and very high stringencies, following standard Southern blotting procedures. For polynucleotides of at least 100 nucleotides in length, the carrier material is finally removed by washing three times each for 15 minutes using 2×SSC, 0.2% SDS 50° C. (low stringency), at 55° C. (medium stringency), at 60° C. (medium-high stringency), at 65° C. (high stringency), or at 70° C. (very high stringency).

Biomass

The terms "biomass" and "biomass substrate" encompass any suitable materials that comprise cellulose (i.e., "cellulosic biomass," "cellulosic feedstock," and "cellulosic substrate") and/or hemicellulose (e.g., xylan, arabinoxylan), as well as lignocellulosic biomass. Biomass can be derived from plants or microorganisms and includes, but is not limited to, agricultural, industrial, and forestry residues, industrial and municipal wastes, and terrestrial and aquatic crops grown for energy purposes. Examples of biomass substrates include, but are not limited to, wood, wood pulp, paper pulp, corn fiber, corn grain, corn cobs, crop residues such as corn husks, corn stover, grasses, wheat, wheat straw, barley, barley straw, hay, rice, rice straw, rice hulls, switchgrass, waste paper, paper and pulp processing waste, woody or herbaceous plants, fruit or vegetable pulp, distillers grain, cotton, hemp, flax, sisal, sugar cane bagasse, sorghum, soy, components obtained from milling of grains, trees, branches, roots, leaves, wood chips, sawdust, shrubs and bushes, vegetables, fruits, and flowers and any suitable mixtures thereof. In some embodiments, the biomass comprises, but is not limited to, cultivated crops (e.g., grasses, including C4 grasses, such as switch grass, cord grass, rye grass, miscanthus, reed canary grass, or any combination thereof), sugar processing residues, for example, but not limited to, bagasse (e.g., sugar cane bagasse, beet pulp [e.g., sugar beet], or a combination thereof), agricultural residues (e.g., soybean stover, corn stover, corn fiber, rice straw, sugar cane straw, rice, rice hulls, barley straw, corn cobs, wheat straw, canola straw, oat straw, oat hulls, corn fiber, hemp, flax, sisal, cotton, or any combination thereof), fruit pulp, vegetable pulp, distillers' grains, forestry biomass (e.g., wood, wood pulp, paper pulp, recycled wood pulp fiber, sawdust, hardwood, such as aspen wood, softwood, or a combination thereof).

Furthermore, in some embodiments, the biomass comprises cellulosic waste material and/or forestry waste materials, including but not limited to, paper and pulp processing waste, municipal paper waste, newsprint, cardboard and the like. Biomass may comprise one species of fiber or a mixture of fibers that originate from different biomasses. In some embodiments, the biomass comprises transgenic plants that express ligninase and/or cellulase enzymes (e.g., U.S. Publication No. 2008/0104724 A1).

As used herein, "lignocellulose" (or "lignocellulosic biomass" or "lignocellulosic substrate") refers to a matrix of cellulose, hemicellulose and lignin. Economic production of biofuels from lignocellulosic biomass typically involves conversion of the cellulose and hemicellulose components to fermentable sugars, typically monosaccharides such as glucose (from the cellulose) and xylose and arabinose (from the hemicelluloses). Nearly complete conversion can be achieved by a chemical pretreatment of the lignocellulose followed by enzymatic hydrolysis with cellulase enzymes. The chemical pretreatment step renders the cellulose more susceptible to enzymatic hydrolysis and, in some cases, also hydrolyzes the hemicellulose component. Numerous chemical pretreatment processes are known in the art, and include, but are not limited to, mild acid pretreatment at high temperatures and dilute acid, ammonium pretreatment or organic solvent extraction.

Lignin is a more complex and heterogeneous biopolymer than either cellulose or hemicellulose and comprises a variety of phenolic subunits. Enzymatic lignin depolymerization can be accomplished by lignin peroxidases, manganese peroxidases, laccases and cellobiose dehydrogenases (CDH), often working in synergy.

In some embodiments, the biomass is optionally pretreated to increase its susceptibility to enzymatic hydrolysis or degradation to produce a pretreated lignocellulosic substrate. A "pretreated lignocellulosic substrate", or "pretreated lignocellulose", is a material of plant origin that, prior to pretreatment, contains 20-90% cellulose (dry wt), more preferably about 30-90% cellulose, even more preferably 40-90% cellulose, for example 20, 22, 24, 26, 28, 30, 32, 34, 36, 38, 40, 42, 44, 46, 48, 50, 55, 60, 65, 70, 75, 80, 85, 90% or any % cellulose (dry wt) therebetween, and at least 10% lignin (dry wt), more typically at least 12% (dry wt) and that has been subjected to physical, chemical or biological processes to make the fiber more accessible and/or receptive to the actions of enzymes.

One method of performing acid pretreatment is steam explosion using the process conditions set out in U.S. Pat. No. 4,461,648. Another method of pretreating a biomass slurry involves continuous pretreatment, meaning that the lignocellulosic substrate is pumped though a reactor continuously. Continuous acid pretreatment is familiar to those skilled in the art; see, for example, U.S. Pat. No. 5,536,325; WO 2006/128304; and U.S. Pat. No. 4,237,226. Additional techniques known in the art may be used as required such as the process disclosed in U.S. Pat. No. 4,556,430.

The pretreatment may also be conducted with alkali. In contrast to acid pretreatment, pretreatment with alkali does not typically hydrolyze the hemicellulose component of the lignocellulosic substrate, but rather the alkali reacts with acidic groups present on the hemicellulose to open up the surface of the substrate. The addition of alkali may also alter the crystal structure of the cellulose so that it is more amenable to hydrolysis. Examples of alkali that may be used in the pretreatment include ammonia, ammonium hydroxide, potassium hydroxide, and sodium hydroxide. An example of a suitable alkali pretreatment is Ammonia Freeze Explosion, Ammonia Fiber Explosion or Ammonia Fiber Expansion ("AFEX" process) as described in U.S. Pat. Nos. 5,171,592; 5,037,663; 4,600,590; 6,106,888; 4,356,196; 5,939,544; 6,176,176; 5,037,663 and 5,171,592. The pretreatment is preferably not conducted with alkali that is insoluble in water, such as lime and magnesium hydroxide.

Yet a further non-limiting example of a pretreatment process for use in the present invention includes chemical treatment of the lignocellulosic substrate with organic solvents. Organic liquids in pretreatment systems are described by Converse et al. (U.S. Pat. No. 4,556,430), and such methods have the advantage that the low boiling point liquids easily can be recovered and reused. Other pretreatments, such as the Organosolv™ process, also use organic liquids (see U.S. Pat. No. 7,465,791). Subjecting the lignocellulosic substrate to pressurized water may also be a suitable pretreatment method (see Weil et al. (1997) *Appl. Biochem. Biotechnol*. 68(1-2): 21-40).

The pretreated lignocellulosic substrate may be processed after pretreatment by any of several steps, such as dilution with water, washing with water, buffering, filtration, or centrifugation, or a combination of these processes, prior to enzymatic hydrolysis, as is familiar to those skilled in the art. The pH of the pretreated lignocellulosic substrate slurry may be adjusted to a value that is amenable to the cellulase enzymes, which is typically between about 4 and about 8.

Biomass-Degrading Enzymes

The following definitions refer to classification of cellulases, hemicellulases and related proteins as defined by the by the Joint Commission on Biochemical Nomenclature of the International Union of Biochemistry and Molecular Biology (Published in *Enzyme Nomenclature* 1992, Academic Press, San Diego, Calif., ISBN 0-12-227164-5; with supplements in *Eur. J. Biochem*. 1994, 223, 1-5; *Eur. J. Biochem*. 1995, 232, 1-6; *Eur. J. Biochem*. 1996, 237, 1-5; *Eur. J. Biochem*. 1997, 250; 1-6, and *Eur. J. Biochem*. 1999, 264, 610-650; also see: chem.qmul.ac.uk/iubmb/enzyme/) and to the Glycoside Hydrolase (GH) families as defined by the CAZy system which is accepted as a standard nomenclature for glycohydrolase enzymes (Coutinho, P. M. & Henrissat, B., 1999, "Carbon-active enzymes: an integrated database approach." In *Recent Advances in Carbon Bioengineering*, H. J. Gilbert, G. Davies, B. Henrissat and B. Svensson eds., The Royal Society of Chemistry, Cambridge, pp. 3-12; also see: afmb.cnrs-mrs.fr/CAZY/) and is familiar to those skilled in the art.

Biomass-degrading enzymes are enzymes capable of, or that assist in, breaking down the biopolymers that comprise biomass into smaller oligomers or individual subunits. Typically, biomass-degrading enzymes are hydrolases that can break down cellulose, hemicellulose or related polysaccharides into oligo-, di-, or mono-saccharides, and include but are not limited to, cellulases, glucanases, hemicellulases, and the like.

The terms "biomass-degrading enzyme" also encompasses enzymes and proteins that do not participate directly in the breakdown of cellulose or hemicellulose polymers. Examples of such enzymes and proteins include beta-glucosidases and beta-xylosidases, which convert oligo- and di-saccharides to monosaccharides, acetyl xylan esterases and ferulic acid esterases, which hydrolyze ester linkages between lignin and hemicellulose, and non-hydrolytic proteins, including a variety of cellulase-enhancing proteins.

As used herein, the term "cellulase" refers to any enzyme that is capable of degrading cellulose. The term cellulase (or cellulase enzymes) broadly refers to enzymes that catalyze the hydrolysis of the β-1,4-glucosidic bonds joining individual glucose units in the cellulose polymer. The catalytic mechanism involves the synergistic actions of endoglucanases (E.C. 3.2.1.4) and cellobiohydrolases (E.C. 3.2.1.91). Endoglucanases (or "EG") hydrolyze accessible glucosidic bonds in the middle of the cellulose chain, while cellobiohydrolases release cellobiose from these chain ends processively. Cellobiohydrolases (or "CBH") are also referred to as exoglucanases. Most cellulases have a similar modular structure, which consists of one or more catalytic domain and one or more carbohydrate-binding modules (CBM) joined by flexible linker peptides. Most cellulases comprise at least one catalytic domain of Glycoside Hydrolase Family 5, 6, 7, 8, 9, 12, 44, 45, 48, 51, 61 and 74.

A "cellulase-enhancing protein" is a protein that enhances the rate or extent of cellulose hydrolysis by cellulase enzymes but does not exhibit significant cellulose-degrading activity on its own. Cellulase-enhancing proteins include, but are not limited to, proteins classified in Glycoside Hydrolase Family 61, as well as swollenins and expansins.

As used herein, the term "hemicellulase" refers to any enzyme that is capable of degrading hemicellulose. The term hemicellulase broadly refers to enzymes that catalyze the hydrolysis of the glycosidic bonds joining individual sugar units in the hemicellulose polymer. Hemicellulases include, but are not limited to, xylanase (E. C. 3.2.1.8), beta-mannanase (E.C. 3.2.1.78), alpha-arabinofuranosidase (E.C. 3.2.1.55), beta-xylosidases (E.C. 3.2.1.37), and beta-mannosidase (E.C. 3.2.1.25). Hemicellulases typically comprise a catalytic domain of Glycoside Hydrolase Family 1, 3, 5, 8, 10, 11, 26, 30, 39, 43, 51, 52, 54, 62, 113 or 116.

The terms "beta-glucosidase," "cellobiase," and "BGL" refer to enzyme members of EC 3.2.1.21 that catalyze the hydrolysis of cellobiose to glucose. Beta-glucosidases typically comprise a catalytic domain of Glycoside Hydrolase Family 1, 3, 5, 9, 30, or 116.

The terms "acetyl xylan esterase" (or "AXE") and "ferulic acid esterase" (or "FAE") refer to enzyme members of E.C. 3.1.1.72 and E.C. 3.1.1.73, respectively. AXEs typically comprise a catalytic domain of Carbohydrate Esterase Family 1, 2, 3, 4, 5, 6, 7, 12 or 15 or Glycoside Hydrolase Family 5 or 11, while FAEs typically comprise a catalytic domain of Carbohydrate Esterase Family 1 or Glycoside Hydrolase Family 10 or 78.

The practice of the present invention is not limited by the particular choice of the one or more biomass-degrading enzymes produced by the isolated fungal cells or fermentation processes described herein.

Fermentation Process for Producing Biomass-Degrading Enzymes

The fermentation processes of the present invention comprises culturing an isolated fungal cell with increased or decreased copy number or expression of a PtaB-like protein or a PtaB-encoding nucleotide in a submerged liquid fed-batch or continuous culture.

As used herein, the term "culturing" refers to growing a population of microbial cells under suitable conditions in a liquid or solid medium. The culturing may be carried out using conventional fermentation equipment suitable for such purpose (e.g., shake flasks, fermentation tanks, and bioreactors).

A "submerged liquid culture", as defined herein, is a microbial culture in which the microbial cells are suspended, or significantly suspended, in a liquid medium containing nutrients required for maintaining the viability of the cells. The culture is generally agitated at a sufficient rate to ensure distribution of the cells throughout the medium. The agitation rate is typically also selected to prevent formation of concentration gradients of nutrients.

In a "batch process" or "batch fermentation", all the necessary culture and media components, with the exception of oxygen for aerobic processes, are placed in a reactor at the start of the operation and the fermentation is allowed to proceed until completion, at which point the product is withdrawn from the reactor.

In a "fed-batch process" or "fed-batch fermentation", the culture is fed continuously or sequentially with one or more media components without the removal of the culture fluid.

In a "continuous process" or "continuous fermentation", fresh medium is supplied and culture fluid is removed continuously at volumetrically equal, or substantially equal, rates to maintain the culture at a steady growth rate. In reference to continuous processes, "steady state" refers to a state in which the concentration of reactants does not vary appreciably, and "quasi-steady state" refers to a state in which, subsequent to the initiation of the reaction, the concentration of reactants fluctuates within a range consistent with normal operation of the continuous hydrolysis process. Continuous fermentation process may also be referred to as CSTR (continuous stirred-tank reactor) fermentations. One example of a continuous fermentation process is a chemostat, in which the growth rate of the microorganism is controlled by the supply of one limiting nutrient in the medium.

In the fermentation processes of the present invention, the fungal cell may be first cultured in a batch fermentation typically containing a non-inducing carbon source. Upon completion of the batch fermentation, which is typically identified by the depletion of essentially all of the available carbon source, for example, when the concentration of the carbon source in the culture filtrate is no more than 1 g/L, the fungal cell is cultured in a fed-batch, continuous or combined fed-batch and continuous submerged liquid culture.

Fed-batch and continuous processes are typically carried out in one or more bioreactors. Typical bioreactors used for microbial fermentation processes include, but are not limited to, mechanically agitated vessels or those with other means of agitation (such as air injection). Bioreactors may be temperature and pH-controlled. Typically, there are means provided to clean the reactor, sometimes in place. Means may also be provided to sanitize or sterilize the bioreactor prior to introduction of the target organism so as to minimize or prevent competition for carbon sources from other organisms. Bioreactors may be constructed from many materials, but most often are of glass or stainless steel. Provisions are generally made for sampling (in a manner that prevents or minimizes the introduction of undesirable competing organisms). Means to obtain other measurements are often provided (e.g., ports and probes to measure dissolved oxygen concentration or concentration of other solutes such as ammonium ions). The practice of the invention is not limited by the choice of bioreactor(s).

In the fermentation processes of the present invention, the fed-batch, continuous or combined fed-batch and continuous submerged liquid culture is provided with a feed solution containing a carbon source. In some embodiments, the carbon source consists of one or more cellulase-inducing carbohydrate, one or more hemicellulose-derived carbohydrate, one or more non-inducing carbohydrate, a mixture of cellulase-inducing and hemicellulose-derived carbohydrate, a mixture of cellulase-inducing and non-inducing carbohydrate, a mixture of hemicellulose-derived and non-inducing carbohydrate, or a mixture of cellulase-inducing, hemicellulose-derived, and non-inducing carbohydrate.

As used herein, the term "carbon source" refers to a carbon-containing substance that provides the major part of the carbon required for growth of, and production of biomass-degrading enzymes by, a parental or isolated fungal cell. For the purposes herein, a carbon source may be one or more carbohydrate, a non-carbohydrate substance such as a sugar alcohol, organic acid, or alcohol, or combinations thereof. However, for the purposes herein, organic nitrogen sources that may be provided to the parental or isolated fungal cell are not considered carbon sources.

As used herein, the term "cellulose-inducing carbohydrate" or "CIC" refers to one or more poly-, oligo- or di-saccharide that leads to the induction of cellulase production by an isolated or a parental fungal cell. By induction, it is meant the switching on of the expression of one or more cellulase genes, whether endogenous or recombinant, in response to the CIC. Non-limiting examples of cellulase-inducing carbohydrates include cellulose, lactose, cellobiose, sophorose, gentiobiose, and a combination thereof. Cellulase-inducing carbohydrate (CIC) may be produced by enzymatic conversion of cellulose with one or more cellulase enzymes to beta-linked glucose dimers. Alternatively, a high concentration glucose syrup can be condensed chemically or enzymatically to form mixtures of glucose dimers. For example, the condensation reaction to convert glucose to CIC may be catalyzed by dilute acid and performed at temperatures above 120-150° C., or by beta-glucosidase or cellulase enzymes at more moderate temperatures of about 40-70° C. (U.S. Publication No. 2004/0121446A1).

As used herein, the term "hemicellulose-derived carbohydrate" or "HDC" refers to one or more poly-, oligo-, di- or mono-saccharide that may be released by the chemical or enzymatic depolymerization of hemicellulose and which can be utilized by an isolated or a parental fungal cell for growth, production of biomass degrading enzymes or both. Non-limiting examples of HDC include xylan, arabinoxylan, xylo-oligosaccharides, arabinoxylo-oligosaccharides, D-xylose, xylobiose, L-arabinose, D-mannose and D-galactose. Preferably, the HDC contains D-xylose and/or L-arabinose.

As used herein, the term "non-inducing carbohydrate" or "NIC" refers to those carbohydrates and other non-carbohydrate carbon sources (e.g., glycerol, sugar alcohols and organic acids), that can be readily metabolized by, but that are known either to have no effect on or to repress the production of biomass degrading enzymes from an isolated or a parental fungal cell. Typically, NIC, when provided alone or in combination with CIC or HDC, results in the production of negligible or very low amounts of biomass degrading enzymes. For the purposes herein, NIC includes, but is not limited to, glucose, dextrose, sucrose, fructose, glycerol, and combinations thereof, whether in pure form or in semi-purified form, such as molasses.

In the fermentation process of the present invention, the feed solution may contain one or more additional components, such as nitrogen sources, vitamins, minerals and salts required for growth of the fungal cell as in known to one of skill in the art. Nitrogen sources may be inorganic and/or organic in nature and include, but are not limited to, one or more amino acids, peptides and proteins, in pure or raw form (e.g., corn steep liquor), any number of protein hydrolysates (peptone, tryptone, casamino acids), yeast extract, ammonia, ammonium hydroxide, ammonium salts, urea, nitrate and combinations thereof. The practice of the fermentation process of the present invention is not limited by the additional components of the feed solution.

The feed solution is provided to the fermentation process at a rate, the feed rate or "carbon addition rate" or "CAR" (measured as g carbon per liter per hour). In the fermentation process of the present invention, the feed solution may be provided to a fed-batch culture at a carbon addition rate of from about 0.2 to about 4 g carbon/L culture/h or any rate therebetween, for example 0.2, 0.3, 0.4, 0.6, 0.8, 1.0, 1.2, 1.4, 1.6, 1.8, 2.0, 2.2, 2.5, 3.0, 3.5, and 4.0 g carbon/L culture/h or any rate therebetween. Alternatively, the feed solution may be provided to a continuous culture at a dilution rate of from about 0.001 to 0.11 $h^{-1}$, or any dilution rate therebetween, for example at about 0.001, 0.005, 0.01, 0.02, 0.03, 0.04, 0.05, 0.06, 0.07, 0.08, 0.09, 0.11 $h^{-1}$, or any dilution rate therebetween.

The fermentation processes of the present invention may be carried at a temperature from about 20° C. to about 55° C., or any temperature therebetween, for example from about 30° C. to about 45° C., or any temperature therebetween, or from 20, 22, 25, 28, 30, 32, 35, 38, 40, 42, 45, 48, 50° C., 55° C. or any temperature therebetween.

The fermentation processes of the present invention may be carried out at a pH from about 2.5 to 8.5, or any pH therebetween, for example from about pH 3.5 to pH 7.0, or any pH therebetween, for example from about pH 2.5, 3.0, 3.2, 3.5, 3.8, 4.0, 4.2, 4.5, 4.8, 5.0, 5.2, 5.4, 5.5, 5.7, 5.8, 6.0, 6.2, 6.5, 6.8, 7.0, 7.2, 7.5, 7.8, 8.0, 8.5 or any pH therebetween. The pH may be controlled by the addition of a base, such as ammonium or sodium hydroxide, or by the addition of an acid, such as phosphoric acid.

The fermentation processes of the present invention may be carried out over a period of about 1-90 days, or any period therebetween, for example between 3 and 30 days, or any amount therebetween, between 3 and 8 days, or any amount therebetween, or from 1, 2, 3, 4, 5, 6, 7, 8, 9, 10, 12, 14, 16, 18, 20, 22, 24, 26, 28, 30, 40, 50, 60, 70, 80, or 90 days, or any amount therebetween.

The fermentation processes of the present invention may be performed in cultures having a volume of at least 0.5 liter, for example from about 0.5 to about 1,000,000 liters, or any amount therebetween, for example, 5 to about 400,000 liters, or any amount therebetween, 20 to about 200,000 liters, or any amount therebetween, or 2,000 to about 200,000 liters, or any amount therebetween, or from about 0.5, 1, 10, 50, 100, 200, 400, 600, 800, 1000, 2000, 4000, 6000, 8000, 10,000, 15,000, 20,000, 25,000, 30,000, 35,000, 40,000, 45,000, 50,000, 55,000, 60,000, 65,000, 70,000, 75,000, 80,000, 85,000, 90,000, 95,000, 100,000, 150,000, 200,000, 300,000, 400,000, 500,000, 750,000 or 1,000,000 liters in volume, or any amount therebetween.

The fermentation processes of the present invention may be performed aerobically, in the presence of oxygen, or anaerobically, in the absence of oxygen. For example, the process may be performed aerobically such that air or oxygen gas is provided to the submerged liquid culture at a superficial gas velocity of from about 0.001 to about 100 cm/s, or any rate therebetween, for example any rate from about 0.01 to about 20 cm/s, or any rate therebetween. An alternative parameter to measure aeration rate that is known to one of skill in the art is vessel volumes per minute (vvm). In the fermentation process of the present invention, air or oxygen gas is provided to the submerged liquid culture at a rate of from about 0.5 to about 5 vvm, or any rate therebetween. Antifoaming agents (either silicone, or non-silicone based) may be added to control excessive foaming during the process as required and as is known to one of skill in the art.

The fermentation process according to the present invention results in biomass-degrading enzymes being produced from an isolated fungal cell exhibiting increased expression or copy number of a PtaB polynucleotide or increased expression of a PtaB-like proteins. Such fermentation process may result in a population of fungal cells with a 50% reduction in cel-phenotype relative to an equivalent process utilizing a parental fungal cell. Such fermentation process may be characterized by an increase in "sustained productivity" relative to an equivalent fermentation process utilizing a parental fungal cell from which the isolated fungal cell is derived.

As used herein, the term "cel-phenotype" or "cel-" refers to a fungal cell that cannot produce any cellulase protein when provided with a carbon source containing a cellulase-inducing carbohydrate. For example, fungal cells exhibiting a cel-phenotype do not produce halos or clearing zones of digested cellulose around fungal colonies growing on agar media containing a cellulose substrate, as provided in Example 6. Alternatively, fungal cells exhibiting a cel-phenotype do not secrete measurable cellulase protein into culture medium when the fungal cells are grown in liquid culture medium containing a cellulase-inducing carbohydrate.

There are several assays for measuring cellulase activity known to one of skill in the art. Methods to measure cellulase activity are published (e.g., *Methods in Enzymology* 160, *Biomass Part A: Cellulose and Hemicellulose*, Wood, W. A. and Kellogg, S. T., eds, Academic Press Inc. 1988; Ghose, T. K. (1987) Pure & Appl. Chem. 59(2):257-268) and include, for example, release of glucose or soluble oligo-saccharides from a cellulose substrate, release of a chromophore or fluorophore from a cellulose derivative, e.g., azo-CMC, or from a small, soluble substrate such as methylumbelliferyl-beta-D-cellobioside, para-nitrophenyl-beta-D-cellobioside, para-nitrophenyl-beta-D-lactoside and the like. For example, hydrolysis of cellulose can be monitored by measuring the enzyme-dependent release of reducing sugars, which are quantified in subsequent chemical or chemienzymatic assays known to one of skill in the art, including reaction with dinitrosalisylic acid (DNS). In addition, cellulose or colorimetric substrates (cellulose derivatives or soluble substrates) may be incorporated into agar-medium on which a host microbe expressing and secreting one or more cellulase enzymes is grown. In such an agar-plate assay, activity of the cellulase is detected as a coloured or colourless halo around the individual microbial colony expressing and secreting an active cellulase.

As used herein, the term "specific productivity", alternatively expressed as "$q_p$", refers to the rate at which secreted protein is produced from a given mass of fungal cells. Typically, the specific productivity of a fermentation process is expressed as mg protein per g of fungal cells per hour (mg protein/g cells/h) and is calculated by measuring the concentration, in mg/L, of protein in culture filtrates (culture media from which the fungal cells have been removed) and dividing by the concentration of fungal cells (in g dry weight per L) in the culture medium and dividing by the total time, in h, since the feed solution was initially provided to the culture. The fermentation processes of the present invention may also be characterized by "maximum productivity" (or "maximum $q_p$"), which is the highest value $q_p$ calculated during the course of the fermentation process, or by "average productivity" (or "average $q_p$"), which is the average of all of the values of $q_p$ calculated during the course of the fermentation process Methods to measure concentration of secreted protein in culture filtrates include the methods of Bradford (Bradford, M. M. et al. (1976) *Anal. Biochem.* 72: 248-254), Lowry (Lowry O H, et al. (1951) *J. Biol. Chem.* 193: 265-175), and Smith (Smith, P. K., et al. (1985). *Anal. Biochem.* 150: 76-85). Increased production of individual cellulase enzymes can be measured, for example, with immunochemical methods such as ELISA (Van Weemen, B. K. et al. (1971) *FEBS Letters* 15: 232-236) with antibodies specific to the individual enzyme. Methods to measure concentration of fungal cells, in g dry weight per L of culture medium, are provided in Example 5.

Figure 7:
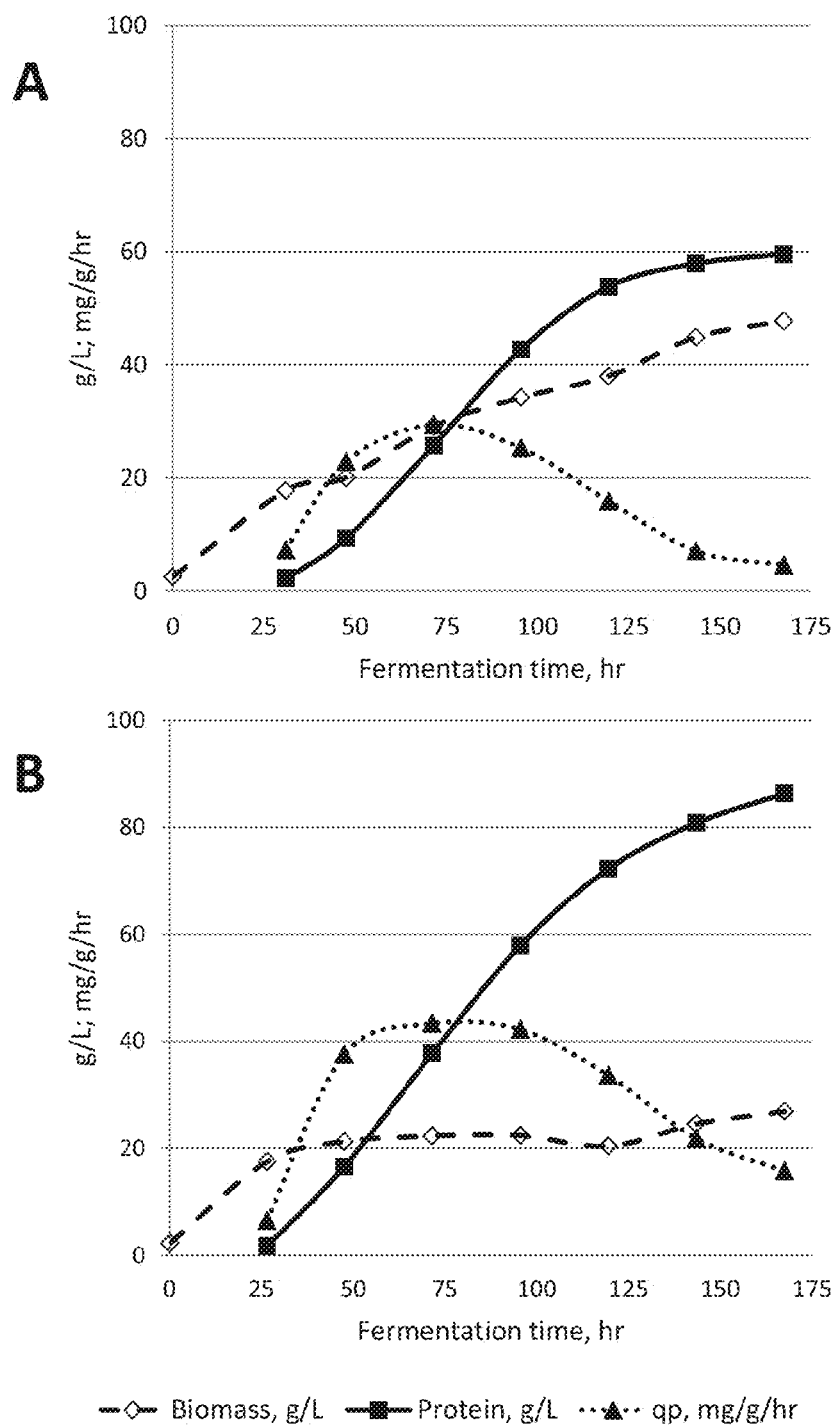
FIG. 7 shows pilot fermentation profiles of a PtaB overexpression strain (A) and its parental strain (B). Fed-batch fermentations were performed as described in Example 5 at a carbon addition rate of ~1.0 g of carbon per liter per h using a mixture of cellulase-inducing and hemicellulose-derived carbohydrates. Accumulation of biomass (dotted lines, open diamonds) and total protein (solid lines, closed circles) were measured every 24 h after fermentation start.

As a result of the decreased population of fungal cells exhibiting a cel-phenotype, fermentation processes conducted at a CAR less than 1 g carbon per liter per hour, for example at a CAR of 0.4 g/l/h), and utilizing an isolated fungal cell comprising increased expression or copy number of a PtaB polynucleotide or increased expression of a PtaB-like protein may be characterized by an increase in sustained productivity. By "sustained productivity" or "sustained $q_p$", it is meant the number of hours during which a fermentation process exhibits at least 70% of its maximum productivity or maximum $q_p$. As shown in FIGS. 7 and 8, fermentation processes with isolated fungal cells comprising increased expression or copy number of a PtaB polynucleotide or increased expression of a PtaB-like proteins, have a longer sustained $q_p$ relative to equivalent fermentation processes utilizing the parental fungal cell.

According to one aspect of the present invention, there is provided a fermentation process in which the one or more biomass-degrading enzyme is produced from an isolated fungal cell exhibiting increased expression or copy number of a PtaB polynucleotide, or increased expression of a PtaB-like proteins, wherein the process results in a population of fungal cells with at least a 50% reduction in cel-phenotype relative to an equivalent process utilizing a parental fungal cell. For example, such fermentation process may result in a population of fungal cells with at least a 50%, 55%, 60%, 65%, 70%, 75%, 80%, 85%, 90%, 95% or 100% reduction, or any amount therebetween, in cel-phenotype. Typically, this reduction in cel-phenotype is observed in the fungal cell population after at least about 96 hours after the initiation of the fed-batch or continuous culturing step. For example, the reduction in cel-phenotype may be observed in the fungal cell population after at least about 96 h, 108 h, 120 h, 132 h, 144 h, 156 h, 168 h, 180 h, 192 h, 204 h, or any time therebetween or later, after the initiation of the fed-batch or continuous culturing step. Such fermentation process may also be characterized by a specific productivity that is equal to or higher than that of an equivalent fermentation process utilizing a parental fungal cell from which the isolated fungal cell is derived.

A fermentation process according to the present invention in which the one or more biomass-degrading enzyme is produced from an isolated fungal cell exhibiting decreased expression or copy number of a PtaB polynucleotide, or decreased expression of a PtaB-like protein, exhibits at least a 50% increase in maximum specific productivity ($q_p$) relative to that exhibited by an equivalent process utilizing a parental fungal cell from which the isolated fungal cell is derived. For example, such fermentation process may exhibit at least a 50%, 60%, 70%, 80%, 90%, 100%, 150%, 200%, 300%, 400%, 500% or higher increase in maximum specific productivity ($q_p$) relative to that exhibited by an equivalent process utilizing a parental fungal cell from which the isolated fungal cell is derived.

As used herein, the terms "equivalent fermentation process" or "equivalent process", refer to a fermentation process in which a parental fungal cell is cultured under identical or nearly identical conditions of medium composition, time, cell density, temperature, and pH, as those used to culture an isolated fungal cell derived from that parental fungal cell.

Use of Biomass-Degrading Enzymes

The one or more biomass-degrading enzymes produced by the isolated fungal cell and/or fermentation processes of the present invention may be used in process to convert biomass to soluble sugars.

As contemplated herein, a biomass substrate may be treated with one or more biomass-degrading enzymes produced by the isolated fungal cell and/or fermentation processes of the present invention to produce soluble sugars. Examples of soluble sugars include, but are not limited to, glucose, cellobiose, cellodextrins, xylose, arabinose, galactose, mannose or mixtures thereof. The soluble sugars may be predominantly cellobiose and glucose.

Treatment of the biomass substrate with the one or more biomass-degrading enzymes may be carried out at a pH and temperature that is at or near the optimum for the biomass-degrading enzyme(s). For example, the treatment may be carried out at about 30° C. to about 75° C., or any temperature therebetween, for example a temperature of 30, 35, 40, 45, 50, 55, 60, 65, 70, 75° C., or any temperature therebetween, and a pH of about 3.5 to about 8.0, or any pH therebetween, for example a pH of 3.5, 4.0, 4.5, 5.0, 5.5, 6.0, 6.5, 7.0, 7.5, 8.0 or any pH therebetween.

The initial concentration of biomass substrate at the start of the treatment process is preferably about 0.01% (w/w) to about 20% (w/w), or any amount therebetween, for example 0.01, 0.05, 0.1, 0.5, 1, 2, 4, 6, 8, 10, 12, 14, 15, 18, 20% or any amount therebetween. The combined dosage of all biomass-degrading enzymes may be about 0.001 to about 100 mg protein per gram substrate, or any amount therebetween, for example 0.001, 0.01, 0.1, 1, 5, 10, 15, 20, 25, 30, 40, 50, 60, 70, 80, 90, 100 mg protein per gram substrate or any amount therebetween.

The treatment process may be carried out for a time period of about 0.5 hours to about 200 hours, or any time therebetween, for example, the treatment process may be carried out for a period of 2 hours to 100 hours, or any time therebetween, or it may be carried out for 0.5, 1, 2, 5, 7, 10, 12, 14, 15, 20, 25, 30, 35, 40, 45, 50, 55, 60, 65, 70, 75, 80, 85, 90, 95, 100, 120, 140, 160, 180, 200 hours or any time therebetween.

The treatment process may be conducted as a batch, continuous, or a combined batch and continuous reaction, which may be agitated, unmixed, or a combination thereof. The treatment process is typically carried out in a reactor. The one or more biomass-degrading enzymes may be added to the biomass substrate prior to, during, or after the addition of the substrate to the hydrolysis reactor.

It should be appreciated that the reaction conditions are not meant to limit the invention in any manner and may be adjusted as desired by those of skill in the art.

EXAMPLES

Example 1: Host *Trichoderma* Strains for the Deletion and Overexpression of ptaB Gene The host *Trichoderma reesei* strains used for the deletion of ptaB gene is M2C38aux derived from strain Rut-C30. Strain Rut-C30 (ATCC Deposit No. 56765) was isolated as a high cellulase producing derivative of progenitor strain QM6a (Montenecourt and Eveleigh, 1979, supra). Cellulase hyper-producing strains were generated from Rut-C30 by random mutation and/or selection. Strain M2C38 was isolated based on its ability to produce larger clearing zones than Rut-C30 on minimal media agar containing 1% acid swollen cellulose and 4 g/L 2-deoxyglucose. The ura3 auxotroph of strain M2C38 (strain M2C38aux), deficient in uracil production, was isolated based on the ability to grow on minimal media agar supplemented with 5 mM uridine and 0.15% (w/v) of 5-fluoro-orotic acid.

The host *Trichoderma reesei* strain used for the overexpression of ptaB gene is BTR213, which is derived from strain M2C38. BTR213 was isolated during random mutagenesis and selection for ability to produce larger clearing zones on minimal media agar containing 1% acid swollen cellulose and 4 g/L 2-deoxyglucose followed by selection on lactose media containing 0.2 µg/mL carbendazim. The ura3 auxotroph of strain BTR213 (strain BTR213aux), deficient in uracil production, was isolated based on the ability to grow on minimal media agar supplemented with 5 mM uridine and 0.15% (w/v) of 5-fluoro-orotic acid. BTR213 strain contains C432T mutation the PtaB-like protein of SEQ ID NO: 1. This mutation results in substitution of glutamine codon to stop codon and truncation of protein to 118 amino acids in length instead of 721 amino acids.

Example 2: Construction of *Trichoderma reesei* ptaB Deletion Cassette

Example 2.1: *Trichoderma reesei* Genomic DNA Isolation and Amplification of ptaB (EGR46093.1) Flanking Sequences For genomic DNA isolation, *T. reesei* spores collected from a Potato Dextrose Agar (PDA) plate were inoculated in 50 mL of Potato Dextrose Broth (PDB) (Difco™) The cultures were shaken at 200 rpm for 2-3 days at 28° C. The mycelia were filtered onto a glass fiber circles (GFA) (Fisher Cat. #09-804-424) and washed with cold, deionized water. The fungal cakes were frozen in liquid nitrogen and crushed into a powder with a pre-chilled mortar and pestle; 0.5 g of powdered mycelia was resuspended in 5 mL of buffer containing 100 mM Tris, 50 mM EDTA, pH 7.5 and 1% sodium dodecyl sulphate (SDS). The lysate was centrifuged (5000×g for 20 min at 4° C.) to pellet cell debris. The supernatant was extracted with 1 volume of TE buffer (10 mM Tris, 1 mM EDTA, pH 8.0) saturated phenol followed by extraction with 1 volume of buffer-saturated phenol:chloroform:isoamyl alcohol (25:24:1). Genomic DNA was precipitated from the solution by adding 0.1 volume of 3 M sodium acetate, pH 5.2 and 2.5 volumes of cold 95% ethanol. After incubating for at least 1 h at −20° C., the DNA was pelleted by centrifugation (5000×g for 20 min at 4° C.), rinsed with 10 mL of 70% ethanol, air-dried and resuspended in 1 mL of TE buffer. The RNA was digested by the addition of Ribonuclease A (Sigma-Aldrich) (final concentration of 0.1 mg/mL) and incubation at 37° C. for 1 hour. Ribonuclease was removed by extracting with 1 volume of buffer-saturated phenol and 1 volume of buffer-saturated phenol:chloroform:isoamyl alcohol (25:24:1). The DNA was precipitated with 0.1 volumes of 3 M sodium acetate, pH 5.2 and 2.5 volumes of cold 95% ethanol, pelleted by centrifugation, rinsed with 70% ethanol, air-dried and resuspended in 0.05 mL of TE buffer. The concentration of DNA was determined by measuring the absorbance of the solution at 260 nm.

A DNA fragment comprising 274 nucleotides of the 3' end of PtaB coding sequence and 1374 nucleotides of the ptaB terminator and 3' flanking sequences (SEQ ID NO:) was amplified from *T. reesei* genomic DNA using iProof® High Fidelity DNA polymerase (Bio-Rad) and following primers: forward—AC985 GAACCTCCCGGGGTCGCCTCA-CATC (SEQ ID NO: 15) and reverse—AC986 GCTG-CAACGAACGTCCTTTGCATC (SEQ ID NO: 16). The PCR was performed according to manufacturer's protocol with an annealing temperature of 60° C. and 75 seconds extension time for 30 cycles. The 1.65 kb amplicon was gel extracted and purified with the Wizard® SV Gel and PCR Clean-up System (Promega). The purified PCR product was used as a template for a second PCR to add overhangs homologous to vector sequences for recombinase-based cloning with the following primers: forward—AC987 TGAAGCCGATGTCACACGCGTGAACCTC-CCGGGGTCGCCTCACATC (SEQ ID NO: 17) and reverse—AC988 ACGCAGCTAGCAGCTGGTACCGCT-GCAACGAACGTCCTTTGCATC (SEQ ID NO: 18). The PCR was performed according to manufacturer's protocol with an annealing temperature of 60° C. and 75 seconds extension time for 30 cycles. The 1.65 kb amplicon was gel extracted and purified with the Wizard® SV Gel and PCR Clean-up System (Promega).

A 1.97 kb DNA fragment containing the ptaB promoter and 5' flanking sequences was amplified from *T. reesei* genomic DNA using iProof® High Fidelity DNA polymerase (Bio-Rad) and the following primers: forward—AC956 CTCTCGATGATGCGTGTAAG (SEQ ID NO: 19) and reverse—AC957 CCATACTCGTAGCCATCATC (SEQ ID NO: 20). The PCR was performed according to manufacturer's protocol with an annealing temperature of 60° C. and 75 seconds extension time for 30 cycles. The 1.97 kb amplicon was gel extracted and purified with the Wizard® SV Gel and PCR Clean-up System (Promega). The purified PCR product was used as a template for a second PCR to add overhangs homologous to vector sequences for recombinase-based cloning with the following primers: forward—AC989 GTACTGAGAGTGCACCATATGCTCTCGAT-GATGCGTGTAAG (SEQ ID NO: 21) and reverse—AC990 TCGGTTCTTAATTAAGAATTCCCATACTCGTAGC-CATCATC (SEQ ID NO: 22). The PCR was performed according to manufacturer's protocol with an annealing temperature of 60° C. and 75 seconds extension time for 30 cycles. The 1.97 kb amplicon was gel extracted and purified with the Wizard® SV Gel and PCR Clean-up System (Promega).

Example 2.2: Construction of the ptaB Deletion Vector

Figure 1:
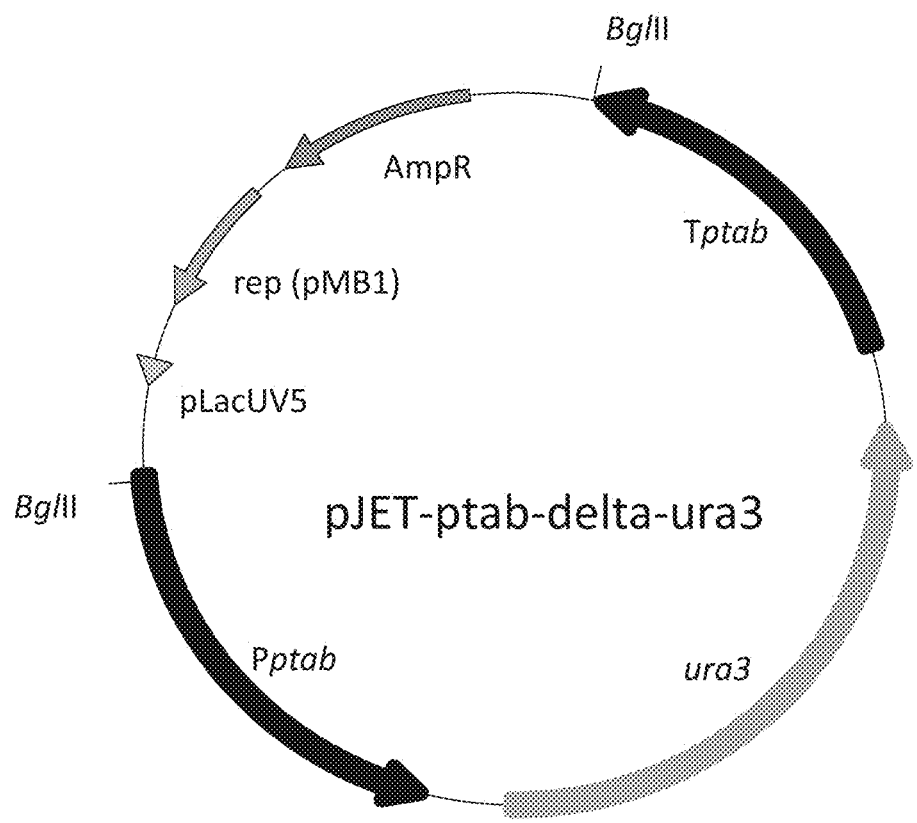
FIG. 1 shows a map of the pJET-ptaB-delta-ura3 vector used to delete the ptaB gene from isolated *T. reesei* cells. PptaB—ptaB promoter and 5' flank sequences; TptaB—ptaB terminator and 3' flank sequences; ura3—fungal selection marker cassette encoding *T. reesei* orotidine-5'-monophosphate decarboxylase; AmpR—resistance to ampicillin conferring bacterial selection marker; rep(pMB1)—replication origin; pLacUV5—LacUV5 promoter.

The PCR product containing the ptaB 3' coding sequence, terminator and 3' flank was recombined into a vector containing ura3 selection marker cassette, pTrBxl1p-NheI-KpnI-Tr7at-Ura3, digested MluI/KpnI using In-Fusion® Cloning Kit (Clontech) to produce an intermediate vector. The recombination reaction was completed according to the manufacturer's protocol. The PCR product containing the ptaB promoter and 5' flank was recombined into the intermediate vector digested EcoRI/NdeI to yield the deletion cassette containing ura3 selection marker cassette flanked with 5' and 3' ptaB targeting sequences. The full 6.97 kb deletion cassette was then amplified by PCR with primers: forward—AC956 CTCTCGATGATGCGTGTAAG (SEQ ID NO: 19) and reverse—AC986 GCTGCAACGAACGTC-CTTTGCATC (SEQ ID NO: 16) and iProof® High Fidelity DNA polymerase (Bio-Rad). The PCR reaction was performed according to the manufacturer's protocol with an annealing temperature of 60° C. and 5 minutes of extension time for 30 cycles. The 6.97 kb PCR product was purified using the Wizard® SV Gel and PCR clean-up System (Promega) and cloned into the pJET1.2™ (Fermentas) resulting in the vector pJET-ptaB-delta-ura3 (FIG. 1).

Example 3: Generation of Isolated Fungal Cells by Deletion of PtaB-Encoding Polynucleotide The pJET-ptaB-delta-ura3 transformation vector was introduced into *T. reesei* strain M2C38aux using the PEG-mediated protoplast transformation method. Approximately 5×10⁶ spores of M2C38aux were plated onto sterile cellophane placed on PDA supplemented with 5 mM uridine and incubated for 20 hours at 30° C. Cellophane discs with mycelia were transferred to 10 mL of a protoplast preparation solution containing 7.5 g/L Driselase® *Basidiomycetes* sp. (Sigma) and 4 g/L beta-glucanase (InterSpex Products Inc.) in 50 mM potassium phosphate buffer, pH 6.5 containing 0.6 M ammonium sulfate (Buffer P). The mycelia were digested for 5 hours at 28° C. with gentle agitation at 60 rpm. Protoplasts were collected by centrifugation at 1000-1500×g for 10 min at room temperature and washed with 5 mL of Buffer P. The pellet was resuspended in 1 mL of STC buffer (1.2 M sorbitol, 10 mM $CaCl_2$, 10 mM Tris-HCl, pH 7.5), separated from undigested mycelia by filtration through sterile 30 μM Nylon Net filter (Millipore) and collected into a sterile microcentrifuge tube. For transformation, 0.1 mL of protoplast suspension (approximately 5×10⁶ protoplasts) was combined with 10 μg of BglII digested vector DNA, and 25 μL of PEG solution (25% PEG 4000, 50 mM $CaCl_2$, 10 mM Tris-HCl, pH 7.5). Protoplasts with DNA were incubated on ice for 30 min then 1 mL of PEG solution was added and the mixture incubated for 5 min at room temperature. Transformation mix was diluted with 2 mL of 1.2 M sorbitol in PEG solution.

The transformation mix with BglII linearized pJET-ptaB-delta-ura3 plasmid and protoplasts of strain M2C38aux were added into 50 mL of molten MMSS agar media (see below) cooled to 50° C. and the protoplast suspension was split over two MM agar (see below) plates. Plates were incubated at 30° C. until colony growth was visible. Transformants were transferred to individual plates containing MM agar and allowed to sporulate. Spores were collected and plated at high dilution on MM agar to isolate homokaryon transformants, which were then plated onto PDA (Difco™) and incubated at 30° C. for sporulation and subsequent genetic analysis.

| Minimal medium (MM) agar: | |
|---|---|
| Component* | Amount for 1L of medium |
| $KH_2PO_4$ | 10 g |
| $(NH_4)_2SO_4$ | 6 g |
| $Na_3Citrate \cdot 2H_2O$ | 3 g |
| $FeSO_4 \cdot 7H_2O$ | 5 mg |
| $MnSO_4 \cdot H_2O$ | 1.6 mg |
| $ZnSO_4 \cdot 7H_2O$ | 1.4 mg |
| $CaCl_2 \cdot 2H_2O$ | 2 mg |
| Agar | 20 g |
| 20% Glucose f.s. | 50 mL |
| 1M $MgSO_4 \cdot 7H_2O$ f.s. | 4 mL |
| | pH to 5.5 |

*MMSS agar contains the same components as MM agar plus 1.2M sorbitol, 4 mM $MgSO_4$, 1 g/L YNB (Yeast Nitrogen Base w/o Amino Acids from DIFCO Cat. No. 291940) and 0.12 g/L amino acids (-Ura DO Supplement from Clontech Cat. No. 8601-1).

Example 4: Genetic Characterization of Isolated Fungal Cells

The deletion of the PtaB-encoding gene in isolated fungal cells was assessed by PCR on extracted genomic DNA samples using specific primers as described below. For genomic DNA extraction protoplasts from mitotically stable transformants were prepared as for PEG-mediated transformation described in Example 3. DNA was then extracted from the protoplasts using the Wizard® Genomic DNA Purification Kit (Promega, Cat. #A1120) as described in manufacture's protocol. One microliter of genomic DNA was used for PCR reactions.

Figure 2:
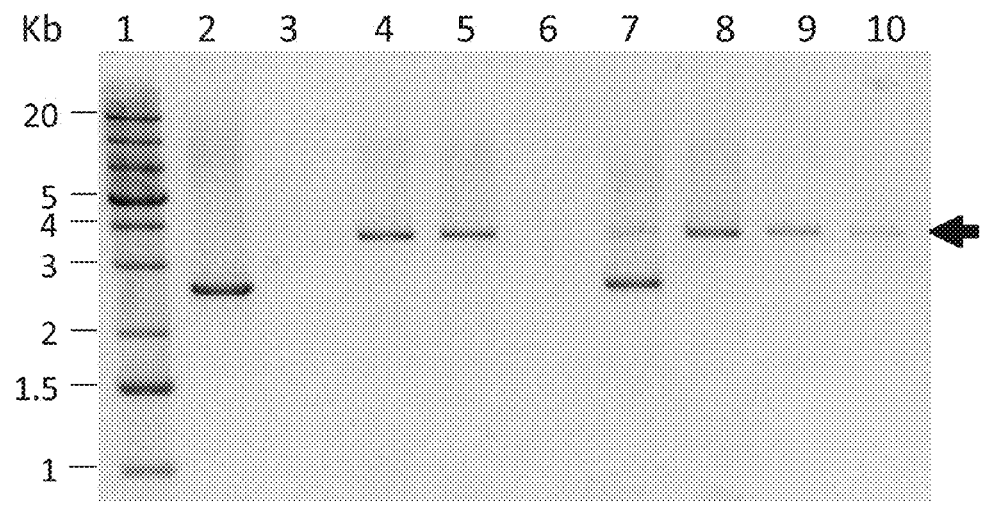
FIG. 2 depicts the PCR verification of deletion of the ptaB gene from *T. reesei* transformants A—Agarose gel of PCR amplification products using ptaB promoter and terminator specific primers and genomic DNA isolated from parental M2C38aux strain (lane 2) and putative PtaB deletion strains (lanes 4-10). Lane 3 was left empty. DNA size markers (Fermentas 1 kb plus ladder) were loaded on lane 1. The size of each DNA marker fragment is indicated on the left. The bands corresponding to the fragments with expected size for ptaB deletion are shown with black arrow on the right. B—Scheme of genomic ptaB locus in strains containing ptaB deletion (top) and intact ptaB locus (bottom). PptaB—ptaB promoter and 5' flanking sequences, TptaB—ptaB terminator and 3' flanking sequences, ptaB—PtaB protein coding sequence, ura3—fungal selection marker cassette encoding *T. reesei* orotidine-5'-monophosphate decarboxylase. Primers used for PCR amplification are indicated with line arrows at their hybridization sites; PCR products are indicated with dotted lines and size of each fragment is indicated on the top of each line.
Figure 2:
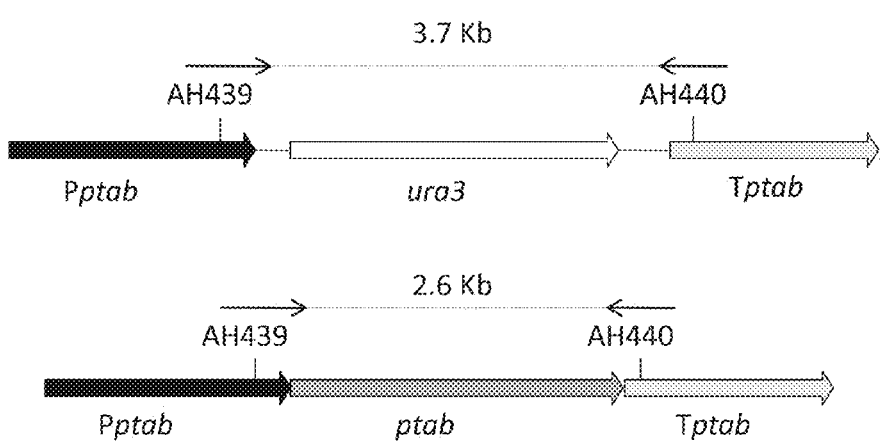

Initially, PCR analysis of the genomic DNA isolated from filamentous fungi transformants was used to identify if the deletion cassette integrated into ptaB locus. The PCR was performed using pair of primers, forward—AH439 GATGATGGCTACGAGTATGG (SEQ ID NO: 23), reverse—AH440 GGGAATCGAGCAAGTAAGAG (SEQ ID NO: 24), and iProof® High Fidelity DNA polymerase (Bio-Rad). The PCR was performed in 30 cycles with an annealing temperature of 62° C. and 110 seconds of extension time. Positive transformants (deletion of the native ptaB gene) were identified by an amplification of a 3.7 Kb product (FIG. 2). Negative transformants (contain native ptaB gene) were identified by amplification of a 2.6 Kb product. No 3.7 Kb PCR products were detected for the parent strain M2C38aux (FIG. 2). Five PtaB deletion strains were identified and selected for confirmation of deletion by Southern blotting. Probe for Southern blotting was synthesized and labeled using PCR DIG Probe Synthesis Kit (Roche, Cat #11 636 090 910) and primers, forward—AC956 CTCTCGATGATGCGTGTAAG (SEQ ID NO: 19) and reverse—AC957 CCATACTCGTAGCCATCATC (SEQ ID NO: 20). PCR reaction was performed following manufacture's recommendation with annealing temperature of 58° C. and extension time of 80 seconds. Synthesized 1966 bp PCR product, homologous to by −1993 to by −27 upstream of the ptaB start codon, was purified using Wizard® SV Gel and PCR clean-up System (Promega). For Southern blotting, genomic DNA isolated from putative PtaB deletion strains and their parental strain M2C38 was digested with SalI restriction enzyme and separated by agarose gel electrophoresis. The transformation vector was loaded on the gel as a control. The capillary DNA transfer to positively charged nylon membrane, hybridization of probe to target using DIG Easy Hyb buffer (Roche Cat #11 603 558 001) and detection of probe-target hybrids using NBT/BCIP (Roche Cat. #11 681 451 001) were performed as described in "DIG Application Manual" (Roche). The hybridization temperature was 68° C., two low stringency washes after hybridization were performed using 2×SSC containing 0.1% SDS at room temperature for 5 min and two high stringency washes were performed in 0.5×SSC containing 0.1% SDS at 68° C. for 15 min. The Southern blotting confirmed that all transformants selected by PCR analysis contain deletion of ptaB.

Example 5: Production of Biomass-Degrading Enzymes from Isolated and Parental Fungal Cells

*Trichoderma* spores from frozen (−80° C.) 15% glycerol stocks of strain M2C38 and a selected ptaB deletion strain, were inoculated onto standard 85 mm Petri plates containing potato dextrose agar (PDA). These plates were incubated at 28° C. for 5 days to achieve a confluent growth of fresh spores. To prepare the inoculum for fermentation testing, spores from a single PDA plate were transferred to a 2 L, baffled Erlenmeyer flask containing 750 mL of liquid Berkley media (pH 5.5) supplemented with 5.1 g/L of corn steep liquor powder and 10 g/L glucose. Flasks were incubated at 28° C. for 3 days using an orbital agitator (Model G-52 New Brunswick Scientific Co.) running at 100 rpm.

| Berkley Media, for Flasks | |
|---|---|
| Component | g/L |
| $(NH_4)_2SO_4$ | 10.4 |
| $KH_2PO_4$ | 2.0 |
| $MgSO_4 \cdot 7H_2O$ | 0.31 |
| $CaCl_2 \cdot 2H_2O$ | 0.53 |
| Dry Corn Steep Liquor | 5.1 |
| Glucose | 10 |
| Trace elements* | 1 mL/L |

*Trace elements solution contains 5 g/L $FeSO_4 \cdot 7H_2O$; 1.6 g/L $MnSO_4 \cdot H_2O$; 1.4 g/L $ZnSO_4 \cdot 7H_2O$.

The contents of an inoculum flask were transferred to a 14 L pilot scale fermentation vessel (Model MF114 New Brunswick Scientific Co.) set up with 10 L of Initial Pilot Media (pH 5.5). The vessel was run in batch mode until glucose in the media was depleted. At this point, the feed solution containing cellulase inducing carbohydrate as the carbon source was added at a carbon addition rate (CAR) of either 0.4 g of carbon per liter per hour or 1.0 g per liter of culture per hour. Peristaltic pumps were used to deliver the carbon source at a feed at a rate of 0.4 grams of carbon per liter culture per hour. Operational parameters during both the batch and fed-batch portions of the run were: mixing by impeller agitation at 500 rpm, air sparging at 8 standard liters per minute, and a temperature of 28° C. Culture pH was maintained at 4.0-4.5 during batch growth and pH 3.5 during cellulase production using an automated controller connected to an online pH probe and a pump enabling the addition of a 10% ammonium hydroxide solution. Periodically, 100 mL samples of broth were drawn for biomass and protein analysis. The total fermentation time typically is 168 hours; however for fermentations conducted at a CAR of 0.4 g of carbon per liter per hour, the total fermentation time was extended to 216 hours.

| Initial Media for Fed-Batch Fermentations | |
|---|---|
| Component | g/L |
| $(NH_4)_2SO_4$ | 2.20 |
| $KH_2PO_4$ | 1.39 |
| $MgSO_4 \cdot 7H_2O$ | 0.70 |
| $CaCl_2 \cdot 2H_2O$ | 0.185 |
| Dry Corn Steep Liquor | 6.00 |
| Glucose | 13.00 |
| Trace elements* | 0.38 mL/L |

*Trace elements solution contains 5 g/L $FeSO_4 \cdot 7H_2O$; 1.6 g/L $MnSO_4 \cdot H_2O$; 1.4 g/L $ZnSO_4 \cdot 7H_2O$.

The biomass content of the culture broth was determined using aliquots of 5-10 mL that had been weighed, vacuum filtered through glass microfiber filters, and oven dried at 100° C. for 4 to 24 hours. The concentration of biomass was determined according to the equation below.

$$\text{Biomass(g/L)} = \frac{\text{dry filter paper and cake(g)} - \text{filter mass(g)}}{\text{wet sample mass(g)}} \times \text{broth density(g/mL)} \times 1000(\text{mL/L})$$

The protein concentration of culture filtrate was determined using the Bradford assay. Colour intensity changes in the Coomassie Brilliant Blue G-250 dye, that forms the basis of this assay, were quantified spectrophotometrically using absorbance measurements at 595 nm. The standard assay control used was a cellulase mixture of known composition and concentration. The specific productivity, $q_p$, was expressed as mg protein produced per gram of biomass per hour of fermentation.

Figure 3:
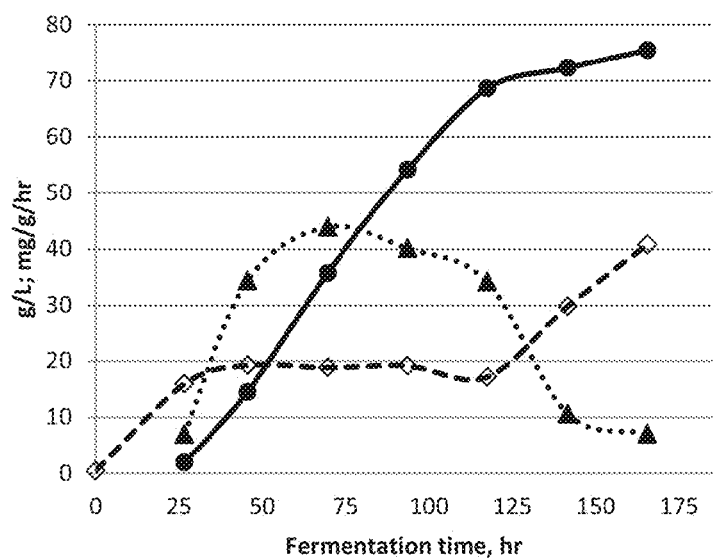
FIG. 3 shows pilot fermentation profiles of a ptaB deletion strain (A) and its parental strain (B). Fed-batch fermentations were performed as described in Example 5 with a carbon addition rate of about 1 g of carbon per liter per hour. Accumulation of biomass (dashed lines, open symbols) and total protein (solid lines, close symbols) were measured every 24 h after fermentation start. Specific productivity (dotted lines and closed triangles) was measured as mg of secreted protein produced per gram of biomass per h.
Figure 3:
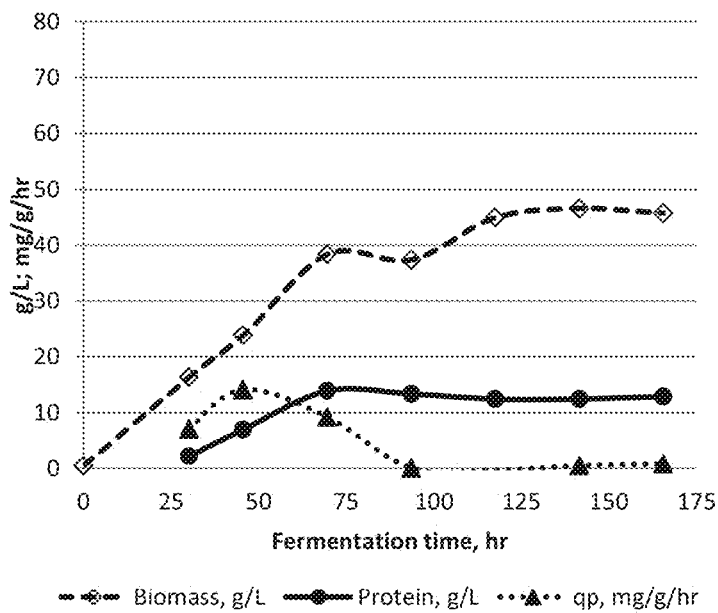
Figure 4:
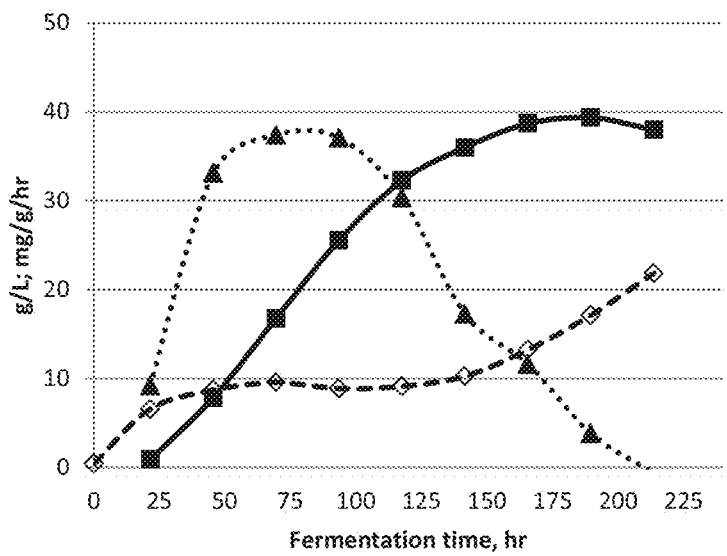
FIG. 4 shows pilot fermentation profiles of ptaB deletion strain (A) and its parental strain (B). Fed-batch fermentations were performed as described in Example 5 with a carbon addition rate of ~0.4 g of carbon per liter per hour. Accumulation of biomass (dotted lines, open diamonds) and total protein (solid lines, closed circles) were measured every 24 h after fermentation start. Specific productivity (dotted lines and closed triangles) was measured mg of protein produced per g of fungal cells per h.
Figure 4:
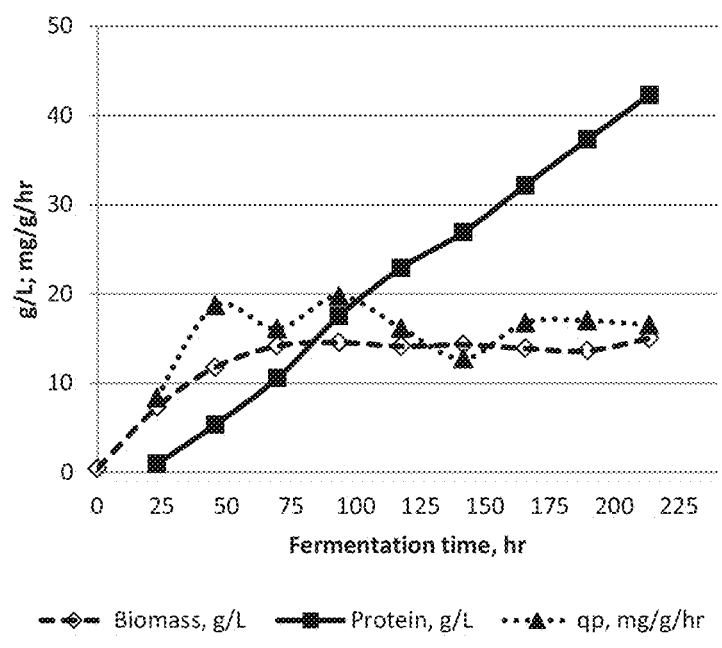

The fermentation profiles of a *Trichoderma reesei* PtaB deletion strain and its parental strain M2C38 grown at CAR of 1.0 and ~0.4 g carbon/L/h are shown in FIGS. 3 and 4, respectively. At the 168 hr fermentation time, the PtaB deletion strain produced 82.9% and 16.8% more of total protein, respectively, compared to that of its parental strain M2C38. In addition, the fermentation of the parental strain M2C38 conducted at a CAR of 0.4 g of carbon per liter per hour exhibited a higher sustainability productivity during extended fermentation run.

Example 6: Evaluation cel-Phenotype in Fungal Cell Populations

Since specific productivity of P1587AD transformant at the end of fermentation significantly decreased, the ability of cells collected at 168 h from fermentation start to produce cellulases was tested by plating on acid swollen cellulose plates. Preparation of phosphoric acid swollen cellulose (ASC) was conducted as follows. 400 g of SIGMACel T50 was wetted with 600 mL of acetone and mixed thoroughly with a paddle mixer in a 20 L bucket. The bucket content was then cooled in an ice water bath. A total of 4 L of commercial grade phosphoric acid (85%) was slowly added to the wetted cellulose and the suspension constantly stirred. Precooled deionized water was added to the acid/cellulose gelatinous mixture resulting in precipitation of a white clumpy material. A solution of 5-7% bicarbonate was added to begin neutralizing the slurry. The solution was slowly added to the slurry with constant mixing. Once the slurry pH is 5-7, it can be filtered through GF/A filter paper by vacuum filtration. The moist white cellulose preparation was washed with greater than 4 L of deionized water to ensure salts, and soluble sugars were removed from the resulting amorphous cellulose. Typical solids content of the cellulose after acid treatment is 7-9%. Further ASC was homogenized using the Powergen 1000 homogenizer (Fisher Scientific), diluted with an equal volume of water and pH adjusted to 4.5-4.6 before blending for 1 minute in a standard kitchen blender followed by sterilizing in the autoclave at standard temperatures and pressures. At this point the concentration of ASC is 25 g/L.

Figure 5:
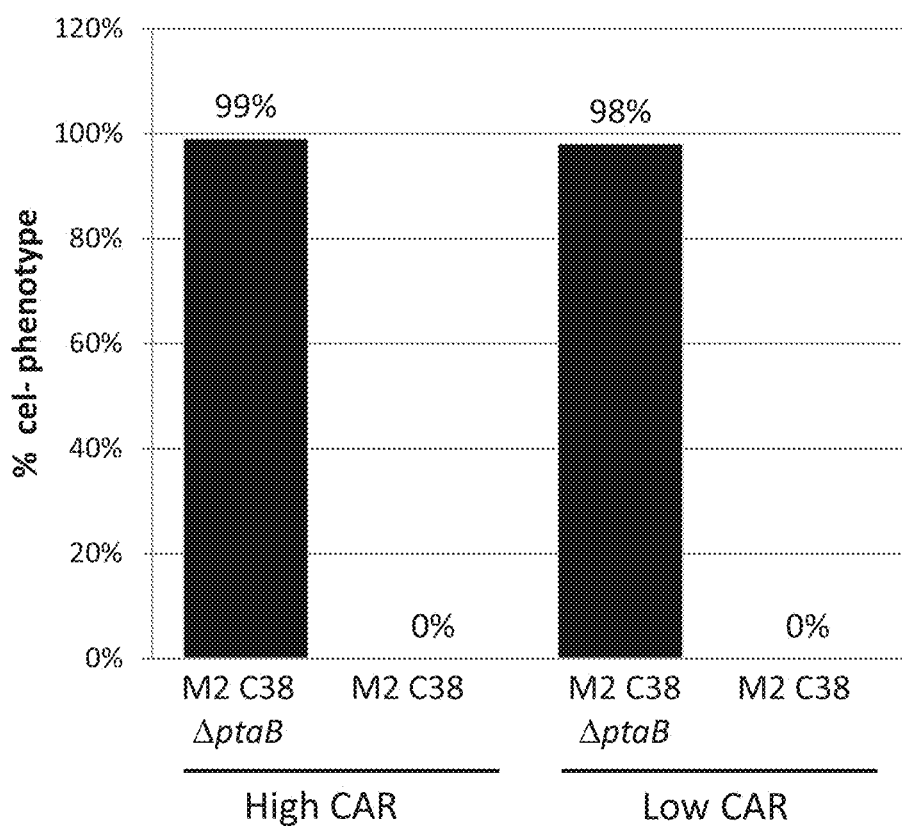
FIG. 5 shows the accumulation of cellulase non-producing (cel-) phenotype at the end of fed-batch fermentations of ptaB deletion strain and its parental strain. Biomass samples were collected after 165 h from fermentation start. Cellulase production phenotype was assessed as described in Example 6.

Biomass samples were collected at 168 hours from fermentation start, plated on PDA plates and incubated at 30° C. for 5 days to allow sporulation. The spores were washed from PDA plates with sterile water and about 50-100 spores were spread on ASC-minimal media containing 10 g/L of ASC and 7 g/L of Oxgall. ASC plates were incubated at 30° C. for 6 days, and transferred to 50° C. for 20 h. Cellulase secretion by individual colonies was assessed by formation of clearing zone around colonies. The non-producing colonies were counted; the proportion in total cell population was calculated and is presented in FIG. 5. The deletion of ptaB resulted in high population of cellulase non-producing phenotypes developed at the end of fermentation.

| Component | Amount per liter of media |
| --- | --- |
| 5X Minimal Media Salts* | 40 mL |
| Proteose Peptone#3 (Difco ™) | 0.2 g |
| Bovine Oxgall (Difco ™) | 1.8 g |
| Agar | 4 g |
| Deionzed water | 80 mL |
| Phosphoric Acid Swollen Cellulose (25 g/L) | 80 mL |
| 1M MgSO$_4$•7H$_2$O | 4 mL |

*ASC-Minimal Media Composition

| Component | Amount per liter of media |
| --- | --- |
| KH$_2$PO$_4$ | 50 g |
| (NH$_4$)$_2$SO$_4$ | 30 g |
| Na$_3$-Citrate•2H$_2$O | 15 g |
| FeSO$_4$•7H$_2$0 | 25 mg |
| MnSO$_4$•H$_2$O | 8 mg |
| ZnSO$_4$•7H$_2$O | 7 mg |
| CaCl$_2$•2H$_2$O | 10 mg |

*5X Minimal Media Salts Composition

Example 7: Overexpression of PtaB in *Trichoderma reesei*

Example 7.1: Generation of PtaB-Like Protein Overexpressing Transformants

Figure 6:
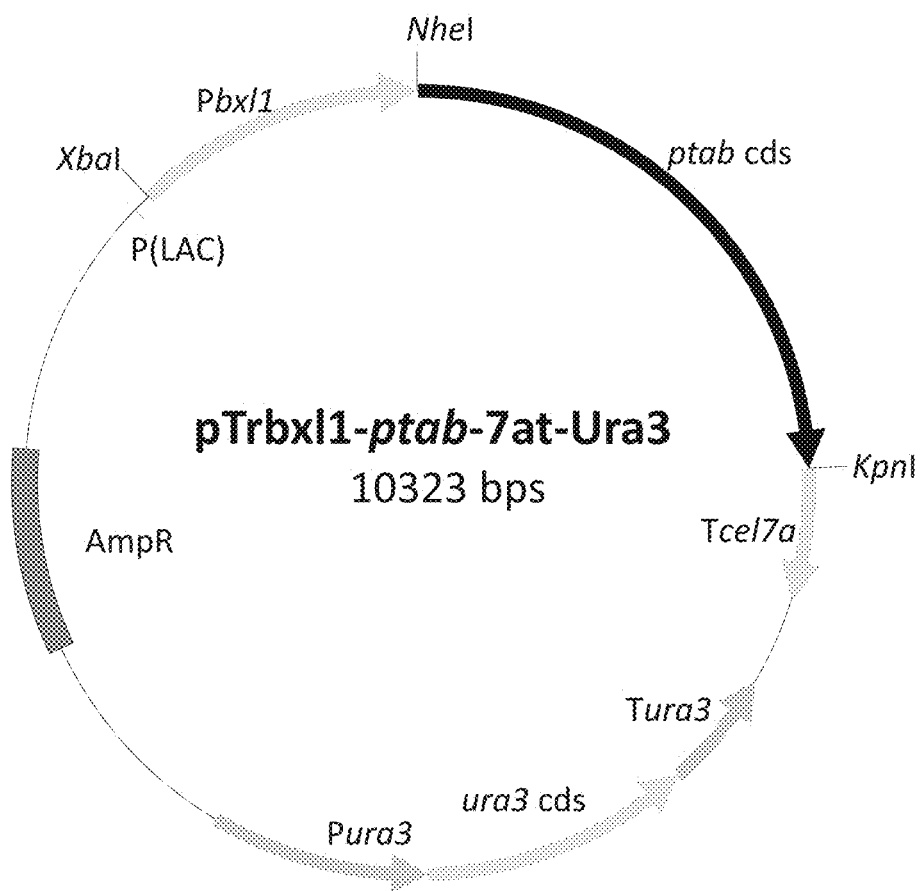
FIG. 6 shows a map of pTrbxl1-ptaB-7at-ura3 vector containing ptaB overexpression cassette. Pbxl1—bxl1 promoter; Tcel7a—cel7a terminator, ptaB cds—PtaB coding sequence; Pura3, ura3 cds, Tura3—fungal selection marker cassette encoding *T. reesei* orotidine-5'-monophosphate decarboxylase (promoter, coding sequence and terminator, respectively); AmpR—resistance to ampicillin conferring bacterial selection marker.

PtaB encoding polynucleotides were PCR amplified from genomic DNA isolated from *T. reesei* strain QM6a. Pair of primers, forward AC671 5'-TTGCTAGCATGGGACATC-CTGGAGTTG-3' (SEQ ID NO: 25) and reverse—AC683 5'-TTGGTACCTCAGGCCGGGTTGCCCTTCATTC-3' (SEQ ID NO: 26), was used to introduced NheI and KpnI sites required for cloning into transformation vector pTrBxl1p-NheI-KpnI-Tr7at-Ura3. This vector contains *T. reesei* ura3 gene as selection marker for *Trichoderma* transformation and cassette for expression of gene of interest. The amplified fragment was cloned into pJET vector (Fermentas). The coding sequence then was digested out of pJET with NheI/KpnI restriction enzymes and ligated into the same sites of pTrBxl1p-NheI-KpnI-Tr7at-Ura3, between beta-xylosidase (bxl) promoter and cellobiohydrolase I (cel7a) terminator. The generated *T. reesei* transformation vector pTrBxl1p-ptaB-Tr7at-Ura3 (FIG. 6) was used for transformation of BTR213aux strain.

The transformation was performed by biolistic gold particle bombardment using PDS-1000/He system with Hepta adapter (Bio-Rad; E.I. DuPont de Nemours and Company). Gold particles (median diameter of 0.6 um, Bio-Rad Cat. No. 1652262) were used as microcarriers. Prior transformation *T. reesei* was grown on potato dextrose agar (PDA) (Difco™) plates for 4-5 days at 30° C. until sporulated. Spores were suspended in sterile water. About 3.5×10$^8$ of spores was plated on 100 mm diameter plates containing minimal media (MM). The following parameters were used for the transformation: a rupture pressure of 1350 psi, a helium pressure of 28 mm Hg, target distance 3 cm. After particle delivery spores from each transformation plate were washed off with 2.5 mL of sterile 0.9% NaCl, spread on 3-4 150 mm plates containing MM (described in Example 3) and incubated at 30° C. for 5-10 days. All transformants were transferred to PDA media and incubated at 30° C. until sporulation.

Example 7.2: Screening of PtaB-Like Protein Overexpressing Transformants on ASC Plates Phosphoric acid swollen cellulose (ASC) was prepared and assessment of cellulase production by 29 *Trichoderma* transformants overexpressing the PtaB-like protein was performed as described in Example 6. The largest clearing zone-producing transformant was selected for further characterization in 14 L pilot fermentations.

Example 7.3: Analysis of PtaB Overexpressing Strains in 14 L Pilot Fermentations All pilot fermentations of parental strain BTR213 and PtaB overexpression strain were performed as described in example 5. For induction of the beta-xylosidase promoter directing expression of the PtaB-like protein, a mixture of 25 wt % xylose and 75 wt % CIC was used as the carbon source. Fermentation profiles of both strains grown in high (1.0) and low (0.4) CAR conditions are shown in FIGS. 7 and 8. In high CAR conditions (CAR 1.0 g carbon per liter per h) PtaB overexpression strain produced about 35% less of total protein and about 75% more of biomass compared to parental strain. Both strain show a similar drop in specific productivity at the end of fermentation. In contrast, at a CAR of 0.4 g carbon per liter per h, the fermentation using the PtaB overexpression strain sustained its specific productivity until the end of fermentation while maintaining the same level of protein productivity as parental strain (FIG. 8).

The accumulation of non-cellulase producing phenotype at the end of fermentations was evaluated as described in example 6. The accumulation of non-cellulase producing phenotype in BTR213 strain fermentation reached almost 40%, while all of the cells in fermentation with the PtaB overexpressing strain were still producing cellulases at the end of fermentation (FIG. 9).

The invention claimed is:

1. An isolated fungal cell capable of producing one or more biomass-degrading enzyme, comprising a decrease in copy number or expression, relative to a parental fungal cell from which the isolated fungal cell is derived, of a polynucleotide that encodes a polypeptide exhibiting from about 50% to 100% identity to SEQ ID NO: 1 or from about 60% to about 100% identity to the amino acid sequence of SEQ ID NO: 3, SEQ NO: 4, SEQ NO: 5, SEQ ID NO: 7, SEQ NO: 9, SEQ NO: 11, or SEQ ID NO: 14, wherein
(a) the fungal cell is a species of *Trichoderma, Hypocrea, Aspergillus, Fusarium, Penicillum, Chaetomium, Acremonium, Glomerella, Myceliophthora, Sporotrichum, Thielavia, Chrysosporium, Corynascus, Ctenomyces, Vertucillium, Cordyceps, Nectria,* or *Magnaporthe* and
(b) the fungal cell, when cultured in a fed-batch or continuous culture fermentation provided with a feed solution comprising a carbon source, exhibits at least about a 50% increase in maximal specific productivity ($q_p$) relative to a parental fungal cell from which the isolated fungal cell is derived cultured under the same conditions.

2. The fungal cell of claim 1, wherein the polypeptide exhibits from about 60% to about 100% identity to the amino acid sequence of SEQ ID NO: 1, SEQ ID NO: 3, SEQ ID NO: 4, SEQ ID NO: 5, SEQ ID NO: 7, or SEQ ID NO: 9.

3. The fungal cell of claim 2, wherein the one or more biomass-degrading enzyme is selected from the group consisting of a cellulase, a cellobiohydrolase, an endoglucanase, a beta-glucosidase, a cellulase-enhancing, protein, a xylanase, a beta xylosidase, an alpha-arabinofuranosidase, a beta-mannanase, an alpha-glucuronidase, an acetyl xylan esterase, a ferulic acid esterase, a lignin-degrading enzyme, and a combination thereof.

4. The fungal cell of claim 3, wherein at least one of the one or more biomass-degrading enzymes is endogenous to the fungal cell.

5. The fungal cell of claim 3, wherein at least one of the one or more biomass-degrading enzymes is heterologous to the fungal cell.

6. The fungal cell of claim 1, wherein the fungal cell is *T. reesei, jecorina, A. niger, A. fumigatus, A. orzyae, A. nidulans, F. oxysporum, C. thermophilum, A. thermophilum, G. graminicola, thermophila, thermophile, T. terrestris, T. heterothallica, C. thermophile, V. dahlia, C. militaris, N. heamatococca,* or *M. orzyae.*

7. A fermentation process for the production of one or more biomass-degrading enzyme, said process comprising:
(a) providing the isolated fungal cell of claim 1;
(b) culturing the isolated fungal cell in a submerged liquid fed-batch or continuous culture; and
(c) providing the fed-batch or continuous culture with a feed solution comprising a carbon source,
wherein the process is characterized by having at least about a 50% increase in maximal specific productivity ($q_p$) relative to an equivalent process utilizing a parental fungal cell from which the isolated fungal cell is derived.

8. The fermentation process of claim 7, wherein the carbon addition rate is at least 0.8 grams of carbon per liter per hour.

9. The fermentation process of claim 7 or 8, wherein the step of culturing is provided with feed solution comprising a carbon source consisting of:
(a) one or more cellulase-inducing carbohydrate;
(b) one or more hemicellulose-derived carbohydrate;
(c) one or more non-inducing carbohydrate;
(d) a mixture of (a) and (b);
(e) a mixture of (a) and (c);
(f) a mixture of (b) and (c); or
(g) a mixture of (a), (b) and (c).

10. The fermentation process of claim 9, wherein
(a) the cellulase-inducing carbohydrate is selected from the group consisting of cellulose, lactose, cellobiose, sophorose, gentiobiose, and a combination thereof;
(b) the hemicellulose-derived carbohydrate is selected from the group consisting of xylan, arabinoxylan, xylo-oligosaccharides, arabinoxylo-oligosaccharides, D-xylose, xylobiose, L-arabinose, D-mannose, D-galactose, and combinations thereof; and
(c) the non-inducing carbohydrate is selected from the group consisting of: glucose, dextrose, sucrose, molasses, fructose, glycerol, one or more organic acid, and any combination thereof.

11. An isolated fungal cell capable of producing one or more biomass-degrading enzyme, comprising a decrease in copy number or expression, relative to a parental fungal cell from which the isolated fungal cell is derived, of a polynucleotide that hybridizes under at least high stringency conditions to any one of (i) the polypeptide coding sequence of SEQ ID NO; 2, (ii) a genomic DNA sequence comprising the polypeptide coding sequence of SEQ ID NO: 2, and (iii) a full-length complementary strand of (i) or (ii), wherein high stringency conditions are prehybridization and hybridization at 42° C. for 12 to 24 hours in 5×SSPE, 0.3% SD5, 200 µg/mL sheared and denatured salmon sperm DNA, and 50% formamide followed by post-hybridization washes of three times each for 15 minutes using 2×SSC, 0.2% SDS at 65° C., wherein the fungal cell, when cultured in a fed-batch or continuous culture fermentation provided with a feed solution comprising a carbon source, exhibits at least about a 50% increase in maximal specific productivity ($q_p$) relative to a parental fungal cell from which the isolated fungal cell is derived cultured under the same conditions.

* * * * *

SEQUENCE LISTING

```
<160> NUMBER OF SEQ ID NOS: 27

<210> SEQ ID NO 1
<211> LENGTH: 720
<212> TYPE: PRT
<213> ORGANISM: Trichoderma reesei

<400> SEQUENCE: 1

Met Gly His Pro Gly Val Ala Gly His Pro Met Gly Ala Pro Gly Met
1               5                   10                  15

Pro Pro Asn Ala Gly Gln Gln Gly Ala Pro Gly Gly Met Pro His Gln
            20                  25                  30

Phe Ala Gly Gly His Ile Ala Val Ser Gly Pro Gly Gly Gln Val Asn
        35                  40                  45

Pro Ala Met Met Gly Gly Met Pro Pro Gly Ala Ser Pro Gly Pro His
    50                  55                  60

Ala Val His Gln Leu Thr Pro Ala Gln Gln Met Phe Gln Gln Gln
65                  70                  75                  80

Gln Gln His Leu Gln Gln Gln Phe Ser Met Asn Asn Pro Ser Ala Met
                85                  90                  95

Ala Ala Ile Arg Gln Gln Gln Ile Leu Gln Gln Gln Gln Arg Gln Ala
            100                 105                 110

Met Phe Ala Gln Gln Phe Gln Gly Met Asn Thr Ala Gly Val Asn Gly
        115                 120                 125

Leu Pro Met Gly Met Gln Leu Ser Pro Gln Gln Leu Gln His Leu Arg
    130                 135                 140

Gln Arg Ser Ala Ala Met Ser His Val Ala Gly Pro Asn Ser Gln Ala
145                 150                 155                 160

Ile Met Ala Gln Gln Leu Ala Leu Gln Gln His Ala Ala Ala Gln Gln
                165                 170                 175

Gln Ala Ala Gln Gln Ala His His Gln Ala Ala Ala Gln Gln Ala Ala
            180                 185                 190

Gln Gln Gln Val Ala His Asn Gln Leu Ala Ala Ser His Asn Gln
        195                 200                 205

Ala Gln His Met Ala Met Asn Ala Gln Pro Met Gly Met Gln Gln Gln
    210                 215                 220

Asn Pro Met Ala Ala Ala Gln Thr Gln Met Ala Ala Gln Gln Pro
225                 230                 235                 240

Gln Asn Gln Gln Pro Pro Gly Gln Pro Gln Pro Gln Gln Gln Gln
                245                 250                 255
```

-continued

```
Pro Gly Pro Gln Ser Gln Gln Ala Pro Gln Gln Thr Ser Gln Ala Gly
            260                 265                 270

Thr Pro Ala Pro Ser Gly Gln Gln Thr Pro Ser Gln Thr Pro Ala Pro
        275                 280                 285

Thr Pro Ala His Ala Asn Gln Met Pro Pro Gly Gln Pro Gln Pro Gln
    290                 295                 300

Gln Ala Gln Pro Pro Asn Gln Ala Gln Met Ala Ala Gln Gln Leu Met
305                 310                 315                 320

Ala Ser Ser Met Met Gln Gln Gln Met Arg Glu Gly Met Lys Thr
                325                 330                 335

Arg Cys Leu Leu Lys Leu Met Gln Phe Gly Glu Arg Leu Ser Gly Phe
            340                 345                 350

Pro Gly Ala Lys Asn Lys Asp Asp Met Ser Tyr Trp Asn Arg Phe Val
        355                 360                 365

Ala Gln Phe Phe Ser Pro Asn Gly Val Phe Arg His Thr Leu His Val
    370                 375                 380

Ser Asp Ser Glu Asp Thr Pro Asp Lys Gln Tyr Asp Ile Ser Tyr Pro
385                 390                 395                 400

Ala Ile Ala Arg Tyr Phe His Thr His Phe Ser Ser Gly Val Lys Ser
            405                 410                 415

Met Gln Leu Ile Leu Asp Ser Gly Ser Ser Asp Lys His Leu Pro Gly
        420                 425                 430

Asp Cys Tyr Cys Ile Glu Asn Pro Arg Ala Ser Phe Val Tyr Trp Phe
    435                 440                 445

Glu Thr Gly Ser His Leu Val Ala Thr Gly Thr Leu Arg Ala Gln Phe
450                 455                 460

Asp Ala Glu Gln Lys Ile Glu Leu Phe Glu Phe Leu Thr Thr Arg Gln
465                 470                 475                 480

Glu Glu Tyr Val Ser Arg Lys Arg Val Ile Glu Ala Ala Lys Pro Ala
            485                 490                 495

His Glu Trp Ile Lys Glu Trp Arg Ser Val Asn Thr Met Asp Gly Lys
        500                 505                 510

Gln Ser Pro Glu Met Ser Lys Lys Gly Lys Ala Arg Gln Leu Lys Ser
    515                 520                 525

Pro Gln Lys Glu Pro Pro Gly Val Leu Val Asp Leu Pro Asp Ser Ala
530                 535                 540

Val Asn Ser Lys Gly Val Thr Glu Ala Val His Gln Phe Leu Glu Ile
545                 550                 555                 560

Val Glu Val Met Gly Gln Met Asn Pro Leu Phe Gly Phe Phe His Ser
            565                 570                 575

Asn Pro Gly Leu Ser Pro Tyr Gly Ala Leu Glu Gln Tyr Val Ala Thr
        580                 585                 590

Gln Ile Asn Asn Asn Pro Ala Pro Met Met Asn Gly Gln Thr Met Gly
    595                 600                 605

Gln Gly Pro Arg Thr Pro Ser Phe Gly Gln Phe Pro Met Gly Ala Ser
610                 615                 620

Pro Ala Ala Val His Met Asn Leu Pro Gly Ser Pro His Ile Gly Ser
625                 630                 635                 640

Pro Ala Pro Gly Gln Ala Pro Gly Met Gln Leu Gln Pro Ser Gln Gln
            645                 650                 655

Gly Thr Ser Ser Ser Gly Pro Ser Ala Asn Thr Ser Pro Ala Ser Asn
        660                 665                 670

Lys Arg Arg Arg Pro Ser Thr Val Lys Val Glu Asp Asp Ser Ala Thr
```

| | | 675 | | | 680 | | | 685 | | | |
|---|---|---|---|---|---|---|---|---|---|---|---|
| Ala | Gly | Gly | Thr | Gln | Val | Asn | Gly | Ile | Gln | Ser | Arg | Ala | Lys | Pro | Gln |
| | | 690 | | | | | 695 | | | | | 700 | | | |
| Pro | Gln | Thr | Thr | Pro | Arg | Met | Ala | Lys | Arg | Met | Lys | Gly | Asn | Pro | Ala |
| 705 | | | | 710 | | | | | 715 | | | | | 720 | |

<210> SEQ ID NO 2
<211> LENGTH: 2163
<212> TYPE: DNA
<213> ORGANISM: Trichoderma reesei
<400> SEQUENCE: 2

| | |
|---|---|
| atgggacatc ctggagttgc tgacatccc atgggggccc ccggaatgcc tcccaacgcc | 60 |
| ggccagcaag gcgcgcccgg cggcatgcct caccagttcg ctggcggcca catcgccgtc | 120 |
| tccggcccag gaggccaggt caatcccgcc atgatgggcg gtatgccgcc tggtgccagt | 180 |
| cctggcccctc acgcggtgca ccagctcacc cccgcgcaac agcagatgtt tcagcagcag | 240 |
| cagcagcatc tgcaacagca gttcagcatg aacaacccga gcgcaatggc tgccattcga | 300 |
| cagcaacaaa ttctgcaaca gcaacaacgg caagccatgt cgcccagca gtttcaaggc | 360 |
| atgaacaccg cgggcgtcaa cggtctaccc atgggcatgc aactgagccc ccagcagctt | 420 |
| cagcatctga cagcggag cgccgccatg agccatgtag ccgggcctaa ctcgcaggcg | 480 |
| atcatggcgc aacagctggc cctccagcag catgcggcgg cccagcagca agcagcccag | 540 |
| caagcgcatc atcaggccgc ggcgcaacag gcggcgcaac agcaggtggc gcataatcag | 600 |
| cagttggctg ccagccataa ccaggcgcag acatggcaa tgaacgcgca gcccatggga | 660 |
| atgcagcagc agaaccccat ggctgccgcg gctcagacgc agatggccgc ccagcaacca | 720 |
| cagaaccagc agcctccggg gcaacctcaa ccaccgcaac agcagcagcc tgggcccccag | 780 |
| tcacagcagg cccccagca gacctctcag gcaggcacac cagctccctc tggccagcag | 840 |
| acaccgtccc agacacccgc cccgacaccc gctcacgcga accagatgcc gcctggacaa | 900 |
| ccccagcccc agcaagctca ccccccgaac caggcccaga tggccgccca gcagctgatg | 960 |
| gcgtcgtcca tgatgcaaca gcagcagatg agggaaggga tgaagactcg gtgtctgttg | 1020 |
| aagttgatgc agtttggaga acgccttagc ggcttcccgg gcgcaaagaa caaggacgat | 1080 |
| atgtcctatt ggaatcgatt tgtagcccag ttcttctccc caaacggcgt gttccgacat | 1140 |
| acattacacg tcagcgactc cgaggacaca ccggacaagc agtacgatat ctcgtaccca | 1200 |
| gcgattgctc gctacttcca tacgcacttc agcagtggcg tcaagagcat gcagctcatt | 1260 |
| ctggatagcg ggagcagtga caagcatctg ccaggagact gctattgcat cgagaatccc | 1320 |
| agggccagct tcgtctactg gttcgagacg gctcacatcc tcgtggccac tggtacgtta | 1380 |
| cgggcgcaat tcgatgccga acaaaagatt gaactgttcg aattcctcac gacgagacaa | 1440 |
| gaggaatacg tttctcgaaa gcgagtgatt gaagctgcaa agccggcaca tgaatggatc | 1500 |
| aaggaatggc gcagcgtaaa tacgatggac ggcaagcagt cgccggaaat gtccaagaag | 1560 |
| ggcaaggctc gccagctcaa gtctcctcag aaagagcctc ctggggtttt ggtcgatctc | 1620 |
| ccggactctg cggtgaacag caagggcgtc acgaggcgg tacatcagtt cctcgagatt | 1680 |
| gtggaggtta tgggccagat gaacccattg tttggattct tccactccaa tcccggcctc | 1740 |
| agccccctatg gcgcgctcga acaatacgtt gcaacccaga tcaacaacaa cccggcaccc | 1800 |
| atgatgaacg ggcagaccat gggccagggg ccaaggacac tagtttttcgg gcagttcccg | 1860 |
| atgggagcga gccctgctgc ggtacacatg aacctcccgg ggtcgcctca catcggcagc | 1920 |

-continued

```
cctgcgccgg gccaagcccc cggcatgcag ctccagccta gccagcaagg gacgagctca    1980
agcgggccaa gcgcaaacac atcgccggct tctaataaac gtcggcgtcc gtccaccgtc    2040
aaggtcgaag acgattcggc cacagcaggc ggtactcagg tcaacggcat ccagagcagg    2100
gccaagcccc aacccagac tactcctcga atggccaagc gaatgaaggg caacccggcc     2160
tga                                                                   2163
```

<210> SEQ ID NO 3
<211> LENGTH: 743
<212> TYPE: PRT
<213> ORGANISM: Nectria heamatococca

<400> SEQUENCE: 3

```
Met Ala Thr Ser Met Gly Pro Asn Phe Ser Gly His Pro Ala Gly Met
1               5                   10                  15

Gly His Pro Gly Val Ala Gly His Pro Met Gly Pro Gly Met Pro His
            20                  25                  30

Asn Pro Gly Gln Gln Gly Ala Pro Asn Ala Gly Met Pro His Gln Phe
        35                  40                  45

Gly Gly Pro Met Val Ser Ala Pro Gly Ala Gln Val Asn Pro Ala Leu
    50                  55                  60

Met Gly Gly Met Pro Pro Gly Ala Asn Pro Asn Ala His Ala Leu Gln
65                  70                  75                  80

His Leu Asn Pro Ala Gln Gln Met Phe Gln Gln Gln Leu Gln
                85                  90                  95

His Phe Gly Asn Pro Gln Ala Ile Ala Ala Met Arg Gln Gln Leu
            100                 105                 110

Leu Gln His Gln Gln Ala Arg His Leu Met Ala Gln Gln Ala Phe
        115                 120                 125

Gln Ala Asn Met Ala Gln Gly Gly Met Pro Met Asn Met Ala Gln Met
    130                 135                 140

Asn Leu Asn Pro Gln Gln Leu His Gln Leu Arg Ala Ala Arg Met Gly
145                 150                 155                 160

Pro Gly Gln Gln His Pro Gln Ala Gln Ala Ile Met Ala Gln Gln Leu
                165                 170                 175

Ala Leu Gln Gln Gln His Gln Gln Gln Gln Gln Ala Ala His
            180                 185                 190

Ala Gln Gln Gln Met Gln Gln Gly Gly Pro Asn Pro Asn Gln Gln Met
        195                 200                 205

Gln Met Asn Ala Gln Asn Met Gln Thr Met Gln Gln Asn Gln Leu Ala
    210                 215                 220

Ala Ala Ser Leu Gln Asn Gln Met Ala Asn Gln Gln Gly Gln Gln Pro
225                 230                 235                 240

Gln Gly Gln Pro Gln Pro Gln Pro Gln Ser Gln Pro Gln Gln Pro Gly
                245                 250                 255

Gln Gln Pro Gln Gln Thr Pro Gln Gln Ser Ser Gln Ala Gly Thr Pro
            260                 265                 270

Ala Pro Thr Gly Pro Gln Thr Pro Ala Gln Thr Pro Asn Ser Thr Pro
        275                 280                 285

Ala Gln Pro Asn Gln Met Pro Pro Gly His Ser Gln Pro Gln Val Pro
    290                 295                 300

Gln Thr Pro Ala Gln Ser Gln Ala Gln Pro Gln Pro Gln Pro Gln Ala
305                 310                 315                 320
```

-continued

```
Gln Pro Gln Pro Gln Pro Gln Ala Pro Thr Pro Gln Gln Gln His Gln
                325                 330                 335

Met Asn Ala Ala Ala Gln Gln Leu Ala Ile Gln Asn Ser Met Met Gln
            340                 345                 350

Gln Gln Gln Arg Arg Asp Asn Met Lys Gly Gln Cys Leu Leu Lys Leu
        355                 360                 365

Met Gln Phe Ser Glu His Leu Ser Gly Tyr Pro Gly Ser Lys Gly Arg
370                 375                 380

Asp Asp Leu Ser Tyr Trp Asn Ala Phe Val Arg Phe Phe Ser Gln
385                 390                 395                 400

Asn Gly Val Phe Arg His Ser Leu His Ile Thr Asp Ala Glu Asp Thr
                405                 410                 415

Thr Asp Lys Gln Tyr Glu Ile Ala Tyr Pro Ala Ile Ala Arg Tyr Phe
            420                 425                 430

His Thr His Phe Gly Ser Gly Val Lys Asn Met Gln Leu Ile Met Asp
        435                 440                 445

Lys Gly Val Thr Asp Arg Pro Leu Pro Gly Asp Cys His Cys Ile Glu
    450                 455                 460

Asn Ser Lys Ala Ser Leu Val Tyr Trp Phe Glu Thr Gly Ser His Leu
465                 470                 475                 480

Val Ala Ser Gly Thr Leu Arg Ala Gln Phe Asp Ala Glu Gln Lys Ile
                485                 490                 495

Glu Leu Phe Glu Phe Leu Thr Thr Ser His Glu Glu Tyr Ile Ser Arg
            500                 505                 510

Lys Gln Val Ile Asp Ala Ala Lys Pro Ala His Met Trp Met Lys Glu
        515                 520                 525

Trp His Lys Thr Asn Ser Gln Asp Gly Lys Ser Pro Glu Leu Ser Lys
    530                 535                 540

Lys Gly Lys Gly Arg Gln Leu Lys Ser Pro Gln Thr Gln Pro Pro Glu
545                 550                 555                 560

Val Leu Val Asp Leu Pro Glu Ala Ala Val Asn Ser Lys Gly Val Thr
                565                 570                 575

Gln Ala Val Phe Gln Phe Leu Glu Ile Val Glu Val Met Gly Gln Met
            580                 585                 590

Asn Pro Leu Phe Gly Phe Phe His Ser Asn Pro Gly Leu Gly Pro Tyr
        595                 600                 605

Gln Ala Leu Glu Gln Tyr Val Ala Thr Gln Ile Asn Gly Val Pro Pro
    610                 615                 620

Thr Met Asn Gly Gln Pro Met Pro Pro Gly Ala Arg Thr Pro Ser Phe
625                 630                 635                 640

Gly Gln Phe Pro Met Gly Ala Ser Pro Ala Thr Ala His Met Asn Leu
                645                 650                 655

Pro Gly Ser Pro His Ile Gly Ser Pro Ala Pro Gly His Met Gln Ala
            660                 665                 670

Pro Gly Met Gln Met Gln Gln Ser Gln Gln Gly Thr Gly Ser Ser Gly
        675                 680                 685

Pro Ser Ala Asn Thr Ser Pro Ala Ser Asn Lys Arg Arg Arg Pro Ser
    690                 695                 700

Ala Val Lys Glu Glu Asp Gly Ser Gly Ala Pro Thr Pro Ala Thr Asn
705                 710                 715                 720

Gly Met Pro Arg Asn Ala Lys Pro Pro Thr Pro Arg Met Thr Lys Arg
                725                 730                 735

Leu Lys Gly Asn Pro Pro Ala
```

-continued

```
                        740

<210> SEQ ID NO 4
<211> LENGTH: 751
<212> TYPE: PRT
<213> ORGANISM: Fusarium oxysporum

<400> SEQUENCE: 4

Met Ala Thr Ser Met Gly Pro Asn Phe Ser Gly His Pro Ala Gly Met
1               5                   10                  15

Gly His Pro Gly Val Ala Gly His Pro Met Gly Pro Gly Gly Met Pro
            20                  25                  30

His Asn Pro Gly Gln Gln Gly Ala Pro Gly Gly Met Pro His Gln Phe
        35                  40                  45

Gly Gly Pro Met Val Ser Ala Pro Gly Ala Gln Val Asn Pro Ala Leu
    50                  55                  60

Met Gly Gly Met Pro Pro Gly Ala Asn Pro Asn Ala His Ala Leu Gln
65                  70                  75                  80

His Leu Asn Pro Thr Ala Gln Gln Met Leu Gln Gln Leu Gln
                85                  90                  95

Gln Gln His Phe Gly Asn Pro Gln Ala Met Ala Ala Met Arg Gln Gln
            100                 105                 110

Gln Gln His Leu Leu Gln Gln Gln Ala Arg Gln Leu Met Ala Gln
        115                 120                 125

Gln Ala Phe Gln Ala Asn Met Gln Gly Gly Ile Pro Met Asn Met
    130                 135                 140

Ala Gln Phe Ser Gln Leu Asn Pro Gln Gln Leu His Gln Leu Arg Arg
145                 150                 155                 160

Gly Leu Ala Pro His Pro Gln Ala Gln Ala Ile Met Ala Gln Gln Leu
                165                 170                 175

Ala Leu Gln Gln His Gln Ala Gln Gln Gln Gln Gln Gln Gln Gln
            180                 185                 190

Gln Gln Gln Gln Gln Gln Gln Val Ala His Ala Gln Gln Met Gln
        195                 200                 205

Ala Gly Pro Asn Pro Gly Gln Pro Met Pro Met Asn Ala Gln Ser Met
    210                 215                 220

Gln Ala Met Gln Gln Asn Gln Leu Ala Leu Gln Asn Gln Met Ala Asn
225                 230                 235                 240

Gln Gln Gly Gln Gln Pro Gln Gly Gln Pro Gln Pro Gln Pro Gln Pro
                245                 250                 255

Gln Gln Gln Gln Gln Pro Gly Gln Gln Gln Pro Gln His Thr Pro
            260                 265                 270

Gln Gln Ser Ser Gln Ala Gly Thr Pro Ala Pro Thr Gly Pro Gln Thr
        275                 280                 285

Pro Ala Gln Thr Pro Ser Ser Thr Pro Ala Gln Pro Ser Gln Leu Pro
    290                 295                 300

Pro Gly Gln Ser Gln Pro Gln Val Pro Gln Thr Pro Ala Gln Pro Gln
305                 310                 315                 320

Ala Gln Pro Gln Pro Gln Pro Gln Ala Gln Ala Gln Pro Gln Pro Gln
                325                 330                 335

Ala Gln Pro Gln Gln His Gln Met Ser Ala Thr Thr Ala Gln Gln Leu
            340                 345                 350

Ala Ile Gln Ser Gln Ile Leu Gln Gln Gln Arg Arg Asp Ser Met Lys
        355                 360                 365
```

```
Gly Gln Cys Leu Leu Lys Leu Met Gln Phe Ser Glu His Leu Ser Gly
        370                 375                 380

Phe Pro Gly Ser Lys Gly Arg Asp Asp Leu Ser Tyr Trp His Gly Phe
385                 390                 395                 400

Val Met Arg Phe Phe Ser Pro Asn Gly Val Phe Arg His Ser Leu His
                405                 410                 415

Ile Thr Asp Ala Glu Asp Thr Thr Asp Lys Gln Tyr Glu Ile Ala Tyr
            420                 425                 430

Pro Ala Ile Ala Arg Tyr Phe His Thr His Phe Gly Ser Gly Val Lys
        435                 440                 445

Asn Met Gln Leu Ile Met Asp Lys Gly Val Thr Asp Arg Pro Leu Pro
450                 455                 460

Gly Asp Cys His Cys Ile Glu Asn Ser Lys Ala Ser Phe Val Tyr Trp
465                 470                 475                 480

Phe Glu Thr Gly Ser His Leu Val Ala Ser Gly Thr Leu Arg Ala Gln
                485                 490                 495

Phe Asp Ala Glu Gln Lys Ile Glu Leu Phe Glu Phe Leu Thr Thr Ser
                500                 505                 510

His Asp Glu Phe Ile Ser Arg Lys Gln Val Ile Asp Ala Ala Lys Pro
            515                 520                 525

Ala His Met Trp Met Lys Glu Trp His Lys Thr Asn Ser Gln Asp Gly
        530                 535                 540

Lys Ser Pro Glu Leu Ser Lys Gly Lys Gly Arg Gln Leu Lys Ser
545                 550                 555                 560

Pro Gln Thr Gln Pro Pro Glu Val Leu Val Asp Leu Pro Asp Ser Ala
                565                 570                 575

Val Asn Ser Lys Gly Val Thr Glu Ala Val Phe Gln Phe Leu Glu Ile
            580                 585                 590

Val Glu Val Met Gly Gln Met Asn Pro Leu Phe Gln Phe Tyr His Ser
        595                 600                 605

Asn Pro Gly Leu Gly Pro Tyr Gln Ala Leu Asp Gln Tyr Val Ser Thr
        610                 615                 620

Gln Ile Asn Gly Val Pro Pro Asn Met Asn Gly Gln Gln Met Pro Pro
625                 630                 635                 640

Gly Ala Arg Thr Pro Ser Phe Gly Gln Phe Pro Met Gly Ala Ser Pro
                645                 650                 655

Ala Ala Ala His Met Asn Leu Pro Gly Ser Pro His Met Gly Ser Pro
                660                 665                 670

Ala Pro Gly His Met Gln Ala Pro Gly Met Gln Met Gln Gln Ser Gln
            675                 680                 685

Gln Gly Thr Gly Ser Ser Gly Pro Ser Ala Asn Thr Ser Pro Ala Ser
        690                 695                 700

Asn Lys Arg Arg Arg Pro Ser Ala Val Lys Glu Glu Asp Gly Ser Gly
705                 710                 715                 720

Ala Pro Thr Pro Ala Ala Asn Gly Met Pro Arg Asn Ala Lys Pro Pro
                725                 730                 735

Thr Pro Arg Met Pro Lys Arg Leu Lys Gly Asn Pro Pro Ala Gln
            740                 745                 750
```

<210> SEQ ID NO 5
<211> LENGTH: 773
<212> TYPE: PRT
<213> ORGANISM: Glomerella graminocola

<400> SEQUENCE: 5

```
Met Thr Ser Met Gly Pro Ser Phe Ala Gly His Pro Ala Gly Met Gln
1               5                   10                  15

Gln His Pro Gly Val Pro Gly His Pro Met Ala Gln Gly Met Pro His
                20                  25                  30

Asn Pro Gly Gln Gln Gly Pro Pro Gly Gly Met Pro His Gln Met
            35                  40                  45

His Met Ala Val Ser Gly Pro Gly Gly Gln Val Asn Pro Asn Gln Leu
    50                  55                  60

Met Gly Gly Met Pro Pro Gly Ala Gly Gly Pro Asn Ala His Ala Leu
65              70                  75                      80

Gln His Leu Asn Pro Ala Gln Asn Pro Met Phe Gln Gln Asn Gln Phe
                85                  90                  95

Ala Asn Tyr Asn Asn Pro Ala Ala Met Ala His Ala Thr Gln Ile Ala
            100                 105                 110

Gln Gln Arg Leu Phe Gln Gln Gln Gln Ala Arg Gln Ala Leu Met
    115                 120                 125

Ala Gln Gln Ala Phe Asn Ala Asn Met Ala Gly Val Asn Gly Met Pro
    130                 135                 140

Met Gly Met Gln Met Asn Pro Met Asn Ala Ala Gln Leu Ala Ala Met
145                 150                 155                 160

Arg Gln Gly Met Arg Pro Gln Gly His Asn Pro Gln Ala Gln Ala Met
                165                 170                 175

Leu Ala Gln Gln Ile Ala Leu Gln Gln Gln Met Gln Gln Gln Gly
                180                 185                 190

Gln Gln Gln Gly Gln Pro Val Gln Met Asn Pro Gln His Met Gln Leu
    195                 200                 205

Gln Gln Ala Gln Leu Ala Ala Ser Leu Gln Ala Gln Gln Gln Gln
    210                 215                 220

Gln Gln Gln Gln Gln Gln Gln Ala Gln Gln Gln Gln Gln Gln Gln
225                 230                 235                 240

Gln Gln Ala Gln Gln Ala Gln Gln Gln Ala Gln Gln Gln
            245                 250                 255

Ala Gln Gln Gln Ala Gln Gln Gln Gln Gln Gln Gln Gln
                260                 265                 270

Gln Gln Gln Gln Gln Gln Gln Gln Gln Gly Gln Pro Gln Gly
            275                 280                 285

Gln Pro Gln Gln Pro Gln Pro Gln Pro Gln Gln Thr Pro His Gln Thr
    290                 295                 300

Pro Gln Gln Gln Pro Ala Gln Pro Val Asn Pro Gln Ser Ala Gly Gln
305                 310                 315                 320

Pro Thr Pro Ser Gln Thr Pro Gly Pro Ala Pro Asn Gln Gln Pro Gln
                325                 330                 335

Pro Pro Gln Ala Gln Ala Gln Pro Gln Gly Pro Pro Gln Met Ser Ala
            340                 345                 350

Gln Pro Gly Pro Gln Gln Met Asn Pro Ala Gln Gln Ala Ala Gln
            355                 360                 365

Ala Ala Val Ala Asn Asn Leu Ala Leu Ala Gln Gln Arg Arg Glu Gly
    370                 375                 380

Met Lys Gly His Cys Leu Leu Lys Leu Met Gln Phe Ser Glu His Leu
385                 390                 395                 400

Ser Gly Phe Pro Gly Ser Lys Gly Lys Asp Asp Leu Ser Tyr Trp Asn
                405                 410                 415
```

```
Ser Phe Val Asn Gln Phe Ser Thr Lys Gly Val Phe Arg His Ser
            420                 425                 430

Val His Ile Thr Asp Val Glu Asp Gln Ala Asp Lys Gln Tyr Glu Ile
        435                 440                 445

Thr Tyr Pro Ala Leu Pro Arg Tyr Phe His Thr His Phe Asp Ser Gly
    450                 455                 460

Val Lys Asn Met Gln Leu Ile Met Glu Lys Gly Thr Thr Asp Arg Pro
465                 470                 475                 480

Leu Pro Gly Asp Gly His Trp Ile Glu Asn Thr Lys Ser Ser Leu Val
                485                 490                 495

Tyr Trp Phe Glu Ser Gly Ser His Leu Val Ala Thr Gly Thr Val Arg
            500                 505                 510

Ala His Phe Asp Ala Glu Gln Lys Ile Glu Leu Phe Glu Phe Leu Thr
        515                 520                 525

Ser Asn His Glu Glu Tyr Ile Ser Arg Lys Ala Ala Ile Glu Ala Ala
    530                 535                 540

Lys Pro Ile His Asn Trp Val Lys Glu Trp His Lys Val Asn Ser Gln
545                 550                 555                 560

Asp Ser Lys Ala Ser Pro Glu Met Ser Lys Gly Lys Ala Arg Pro
                565                 570                 575

Met Lys Ser Pro Gln Asn Pro Pro Glu Ala Leu Val Asp Leu Pro
            580                 585                 590

Glu Ser Ala Val Lys Arg Gly Met Gly Val Thr Glu Ala Val Phe Gln
                595                 600                 605

Phe Leu Glu Ile Ala Glu Val Ile Gly Gln Met Asn Pro Leu Phe Ala
    610                 615                 620

Phe Tyr His Thr His Pro Asn Leu Gly Pro Tyr Ala Ala Leu Glu Gln
625                 630                 635                 640

Tyr Val Ser Gln Ile Asn Ala Val Pro Ala Asn Met Asn Gly Gln Pro
                645                 650                 655

Met Pro Gln Gly Pro Arg Thr Pro Ser Phe Gln Phe Pro Met Gly
            660                 665                 670

Ala Ser Pro Ala Gln Pro His Met Gln Leu Pro Gly Ser Pro His Val
    675                 680                 685

Gln Gly Ser Pro Ala Gln Gly His Met Gln Ala Pro Gly Met Gln Met
690                 695                 700

Gln Gln Ser Gln Gln Gly Thr Ser Ser Ser Gly Pro Ser Ala Asn Thr
705                 710                 715                 720

Ser Pro Ala Ser Asn Lys Arg Arg Pro Ser Gly Val Lys Met Glu
                725                 730                 735

Glu Asp Gly Ser Gln Ala Pro Thr Pro Gly Gly Pro Asn Val Asn Gly
            740                 745                 750

Val Gln Asn Lys Gly Lys Pro Pro Thr Pro Arg Met Ala Lys Arg Met
    755                 760                 765

Lys Gly Asn Pro Ala
    770

<210> SEQ ID NO 6
<211> LENGTH: 1093
<212> TYPE: PRT
<213> ORGANISM: Cordyceps militaris

<400> SEQUENCE: 6

Met Gly Leu Ser Gln Pro His Thr His Ala Pro Arg Ala Arg Ala Ala
1               5                   10                  15
```

-continued

His Pro Lys Thr Pro Phe Ala Gly Asp Leu Gly Ser Thr Thr Asp Pro
              20                  25                  30

Val Arg Gln Gly Lys Val Leu Ala Ser Gly Arg Lys Arg Glu Gly Arg
          35                  40                  45

Lys Gly Asp Gly Arg Ala Pro Thr Pro Gln Ser Pro Gln Ser Gly Pro
50                  55                  60

Pro Arg Ser Pro Ser Ser Arg Pro Ser Pro Ser Lys Glu Ser Leu His
65                  70                  75                  80

Glu Cys Tyr Leu Pro Leu Pro His Leu Phe Ser Ser Leu Ala Ser Pro
                  85                  90                  95

Leu Leu Leu Gly Pro Ser Leu Val Leu Val His Arg Gln Thr Pro Arg
              100                 105                 110

Thr Leu Gly Gly Thr Ala Ile Phe Thr Thr Ala Leu Leu Ala Pro Gly
              115                 120                 125

Ser Ala Arg Pro Thr Ser Pro Thr Leu Ser Pro Ala Leu Ala Ser Tyr
          130                 135                 140

Gly Cys Arg Ala Leu Pro Ser Ala Ser Ser Leu Arg Ala Ser Ser Arg
145                 150                 155                 160

Leu Leu Ala Ser Tyr Ser Ser Ser Leu Ser Gly His Arg Phe Leu Ala
                  165                 170                 175

Ile Arg Thr Arg Glu Pro Ser Trp Ser Trp Pro Gln Ala Ser Ser Ser
              180                 185                 190

Gly Ala Val Ser Gly Ile Thr Val Thr Pro Phe Val Thr His Pro Leu
              195                 200                 205

Pro Arg Ala Pro Ile Ile Ala Val Ala Pro Lys Gly Leu Val Val Ala
          210                 215                 220

Ile Ser Leu Ser Ser Ser Thr Ala Asn Asn Cys Asp Ser Ala Arg Ser
225                 230                 235                 240

Arg Pro Thr Arg Phe Phe Pro Ser Ser Leu Arg Pro Val Ala Ser Pro
              245                 250                 255

Ala Thr Thr Gln Ala Leu Gly Ala Arg Asp Val Arg Arg Ser Pro Arg
              260                 265                 270

Ala Asp Thr Leu Ile Ala Ile His Leu Ala Arg Arg Leu Phe Thr Ala
          275                 280                 285

Tyr Thr Ser Ile Thr Arg Thr Arg Cys Ala Pro Arg Ser Arg Ser Pro
290                 295                 300

Thr Ser His Arg Arg Ile Arg Phe Ala Arg Gln Ala Met Met Ala Thr
305                 310                 315                 320

Ser Met Gly Pro Asn Phe Gln Gly His Pro Ala Gly Met Gly His Pro
              325                 330                 335

Gly Val Thr Gly His Pro Met Gly Pro Gly Met Asn Ala Asn Gly Gly
              340                 345                 350

Gln Pro Gly Thr Pro Gly Gly Met Pro His Gln Phe Ala Gly Asn
          355                 360                 365

Pro Met Ala Ala Gly Asn Pro Ala Ala Met Asn Pro Ala Met Met Ala
          370                 375                 380

Ala Met Gln Gln His Gly Gly Asn His Asn Leu Gln Ala Ala Phe
385                 390                 395                 400

Gln His Leu Ser Pro Ala Gln Gln Ala Leu Gln Gln Gln Leu
              405                 410                 415

Gln Asn Gln Phe Ala Asn Gln Gly Ala Val Ala Gln Met Arg Gln Gln
              420                 425                 430

-continued

```
Gln Val Phe Val Gln Gln Arg Gln Ala Leu Met Ala Gln Gln Ala
            435                 440                 445
Met Ala Gln Asn Ser Gly Ile Pro Pro Asn Asn Met Gly Gly Asn Gly
450                 455                 460
Met Ala Ala Asn Gly Met Pro Met Asn Ile Gln Leu Thr Gln Gln
465                 470                 475                 480
Met Gln Gln Leu Arg Gln Gly Gly Arg Ile Asn Pro Met Gln His Pro
                485                 490                 495
Gln Ala Gln Gln His Ala Ala Leu Met Ala Gln Leu Ala Leu His
                500                 505                 510
Gln Gln Gln Gln His Ala Ala Gln Asn Gln Met Gln Gln Gly Gly
            515                 520                 525
Asn Pro Gln Gln Met Gln Ile Asn Ala Gln Ala Leu Gln His Leu Gln
530                 535                 540
Gln Gln Gln Ala Gln Ala Gln Gln Ala Gln Gln Gln Gln Gln Gln
545                 550                 555                 560
Gln Gln Gly Gly Pro Asn Ala Gln Ala Gln Met Gly Gly Gln Gln Gly
                565                 570                 575
Gln Gln Gln Gly Pro Gln Gly Gln Gln Asn Gln Gln Gly Gln Gln Pro
            580                 585                 590
Gly Gln Gln Gly Gln Gln Pro Gln Gly Gln Gly Gln Pro Gly Gln Gln
            595                 600                 605
Gln Ala Gln Ala Gln Ala Gln Ala Gln Ala Gln Ala Gln Ala Gln Ala
            610                 615                 620
Gln Ala Gln Ala Gln Ala Gln Ala Gln Ala Gln Ala Gln Ala Gln Gln
625                 630                 635                 640
Gln Ala Ala Gly Gln Ala Gln Gln Arg Gln Gln Thr Pro Ala Gln Gly
                645                 650                 655
Ser Gln Ala Gly Thr Pro Ala Pro Thr Gly His Gln Ser Gln Gln Gln
                660                 665                 670
Pro Gln Pro Gln Gln His Pro Leu Leu Ala Gln His Met Thr Ala Ala
            675                 680                 685
Gln His Met Ala Met Asn Thr Thr Tyr Met Gln Gln Arg Arg Glu
            690                 695                 700
Gln Met Lys Ala Gln Cys Leu Met Arg Leu Ser Gln Leu Ser Glu Leu
705                 710                 715                 720
Leu Ser Gly Tyr Pro Gly Ala Arg Ser Arg Asp Asp Leu Gly Tyr Trp
                725                 730                 735
Asn Glu Leu Val Met Arg Phe Phe Ser Arg Ser Ala Val Phe Arg His
                740                 745                 750
Thr Leu His Ala Ser Ala Glu Gly Glu Glu Thr Gly Pro Arg Gln Tyr
            755                 760                 765
Asp Ile Thr Phe Pro Ala Ile Ala Arg Tyr Phe His Thr His Phe Gly
770                 775                 780
Ser Gly Val Lys Ser Met Gln Ile Thr Leu Gly Gln Gly Thr Ala Asp
785                 790                 795                 800
Arg Pro Leu Pro Gly Asp Gly Tyr Gln Ile Glu Asn Pro Arg Ala Ser
                805                 810                 815
Met Ile Tyr Trp Phe Glu Thr Gly Ser His Leu Val Ser Ser Gly Asn
                820                 825                 830
Leu Arg Val Val Phe Asp Asn Glu Gln Arg Met Glu Val Phe Glu Phe
835                 840                 845
Leu Ala Thr Ser His Glu Glu Phe Ile Ala Arg Lys Gln Val Ile Asp
```

```
    850                 855                 860

Ala Ala Lys Pro Ala His Val Trp Met Lys Glu Trp His Lys Val Asn
865                 870                 875                 880

Ser Thr Asp Ser Lys Gln Ser Pro Glu Met Ser Lys Lys Gly Lys Gly
                885                 890                 895

Lys Gln Leu Lys Ser Pro Gln Arg Glu Pro Pro Glu Val Leu Asn Asp
            900                 905                 910

Leu Pro Asp Ser Ala Val Asn Arg Gln Gly Val Thr Glu Ala Val Tyr
        915                 920                 925

Gln Phe Leu Glu Ile Val Glu Val Met Gly Gln Met Asn Pro Leu Phe
    930                 935                 940

Asn Phe Thr His Asn Asn Pro Gly Leu Gly Pro Tyr Ala Ala Leu Asp
945                 950                 955                 960

Gln Tyr Val Ser Thr Phe Ile Asn Ala Ala Pro Gly Gln Met Asn Gly
                965                 970                 975

Gln Val Pro Gln Gly Pro Pro Arg Thr Pro Ser Phe Ser Gln Phe Pro
            980                 985                 990

Met Gly Ala Ser Pro Ala Ala Ala  Asn Met Asn Leu Pro  Gly Ser Pro
        995                 1000                1005

His Val  Gly Ser Pro Ala Pro  Gly Gln Ile Gln Ala  Pro Gly Met
    1010                1015                1020

Gln Leu  Gln Gln Ser Gln Gln  Gly Thr Ser Ser Ser  Gly Pro Ser
    1025                1030                1035

Ala Asn  Thr Ser Pro Ala Ser  Asn Lys Arg Arg Arg  Pro Ser Ala
    1040                1045                1050

Val Lys  Ile Glu Glu Asp Val  Ser Gly Ala Gly Thr  Pro Gly Ser
    1055                1060                1065

Gln Val  Asn Gly Thr Gly Asn  Arg Asn Lys Pro Ala  Thr Pro Arg
    1070                1075                1080

Met Pro  Lys Arg Val Lys Gly  Asn Pro Ser
    1085                1090

<210> SEQ ID NO 7
<211> LENGTH: 781
<212> TYPE: PRT
<213> ORGANISM: Verticillium dahliae

<400> SEQUENCE: 7

Met Thr Ser Met Gly Pro Ser Phe Arg Arg Pro Pro Cys Trp His Ala
1               5                   10                  15

Pro Thr Pro Arg Cys Ser Leu Ala Ile Pro Trp Leu Pro Gly Met Pro
            20                  25                  30

His Asn Pro Ser Gln Gln Gly Ala Pro Gly Gly Gly Met Pro Gln Gln
        35                  40                  45

Met His Met Ala Val Ser Gly Pro Gly Gly Gln Val Asn Pro Ala Ala
    50                  55                  60

Met Met Gly Gly Met Pro Pro Gly Ala Gly Ala Pro Asn Ala His Ala
65                  70                  75                  80

Leu Gln His Leu Asn Pro Ala Gln Ala Gln Met Phe Gln Gln Gly Gln
                85                  90                  95

Phe Gly Asn Phe Gly Ser Asn Pro Ser Met Ala Gln Leu Gln Gln His
            100                 105                 110

Gln Arg Phe Ile Gln Gln Gln Gln Ala Ala Arg Gln His Ala Met Ala
        115                 120                 125
```

-continued

```
Gln Gln Ala Ala Phe Gln Ser Asn Met Gln Val Gly Val Asn Gly Met
130                 135                 140
Pro Met Gly Val His Met Asn Pro Ala Gln Met Ala Ala Phe Arg Gln
145                 150                 155                 160
Ala Arg Met Gln Pro His Ala His Asn Gln Ala Met Leu Ala His Gln
                165                 170                 175
Ile Ala Leu Gln Gln Gln Gln Val Ala Gln Asn Gln Gln Met Gln
            180                 185                 190
Gln Gly Gly Gln Pro Gly Gln Pro Val Gln Met Ser Ala Gln Gln Met
        195                 200                 205
Gln Ser Leu Gln Gln Ala Gln Met Ala Ala Leu Gln Ala Gln Gln Gln
    210                 215                 220
Gly Gln Gln Gln Ala Gln Gln Gln Gln Gln Gln Gln Gln Gln Ala Gln
225                 230                 235                 240
Gln Gln Gln Ala Gln Gln Gln Ala Gln Gln Gln Ala Gln Gln Ala
                245                 250                 255
Gln Gln Gln Gln Gln Gln Gln Ala Gln Gln Gln Gln Gln Gly
            260                 265                 270
Gln Pro Pro Gln Gln Pro Gln Gln Pro Gly Gly Pro Gln Pro Gln Gln
        275                 280                 285
Gln Thr Pro Gln Gln Gln Ala Ala Gln Pro Ala Gly Pro Gln Ser Ala
    290                 295                 300
Gly His Pro Thr Pro Ser Gln Thr Pro Gly Pro Gln Pro Asn Gln Gln
305                 310                 315                 320
Pro Gln Pro Pro Gln Ala Gln Asn Gln Ala Gln Gly Pro Gln Pro Gly
                325                 330                 335
Gln Gln Pro Gln Gln Gln Leu Asn Pro Ala Gln Gln Ala Gln His
            340                 345                 350
Ala Ala Ala Gln Ala Ala Met Ala Asn Asn Met Ala Leu Ala Gln Gln
        355                 360                 365
Gln Ala Gln Ala Gln Gln Ala Arg Arg Glu Ala Met Lys Gly His Cys
    370                 375                 380
Leu Leu Lys Leu Met Gln Phe Ser Glu His Leu Ser Gly Phe Pro Gly
385                 390                 395                 400
Ser Arg Gly Lys Asp Asp Leu Ser Tyr Trp Asn Met Phe Val Asn Gln
                405                 410                 415
Phe Phe Ser Thr Lys Gly Val Phe Arg His Ser Val His Ile Thr Asp
            420                 425                 430
His Glu Asp Pro Ser Asp Lys Gln Tyr Glu Ile Ser Tyr Pro Ala Leu
        435                 440                 445
Ala Arg Tyr Phe His Thr His Phe Asp Ser Gly Val Lys Asn Met Gln
    450                 455                 460
Leu Ile Met Glu Lys Gly Thr Thr Asp Arg Pro Leu Pro Gly Asp Gly
465                 470                 475                 480
His Trp Ile Glu Asn Thr Lys Ser Ser Leu Val Tyr Trp Phe Asp Asn
                485                 490                 495
Gly Ser His Leu Val Ala Thr Gly Thr Val Arg Ala His Phe Asp His
            500                 505                 510
Glu Gln Lys Ile Glu Leu Phe Glu Phe Val Thr Ser Gly His Glu Glu
        515                 520                 525
Tyr Ile Ser Arg Lys Ser Val Ile Glu Ser Ala Lys Pro Ala His Asn
    530                 535                 540
Trp Val Lys Glu Trp His Lys Val Asn Ser Gln Asp Ser Lys Thr Ser
```

```
                 545                 550                 555                 560
Pro Glu Met Ser Lys Lys Gly Lys Ala Arg Pro Leu Lys Ser Pro Gln
                 565                 570                 575

Asn Pro Pro Glu Ala Leu Val Asp Leu Pro Glu Ser Ser Val Lys
            580                 585                 590

Arg Gly Met Gly Val Thr Glu Val Phe Gln Phe Leu Glu Ile Val
            595                 600                 605

Glu Val Phe Gly Gln Met Asn Pro Leu Phe Gly Phe Ser His Ser His
        610                 615                 620

Pro Gly Met Arg Pro Tyr Leu Ala Leu Glu Gln Tyr Val Asn Gln Ile
625                 630                 635                 640

Asn Ser Gln Pro Gln Pro Asn Met Asn Gly Gln Pro Met Gln Gln Gly
                645                 650                 655

Pro Pro Arg Thr Pro Gly Phe Gly Gln Phe Pro Val Pro Gln Met Pro
                660                 665                 670

Pro Gly Gly Val Gly Ala Ser Pro Ala Gln Pro His Met Gln Leu Pro
            675                 680                 685

Gly Ser Pro His Ile Met Gly Ser Pro Ala Gln Val Gln Met Gln Ala
        690                 695                 700

Pro Gly Met Gln Leu Gln Gln Ser Gln Gln Gly Thr Ser Ser Ser Gly
705                 710                 715                 720

Pro Ser Ala Asn Thr Ser Pro Ala Ser Asn Lys Arg Arg Arg Pro Ser
                725                 730                 735

Gly Val Lys Thr Glu Asp Asp Gly Ser Ser Ala Pro Thr Pro Gln Ser
                740                 745                 750

Gly Pro Gly Gly Gln Val Asn Gly Val Gly Asn Lys Gly Lys Pro Pro
            755                 760                 765

Thr Pro Arg Met Pro Lys Arg Val Lys Gly Asn Pro Ala
            770                 775                 780

<210> SEQ ID NO 8
<211> LENGTH: 767
<212> TYPE: PRT
<213> ORGANISM: Thielavia terrestris

<400> SEQUENCE: 8

Met Ala His Asn Pro Ser Gln Pro Gly Ala Thr Pro Gly Gly Ile Pro
1               5                   10                  15

His Gln Leu Leu Gly His Met Gly Val Ser Gly Pro Gly Pro Gln Ile
            20                  25                  30

Asn Ala Ala Ala Leu Met Gly Gly Met Pro Pro Gly Ala Gly Asn Pro
        35                  40                  45

Ser Ala His Ala Met Gln His Leu Asn Pro Ala Gln Ala Gln Met Tyr
    50                  55                  60

His Gln Ala Gln Leu Asn Gln Met Tyr Ala Asn Asn Pro Ala Ala Gln
65                  70                  75                  80

Gln Gln Leu Gln Gln Gln Arg Leu Gln Ile Leu Gln Gln Gln Gln His
                85                  90                  95

Ala Arg Gln Ala Leu Met Ala Gln His Ala Ala Tyr Asn Thr Met Pro
            100                 105                 110

Pro Gly Thr Met Gly Met Pro Leu Ser Gln Met Asn Pro Ala Gln Ala
        115                 120                 125

His Met Ala Ala Leu Ser Arg Arg Met Pro Val Ala Ala Pro Leu His
    130                 135                 140
```

```
Ile Gln Gln Ala Gln Leu Ala Gln Ala Gln Gly Gln Pro Ile Asn
145                 150                 155                 160

Pro Ala Met Leu Ala Leu Gln Gln Gln Gln Leu Gln Met Gly Gln
            165                 170                 175

Gln Gly Ala Ser Pro Asn Gln His Gln Ile Asn Ala Gln His Ile Asn
            180                 185                 190

Met Gln Gln Ala His Ile Ala Ala Ile Gln Ala Gln Ala Gln Gln
    195                 200                 205

Ala Gln His Gln Ala Ala Gln Gln Ala Ala Gln Ala Ala Gln Ala
210                 215                 220

Ala Gln Ala Gln Gln Gly Pro Gly Gln Pro Gln Ala Gln Pro
225                 230                 235                 240

Gln Gln Pro Gln Pro His Ser Gln Pro Gln Gln Gln Gly Pro
                245                 250                 255

Gln Pro Ala Pro Ala Gly Pro Gly Thr Asn Gly Pro Ala Ser Ala Pro
            260                 265                 270

Gly Ala Gly Gln Gly His Thr Pro Gln Pro Asn Pro Gln Gln Pro
            275                 280                 285

Gln Ala Pro Pro Thr Pro Gln Thr Thr Gln Ala Gln His Gln Ala
    290                 295                 300

Gln Leu Val Ala Gln Ala Gln Gln Ala Gln Ala Gln Ala His Ala His
305                 310                 315                 320

Ala Gln Ala Gln Ala Gln Ala Gln His Ala Gln Ala Gln Ala Gln
            325                 330                 335

Ala Gln Ala Gln Ala Gln Gly Gln Val Pro Pro Gln His Ala
            340                 345                 350

Ala Gly Leu Ala Ser Leu Ile Gln Gln Arg Arg Glu Thr Met Thr Leu
            355                 360                 365

Arg Gly Val His Gln Leu Lys Leu Val Gln Phe Ser Glu His Leu Ser
    370                 375                 380

Gly Phe Ser Gly Ser Glu Gly Lys Asp Asp Leu Asp Tyr Trp Asn Arg
385                 390                 395                 400

Phe Val Gln Gln Phe Phe Ser Gln Lys Gly Ile Phe Arg His Thr Ile
            405                 410                 415

Leu Met Arg Asp Gly Glu Asp His Ala Gln Glu Lys His Tyr Glu Ile
            420                 425                 430

Ala Tyr Pro Ala Leu Ala Arg Tyr Phe His Thr His Phe Glu Ser Gly
    435                 440                 445

Val Lys Lys Met Gln Leu Val Leu Asp Lys Gly Thr Thr Glu Arg Ala
450                 455                 460

Leu Pro Asn Asp Cys Tyr Val Ile Glu Asn Pro Lys Ala Ser Leu Val
465                 470                 475                 480

Tyr Trp Phe Asp Gly Gly Ser His Leu Val Ala Thr Gly Ile Leu Arg
            485                 490                 495

Val Gln Phe Asp Ser Glu Ser Arg Phe Asp Leu Phe Glu Phe Gln Thr
            500                 505                 510

Thr Gly His Glu Glu Tyr Ile Ser Arg Arg Leu Val Ile Gln Ala Ala
    515                 520                 525

Arg Pro Ala His Asn Trp Val Lys Glu Trp His Ser Leu Asn Gln Gln
    530                 535                 540

Asp Pro Lys Gln Ser Pro Glu Leu Ser Lys Lys Ser Lys Pro Arg Pro
545                 550                 555                 560

Ala Lys Ala Pro Ala Arg Pro Pro Pro Asp Leu Glu Leu Pro His Ser
```

```
                565                 570                 575
Val Val Lys Ser Gly Met Gly Ile Thr Glu Ala Val Tyr Gln Phe Leu
            580                 585                 590

Glu Met Val Glu Ile Met Gly Gln Met Asn Pro Leu Phe Gly Tyr Tyr
        595                 600                 605

His Ala His Pro Gly Leu Ala Pro Tyr Ala Ala Leu Glu Gln Tyr Met
    610                 615                 620

Ser Gln Ile Asn Gly Ser Ala Ala Gln Gly Met Asn Gly Gln Pro Met
625                 630                 635                 640

Pro Gln Gly Gly Pro Arg Thr Pro Gly Phe Gly Gln Phe Gln Met Gly
                645                 650                 655

Ala Ser Pro Ala Ile Ser Asn Gln Met Leu Pro Gly Ser Pro His Val
            660                 665                 670

Ala Gly Ser Pro Val Pro Gly Gln Val Gly Ala Pro Met Met Gln Leu
        675                 680                 685

Gln Ala Ser Gln Gln Gly Thr Asn Ser Ser Gly Pro Ser Ala Asn Thr
    690                 695                 700

Ser Pro Ala Gln Asn Ser Asn Lys Arg Arg Arg Pro Ser Thr Val Lys
705                 710                 715                 720

Ala Glu Glu Glu Thr Pro Ala Ser Ala Pro Thr Pro Ala Pro Val Gly
                725                 730                 735

Thr Pro Gln Met Asn Gly Val Gln Ile Lys Gly Lys Gln Pro Pro Thr
            740                 745                 750

Pro Arg Met Pro Lys Arg His Lys Thr Gly Asn Asn Pro Gly Leu
        755                 760                 765

<210> SEQ ID NO 9
<211> LENGTH: 597
<212> TYPE: PRT
<213> ORGANISM: Verticillium albo-atrum

<400> SEQUENCE: 9

Met Leu Gly Ser Thr Asp Arg Ser Pro Ala Ala Ala Ala Ser Gly Ala
1               5                   10                  15

Lys Pro Ala Asp Ala Ala Arg Trp Thr Pro Gly Gln Pro Val His Met
            20                  25                  30

Ser Ala Gln Gln Met Gln Ser Leu Gln Gln Ala Gln Ile Ala Ala Leu
        35                  40                  45

Gln Ala Gln Gln Gln Gly His Gln Gln Ala Gln Gln Gln Gln Gln Gln
    50                  55                  60

Gln Gln Gln Gln Gln Gln Ala Gln Gln Gln Gln Ala Gln Gln Gln Gln
65                  70                  75                  80

Ala Gln Gln Gln Ala Gln Gln Ala Gln Gln Gln Gln Gln Gln Gln Gln
                85                  90                  95

Gln Gln Gln Gln Gln Gln Gln Gln Gln Gln Gln Gln Gly Gln Pro Pro
            100                 105                 110

Gln Gln Gln Gln Gln Pro Gly Gly Pro Gln Pro Gln Gln Gln Thr Pro
        115                 120                 125

Gln Gln Gln Ala Ala Gln Pro Ala Gly Pro Gln Ser Ala Gly His Pro
    130                 135                 140

Thr Pro Ser Gln Thr Pro Gly Pro Gln Pro Asn Gln Gln Pro Gln Pro
145                 150                 155                 160

Pro Gln Ala Gln Asn Gln Ala Gln Gly Pro Gln Pro Gly Gln Gln Pro
                165                 170                 175
```

```
Gln Gln Gln Leu Asn Pro Ala Gln Gln Ala Gln His Ala Ala Ala
            180                 185                 190
Gln Ala Val Met Ala Asn Asn Met Ala Leu Ala Gln Gln Gln Ala Gln
        195                 200                 205
Ala Gln Gln Ala Arg Arg Glu Gly Met Lys Gly His Cys Leu Leu Lys
    210                 215                 220
Leu Met Gln Phe Ser Glu His Leu Ser Gly Phe Ser Arg Lys Asp Asp
225                 230                 235                 240
Leu Ser Tyr Trp Asn Met Phe Val Asn Gln Phe Ser Thr Lys Gly
            245                 250                 255
Val Phe Arg His Ser Val His Ile Thr Asp His Glu Asp Pro Ser Asp
        260                 265                 270
Lys His Gly Val Arg Asn Met Gln Trp Phe Met Lys Lys Ala Thr Thr
    275                 280                 285
Asp Arg Pro Leu Pro Gly Asp Gly His Trp Ile Glu Asn Thr Lys Ser
        290                 295                 300
Ser Leu Val Tyr Trp Phe Asp Asn Gly Ser His Leu Val Ala Thr Gly
305                 310                 315                 320
Thr Val Arg Ala His Phe Asp His Glu Gln Lys Ile Glu Leu Phe Glu
            325                 330                 335
Phe Val Thr Ser Gly His Glu Glu Tyr Ile Ser Arg Lys Ser Val Ile
        340                 345                 350
Glu Ser Ala Lys Pro Ala His Asn Trp Val Lys Glu Trp His Lys Val
    355                 360                 365
Asn Ser Gln Asp Ser Lys Thr Ser Pro Glu Met Ser Lys Lys Gly Lys
        370                 375                 380
Ala Arg Pro Leu Lys Ser Pro Gln Asn Pro Pro Glu Ala Leu Val
385                 390                 395                 400
Asp Leu Pro Glu Ser Ser Val Lys Arg Gly Met Gly Val Thr Glu Glu
            405                 410                 415
Val Phe Gln Phe Leu Glu Ile Val Glu Val Phe Gly Gln Met Asn Pro
        420                 425                 430
Leu Phe Gly Phe Ser His Ser His Pro Gly Met Arg Pro Tyr Leu Ala
    435                 440                 445
Leu Glu Gln Tyr Val Asn Gln Ile Asn Ser Gln Pro Gln Pro Asn Met
    450                 455                 460
Asn Gly Gln Pro Met Gln Gln Gly Pro Pro Arg Thr Pro Gly Phe Gly
465                 470                 475                 480
Gln Phe Pro Val Pro Gln Met Pro Pro Gly Gly Val Gly Ala Ser Pro
            485                 490                 495
Ala Gln Pro His Met Gln Leu Pro Gly Ser Pro His Ile Met Gly Ser
        500                 505                 510
Pro Ala Gln Ile Gln Met Gln Ala Pro Gly Met Gln Leu Gln Gln Ser
    515                 520                 525
Gln Gln Gly Thr Ser Ser Gly Pro Ser Ala Asn Thr Ser Pro Ala
        530                 535                 540
Ser Asn Lys Arg Arg Pro Ser Gly Val Lys Thr Glu Asp Asp Gly
545                 550                 555                 560
Ser Ser Ala Pro Thr Pro Gln Ser Gly Pro Gly Gln Val Asn Gly
            565                 570                 575
Val Gly Asn Lys Gly Lys Pro Pro Thr Pro Arg Met Pro Lys Arg Val
        580                 585                 590
Lys Gly Asn Pro Ala
```

595

<210> SEQ ID NO 10
<211> LENGTH: 793
<212> TYPE: PRT
<213> ORGANISM: Neurospora crassa

<400> SEQUENCE: 10

```
Met Ala Ser Met Pro Ile Gly Pro Ser Phe Ser Pro His Pro Gly Gly
1               5                   10                  15

Met Gln Gln His Pro Gly Ala Pro Pro Gly His His Met Ala Pro Gly
            20                  25                  30

Met Ala His Asn Pro Ser Gln Pro Gly Ala Thr Pro Ala Met Ala His
        35                  40                  45

Gln Met Val Ala His Leu Gly Val Ser Gly Pro Gly Pro Gln Met Ser
    50                  55                  60

Ala Gly Ala Leu Met Gly Gly Met Pro Pro Gly Thr Pro Asn Ala His
65                  70                  75                  80

Ile Ala Met Gln His Leu Asn Pro Gln Gln Met Ala Ala Tyr Gln Gln
                85                  90                  95

Gln Ile Asn Gly Met Gly Phe Pro Asn Asn Pro Ala Met Gln Gln Gln
            100                 105                 110

Leu Gln Gln Ala Arg Leu Gln Gln Leu Gln Gln Ala Gln His Gln Arg
        115                 120                 125

Leu Met Gln Ala Gln Gln Ala Gln Ala Gln Tyr Gly Asn Leu Gly Gly
    130                 135                 140

Met Pro Ile Gly Val Pro Gly Met Gly Gln Met Asn Pro His Met Ala
145                 150                 155                 160

Gln Leu Met Gln Arg Arg Ala Met Ala Gly Pro Met Pro Met Ala His
                165                 170                 175

Gln Met Gln Gln His Leu Ala Gln Gln His Gln Gly Gln Gly Met Asn
            180                 185                 190

Pro Asn Leu Ile Ala Gln Gln Met Ala Met Gln Gln Gln Gln Gln Gln
        195                 200                 205

Gln Leu Gln Gln Gln Gln Gln Gln Gln Gln Gln Gln Gln Gln Gln Gln
    210                 215                 220

Gln Gln Gln Gln Gln Gln Gln Gln Gln Gln Met Ala Gln Gln
225                 230                 235                 240

Gly Asn Asn Pro Gly Gln His Gln Ile Asn Pro Gln Gly Pro Gly Leu
                245                 250                 255

Asn Met Gln Ala Gln Leu Ala Ala Leu His Thr Gln Gln Ala His Ala
            260                 265                 270

Gln Gln Ser Ala Ala Val Gln Ala Ala Gln Ala Gln Ala Gln Ala Gln
        275                 280                 285

Ala Gln Gln Gly Gly Pro Gly Gln Pro Gln Gln Gln Pro Gln Gln Pro
    290                 295                 300

Gln Pro Gln Pro Pro Gln Gln Pro Gln Gln Gln Pro Gly Gln Pro
305                 310                 315                 320

Gln Gln Pro Thr Gln Gln Pro Gln Val Gln Pro Gly Pro Gly Val
                325                 330                 335

Asn Gly Pro Ala Gln Asn Gln Gly Pro Ala Pro Gly Pro Thr Gln Gln
            340                 345                 350

Pro Asn Ala Gln Gln Gln Val Ser Pro Gln Thr Pro Gln Thr Thr Gln
        355                 360                 365
```

```
Ala Gln Gln Ala Gln Leu Ala His Ala Gln Val Gln Ala Ala Asn
    370                 375                 380
Val Ala Asn Leu Leu Gln Gln Lys Arg Val Asp Ser Ala Asn Leu Lys
385                 390                 395                 400
Gly Gln Cys Leu Leu Lys Leu Asn Ser Phe Asn Glu His Leu Asn Gly
                    405                 410                 415
Phe Thr Gly Ser Gln Gly Ala Asp Gly Leu Lys Tyr Trp Gln Leu Phe
            420                 425                 430
Val Gln Arg Phe Phe Ser Gln Lys Gly Val Phe Arg Gln Thr Phe Lys
        435                 440                 445
Lys Arg Glu Asp Glu Ala Ala Asp Pro Lys Pro Tyr Glu Ile Asp Val
450                 455                 460
Ala Leu Pro Arg Phe Phe Asn Val His Phe Glu Ser Gly Val Ser
465                 470                 475                 480
Lys Met Gln Leu Val Met Gln Gly Thr Thr Asp Arg Ser Leu Pro His
                    485                 490                 495
Asp Gly His Phe Ile Glu Ile Ala Arg Ala Ser Val Phe Tyr Trp Tyr
            500                 505                 510
Asp Asn Gly Ser His Val Val His Asn Gly Thr Leu Arg Ile Gln Phe
        515                 520                 525
Asp Ser Asp Gln Phe Ile Glu Leu Phe Asp Phe Val Val Glu Asn His
530                 535                 540
Glu Glu Tyr His Ser Arg Arg Ala Ile Ile Glu Ala Ala Arg Pro Ser
545                 550                 555                 560
His Thr Trp Ile Lys Glu Trp Arg Ser Leu Asn Pro Pro Asp Ser Lys
                    565                 570                 575
Gln Ser Pro Glu Met Ser Lys Lys Gly Lys Gln Arg Pro Tyr Lys Ser
            580                 585                 590
Pro Ala Thr Pro Pro Asp Ile Glu Leu Pro Asp Ser Cys Val Lys
        595                 600                 605
Ile Gly Met Gly Ile Pro Glu Gly Val Phe Gln Phe Leu Glu Met Ala
610                 615                 620
Asp Ile Met Gly Gln Met Ser Pro Leu Phe Thr Phe Ser His Asn His
625                 630                 635                 640
Pro Gly Ile Pro Pro Tyr Ala Ala Leu Glu Gln Phe Met Thr Gln Ile
                    645                 650                 655
Thr Gly Gln Gly Pro Ala Val Asn Gly Gln Ala Met Pro Gln Gly Val
            660                 665                 670
Pro Arg Thr Pro Gly Tyr Asn Gln Phe Pro Met Gly Ala Ser Pro Ala
        675                 680                 685
Met Ala Asn Gln Met Leu Pro Gly Ser Pro His Ile Gly Ser Pro Ala
690                 695                 700
Pro Gly Gln Met Gln Ala Pro Ala Met Gln Leu Gln Val Ser Gln Gln
705                 710                 715                 720
Gly Thr Asn Ser Ser Gly Pro Ser Ala Asn Thr Ser Pro Gln Gln Asn
                    725                 730                 735
Asn Lys Lys Arg Arg Ala Ser Gln Ala Lys Leu Glu Asp Asp Gly Pro
            740                 745                 750
Thr Ser Ala Pro Thr Pro Ala Thr Met Gly Thr Pro Gln Met Pro Gln
        755                 760                 765
Met Asn Gly Val Gln Val Lys Ala Lys His Pro Pro Thr Pro Arg Met
770                 775                 780

Gln Lys Arg Met Lys Asn Asn Gln Gly
```

<210> SEQ ID NO 11
<211> LENGTH: 871
<212> TYPE: PRT
<213> ORGANISM: Chaetomium thermophilum

<400> SEQUENCE: 11

```
Met Met Thr Ser Ile Gly Pro Ser Phe Ser Pro His Pro Gly Met
1               5                   10                  15

Gln Gln His Pro Gly Ala Pro Gly His Pro Met Ala Pro Gly Met
                20                  25                  30

Ala His Ala Pro Ser Gln Pro Gly Ala Thr Pro Gly Ala Met Pro His
                35                  40                  45

Pro Leu Ala Gly Pro Met Gly Val Ser Gly Pro Gly Pro Gln Ile Asn
50                  55                  60

Pro Ala Ala Leu Met Gly Gly Met Ala Pro Gly Ala Gly Ala Pro Asn
65                  70                  75                  80

Ala His Val Met Gln His Leu Asn Pro Ala Ala Gln Met Phe His
                85                  90                  95

Gln Gln Gln Met Asn Gln Met Tyr Ala Asn Asn Pro Ala Leu Gln Gln
                100                 105                 110

Gln Val Gln Gln Gln Leu Gln Gln Arg Leu Gln Gln Leu Gln Gln
                115                 120                 125

Gln Gln His Ala Arg Gln Ala Leu Met Ala Gln Ala Gln His Pro
130                 135                 140

Ala Tyr Gln Asn Met Gly Val Pro Val Gly Leu Pro Leu Ala Gln Met
145                 150                 155                 160

Pro Gln Gly Ala Gln Ala Ala His Leu Ala Ala Leu Gln Arg Ser Arg
                165                 170                 175

Met Pro Met Val Pro Phe Gln Gln Ala Gln Leu Pro Gln Gln Gln Gly
                180                 185                 190

His Pro Met Asn Ser Leu Met Ala Gln Gln Ile Ala Leu Gln Gln Gln
                195                 200                 205

Gln Ile Gln Met Ser Gln Gln Gly Ala Thr Pro Gly Gln His Pro Leu
210                 215                 220

Thr Pro Gln His Asn Leu Ile Gln Ala Gln Gln Leu Ala Ala Ile Gln
225                 230                 235                 240

Ala His Gln Gln Gln Ala Ala Ala Gln Gln Ala Gln Gln Gln Ala
                245                 250                 255

Gln Gln Gln Ala Ala Gln Gln Gln Ala Val Gln Ala Ala Gln Ala
                260                 265                 270

Ala Gln Ala Thr Gln Ala Ala Gln Val Ala Gln Ala Pro Gln Gly Pro
                275                 280                 285

Gly Gln Pro Gln Gln Pro Pro Val Ser Gln Ala Gln Pro Pro Gly
                290                 295                 300

Pro Pro Gln Gln Pro Ala Pro Pro Gly Thr Thr Ala Pro Val Thr
305                 310                 315                 320

Thr Ala Pro Ile Thr Ala Ser Thr Pro Val Thr Gln Val Gln Thr Pro
                325                 330                 335

Gln Pro Asn Pro Gln Gln Pro Pro Ala Pro Gln Pro Pro Gln
                340                 345                 350

Ala Thr Gln Ala Gln Gln Leu Gln Leu Ala Ala Gln Ala Ala Ala
                355                 360                 365
```

-continued

```
Ala Gln Gln His Ala Ala Gln Val Gln Gln Val Gln Gln Gln
    370                 375                 380
Gln Gln Gln Gln Gln Gln Gln Gln Gln Gln Gln Gln Gln Gln Gln
385                 390                 395                 400
Gln Gln Gln Gln Gln Gln Gln Gln Gln Gln Gln Gln Gln Gln Gln
            405                 410                 415
Gln Gln Gln Gln Gln Gln Gln Gln Gln Gln His Gln Pro Gln Pro
        420                 425                 430
Gln Gln Gln Gln Gln Pro Gln Ser Gln Val His Ala Gln Pro Gln
            435                 440                 445
Gln Ala Val Gly Ala Val Met Met Arg Pro Gln Arg Pro Asp Pro Leu
450                 455                 460
Leu His Arg Phe Lys Leu Phe Gln Phe Ala Glu Tyr Leu Ser Gly Phe
465                 470                 475                 480
Gln Pro Val Lys Gly Lys Asp Asp Leu Glu Tyr Trp Thr Arg Cys Val
            485                 490                 495
Asn Val Phe Phe Ser Gln Lys Gly Ile Phe Arg His Val Val Leu Met
                500                 505                 510
Arg Glu Asn Asp Asp Gln Ala Gln Glu Lys Gln Tyr Glu Ile Ala Phe
        515                 520                 525
Pro Ala Leu Pro Arg Tyr Phe Gln Thr His Phe Asp Ser Gly Val Arg
    530                 535                 540
Lys Ile Gln Leu Val Met Asp Lys Gly Tyr Ser Glu Arg Ser Leu Pro
545                 550                 555                 560
Asn Asp Cys Tyr Val Leu Glu Asn Arg Asn Ser Ser Leu Val Tyr Trp
            565                 570                 575
Phe Asp Gly Asp Ser His Leu Val Ala Thr Gly Ile Ile Arg Val Gln
                580                 585                 590
Phe Ser Asp Asp His Lys Phe Asp Leu Met Glu Phe Ile Thr Thr Gly
        595                 600                 605
His Glu Glu Tyr Ile Ser Arg Arg Leu Val Ile Gln Ala Ala Arg Pro
    610                 615                 620
Ala His Asn Trp Val Lys Glu Trp His Gln Leu Asn Ser Gln Pro Asp
625                 630                 635                 640
Gly Lys Gln Ser Pro Glu Met Ser Lys Lys Gly Lys Thr Arg Pro Thr
            645                 650                 655
Lys Ala Pro Ala Gly Pro Pro Pro Asp Leu Glu Leu Pro His Ser Tyr
                660                 665                 670
Val Lys Ser Asn Met Gly Leu Thr Glu Ala Val Tyr Gln Phe Leu Glu
        675                 680                 685
Met Val Glu Ile Met Gly Gln Met Asn Pro Leu Phe Asn Tyr Tyr His
    690                 695                 700
Asn Asn Pro Gly Leu Ser Pro Tyr Thr Ala Leu Asp Gln Tyr Val Asn
705                 710                 715                 720
Leu Ile Asn Gln Gln Gly Met Asn Gly Gln Pro Met Pro Gln
            725                 730                 735
Ala Gly Ala Pro Arg Thr Pro Ser Phe Gly Gln Phe Gln Met Thr His
                740                 745                 750
Ser Pro Ala Met Ala Asn Ser Met Leu Pro Gly Ser Pro His Ile Ala
        755                 760                 765
Asn Ser Pro Ala Pro Gly Ser Met Ala Ala Pro Val Met Gln Met Gln
    770                 775                 780
Ala Ser Gln Gln Gly Thr Asn Ser Ser Gly Pro Ser Ala Asn Thr Ser
```

-continued

```
785                 790                 795                 800

Pro Ala Gln Gly Asn Lys Arg Arg Arg Pro Ser Thr Val Lys Ala Glu
                805                 810                 815

Glu Asp Ala Asn Asn Ala Ala Ala Gln His Ala Gln Asn Gly Pro Val
            820                 825                 830

Ser Ala Pro Thr Pro Val Pro Val Pro Val Gly Thr Pro Gln Leu Asn
        835                 840                 845

Gly Val Gln Leu Lys Lys Gln Pro Pro Thr Pro Arg Leu Pro Asn Lys
    850                 855                 860

Arg Gln Lys Thr Gly Asn Thr
865                 870

<210> SEQ ID NO 12
<211> LENGTH: 809
<212> TYPE: PRT
<213> ORGANISM: Magnaporthe oryzae
<400> SEQUENCE: 12

Met Thr Ser Met Ser Met Gly Pro Ser Phe Ser Pro His Pro Gly Ala
1               5                   10                  15

Met Gln His Pro Pro Gly Val Pro Gln Gly His Pro Gly Met Ala Pro
            20                  25                  30

Gly Met Ala His Asn Pro Ser Gln Pro Gly Val Gln Pro Gly Gly Met
        35                  40                  45

Pro His Gln Met His Met Gly Val Ser Gly Pro Gly Pro Gln Val Asn
    50                  55                  60

Pro Ala Ala Leu Met Gly Gly Val Gly Met Pro Pro Gly Ala Gly Pro
65                  70                  75                  80

Asn Pro His Met Gln Gln Leu Ser Gln Gln Gln Met Phe Gln His Gln
                85                  90                  95

Gln Gln Gln Gln Met Asn Asn Met Ala Ala Tyr Ala Asn Asn Pro Ala
            100                 105                 110

Ala Leu Gln His Leu Gln Ala Gln Arg Met Asn Gln His Leu Gln Gln
        115                 120                 125

Gln Gln Ala Arg Gln Met Leu Met Ala Gln Gln Ser Val Tyr Gly Gly
    130                 135                 140

Leu Asn Pro Gln Gln Leu Gln Gln Met Gln Gln Met Gln Gln Met Gln
145                 150                 155                 160

His Leu Asn Pro Ala Gln Leu Gln Gln Met Gln Arg Leu Arg Gln Gln
                165                 170                 175

Asn Pro Ala Ala Ala Ala Ala Gln Gln Gln Ala Leu Ile Ala Gln Gln
            180                 185                 190

Met Ala Leu Gln Gln His Gln Gln Gln His Gln Asn Gln Gly His Leu
        195                 200                 205

Gly Asn Ala Gln His Pro Asn Pro Ala Ala Ile Ala Ala Met Gln Gln
    210                 215                 220

Ala His Ala Gln Ala Gln Ala His Ala Gln Ala Gln Ala Gln Gln Ala
225                 230                 235                 240

Gln Gln Gln Ala Gln Gln Gln Gln Ala Gln Gln Gln Gln Gln Gln Gln
                245                 250                 255

Gln Gln Gln Gln Gln Gln Gln Gln Gln Gln Gln Gln Gln Gln Gln Gln
            260                 265                 270

Ala Gln Gln Gln Gln Gln Gln Gln Gln Gln Gln Gln Gln Gln Gln Gln
        275                 280                 285
```

```
Gln Gln Gln Ala Gln Gln Gln Ala Gln Gln Gln Ala Gln Gln Gln Gln
    290                 295                 300
Gln Gln Pro Pro Gln Ala Gln Gln Gln Gln Pro Pro Gln Gln Gln Gly
305                 310                 315                 320
Pro Gln Pro Pro Gln Gln Gln Pro Gln Ala Gln Pro Ala Gln Ala Gln
                325                 330                 335
Gly Pro Gln Gln Pro Pro Thr Thr Gln Ala Pro Gln Gly Gln Pro Gly
                340                 345                 350
Pro Gly Pro Asn Ala Pro Pro Gly Gln Pro Gln Asn Gln Gly Gln Gly
                355                 360                 365
Pro Gln Gln Pro Asn Ala Gln Ala Gln Gln Ala Ala Met Pro Gln Pro
            370                 375                 380
Ala Gly Pro Gly Gly Gln Pro Pro Gln Ala Leu Leu Val Ala Gln Gln
385                 390                 395                 400
His Ala Phe Ala Asn Ser Ala Leu Leu Gln Lys Arg Glu Asn Met Lys
                405                 410                 415
Gly His Cys Leu Leu Lys Leu Leu Gln Phe Cys Glu His Leu Ser Gly
                420                 425                 430
Phe Gln Gly Gly Lys Asp Pro Thr Asp Leu Ser Tyr Trp Asn Glu Phe
            435                 440                 445
Val His Arg Phe Phe Ser Pro Arg Ala Val Phe Arg Phe Val Val His
        450                 455                 460
Glu Tyr Gly Asp Asp Gly Val Ala Ala Asp Lys Pro Tyr Glu Leu Gly
465                 470                 475                 480
Phe Pro Ile Leu Ala Arg Tyr Phe Asn Ser Tyr Phe Gln Gly Gly Ala
                485                 490                 495
Thr Asn Ile Gln Leu Val Leu Asp Lys Gly Thr Thr Asp Lys Pro Leu
                500                 505                 510
Thr Gly Asp Ser His Phe Ile Glu Asn Thr Lys Ala Ser Met His Phe
            515                 520                 525
Trp Tyr Pro Gly Asn Leu Met Val Met Ala Ser Gly Thr Leu Arg Ala
            530                 535                 540
His Phe Asp Gly Glu Gln Lys Ile Glu Leu Leu Glu Phe Gln Gln Asn
545                 550                 555                 560
His Tyr Glu Glu Phe Leu Pro Arg Ser Leu Val Leu Gln Gly Ala Lys
                565                 570                 575
Pro Thr His Thr Trp Ile Lys Asp Trp Lys Gln Ala Asn Asn Asp Ala
                580                 585                 590
Lys Ala Ser Pro Glu Met Ser Lys Lys Ser Lys Gln Arg Gln Phe Lys
            595                 600                 605
Ser Pro Gln Ser Val Pro Pro Asp Leu Glu Leu Pro Asp Ala Leu Val
        610                 615                 620
Asn Lys Asn Gly Leu Ser Ala Ala Val Gln Asn Phe Leu Glu Ile Ser
625                 630                 635                 640
Glu Ile Leu Ser His Met Asn Pro Leu Phe Ser His Ala His Met His
                645                 650                 655
Pro Asn Leu Gly Pro Tyr Ala Ala Leu Asn Ser Tyr Ile Gln Met Val
                660                 665                 670
Ser Gly Gln Gly Asp Asn Ala Gly Val Met Asn Gly Gln Pro Met Pro
            675                 680                 685
Gln Gly Ala Gly Gly Gln Pro Arg Thr Pro Ser Tyr Gly Gln Phe Pro
        690                 695                 700
Met Gly Ala Ser Pro His Ala Ala Asn Leu Gln Leu Pro Gly Ser Pro
```

```
                705                 710                 715                 720
His Ile Gly Ser Pro Ala Met Ala Gln Gln Met Val Pro Gln Gln Ser
                725                 730                 735

Gln Gln Gly Thr Ser Ser Gly Pro Ser Ala Asn Thr Ser Pro Ala
            740                 745                 750

Gly Thr Lys Arg Arg Pro Ser Gly Val Lys Thr Glu Asp Asp Gly
            755                 760                 765

Thr Pro Val Ser Ala Pro Thr Pro Gly Ser Gly Pro Leu Val Asn Gly
770                 775                 780

Ile Gln Ala Gly Lys Gly Lys Pro Pro Thr Pro Arg Met Gln Lys Arg
785                 790                 795                 800

Leu Lys Thr Gly Pro Gln Ala Gln Ser
                805

<210> SEQ ID NO 13
<211> LENGTH: 779
<212> TYPE: PRT
<213> ORGANISM: Botryotinia fuckeliana

<400> SEQUENCE: 13

Met Met Thr Ser Leu Gln Gln Gln His Ser Pro Tyr Pro Gly Leu Gln
1               5                   10                  15

His Gln Gly Val Pro Gln Gly His Met Ala Gly Met Pro His Ala Gln
                20                  25                  30

Gly Gln Gln Gly Gln Pro Gly Pro Gly Met Pro Gln Gln Met His Met
            35                  40                  45

Gly Val Ser Gly Pro Gly Pro Gln Val Thr Gln Ala Gly Ala Met
    50                  55                  60

Met Ala Gly Met Pro Pro Gly Ala Gly Pro Asn Ala His Ala Leu Gln
65                  70                  75                  80

His Leu Asn Pro Asn Gln Gln Ala Gln Ala Met Phe Gln Gln Gln Gln
                85                  90                  95

Gln Gln Gln Gln Gln Met Met Asn Ala Asn Pro Gln Leu Met His His
                100                 105                 110

Gln Met Leu Gln Gln Ala Ala Arg Gln Arg Gln Ile Gln Leu Gln
            115                 120                 125

Gln Gln Tyr Ser Gly Gly Gly Met Pro Asn Gly Met Pro Val Asn Met
130                 135                 140

His Gly Met Asn Pro Asn Gln Met Asn Ala Gln Phe Ala Met Arg His
145                 150                 155                 160

Gly Thr Pro Gly Met Ala Arg Pro Val Asn Leu Pro Gln His Leu Ala
                165                 170                 175

Gln Gln Gln Gln Met Ala Gln Asp Asn Val Asn Gln Gln Gln Ala His
            180                 185                 190

Gln Gln Thr Gln Gln Met Met Leu Ala Met His Gln Gln Asn Ala Gln
        195                 200                 205

Asn His Gly Pro Asn Gly Gln Ala Gly His Pro Gln Met Thr Pro Gln
    210                 215                 220

Gln Met Gln Gln Leu Gln Gln His Gln Leu Ala Gln Gln Gln Gln Gln
225                 230                 235                 240

Gln His Gln Gln Gln Gln Gln Gln Gln Gln Gln Gln Gln Gln Gln
                245                 250                 255

Gln Gln Gln Ala His Ala Gln Ala Gln Ala Val Gln Ala Gln Gln Ala
                260                 265                 270
```

-continued

Gln Ala Gln Ala Gln Ala Gln Ala Ala Ala Val Ser Gln
        275                 280             285

Gln Gln Asn Gln Asn Gln Ser Gln Ala Gln Asn Gln Pro Pro Gln Ser
    290             295             300

Ala Ser Thr Pro Gln Pro Gln Ala Pro Gln Pro Ala Ala Ile Gln Ala
305             310             315             320

Ala Ile Gln Ala Gln Ala Gln Ala Gln Gln Ala Gln Ala Gln Gln Ala
            325             330             335

Gln Ala Gln Gln Ala Gln Thr Gln Gln Pro Ser Gly Ala Leu Gln Gln
        340             345             350

Gln Gln Gln Gln Gln Gln Gln Gln His Ala Ala Ala Met Leu Gln Gln
    355             360             365

Gln Gln Gln Gln Gln Gln Gln Gln Gln Thr Arg Gln Gly Glu Lys
    370             375             380

Leu Lys Gly Gln Cys Leu Met Arg Leu Val Gln Phe Ser Asp His Leu
385             390             395             400

Gly Gly Phe Cys Lys Val Val Lys Pro Val Gly Phe Tyr Glu Ala Asn
            405             410             415

Gly Val Ser Arg Leu Asn Ala Glu Ser Met Lys Glu Lys Asp Asp Leu
        420             425             430

Ala Tyr Trp Gly Ser Phe Ala Glu Arg Phe Phe Ser Arg Gly Gly Val
        435             440             445

Leu Arg Tyr Ser Thr Tyr Ser Tyr Ser Pro Thr Glu Lys Ile Arg Glu
    450             455             460

Lys Gln Tyr Glu Ile Ala Ser Pro Ala Met Pro Arg Tyr Phe His Thr
465             470             475             480

His Phe Glu Ser Gly Val Thr Asn Met Gln Met Ile Phe Glu Lys Gly
            485             490             495

Thr Glu Lys Glu Leu Pro Leu Asn Gly His Tyr Ile Glu Ser Gln Asn
        500             505             510

Ser Ser Phe Val Tyr Trp Phe Glu Asp Gly Ser His Leu Val Ser Asn
    515             520             525

Gly Ile Leu Arg Ala His Phe Asp Gly Asp Gln Lys Leu Glu Leu Leu
    530             535             540

Asp Phe Glu Thr Arg Ser His Gln Glu Tyr Val Ser Arg Ser Met Ala
545             550             555             560

Ile Asp Arg Ala Arg Pro Ile His Asn Trp Val Lys Asp Trp Lys Ser
            565             570             575

Met Asn Asn Gly Pro Asp Gly Lys Pro Ser Pro Glu Met Asn Lys Lys
        580             585             590

Lys Gln Lys Met Met Lys Ser Pro Pro Asn Pro Pro Asp Phe Asp
    595             600             605

Leu Pro Glu Thr Lys Leu Thr Gln Tyr Thr Gly Ile Thr Pro Met Val
    610             615             620

Phe Arg Phe Leu Glu Met Asn Glu Val Leu Ala Gln Met Asn Pro Leu
625             630             635             640

Met Asn Tyr Leu Gln Ser Asn Pro Thr Leu Thr Pro Tyr Lys Ala Leu
            645             650             655

Asp Ala Tyr Met Ala Gln Val Ser Ser Asn Gly Ala Asn Gly Gly Pro
        660             665             670

Gln Asn Pro Ser Gly Pro Arg Thr Pro Ala Met Val Asn Phe Pro Ile
    675             680             685

Gly Ala Ser Pro Ala Ala Ala His Leu Gln Ile Pro Glu Gly Ser Pro

```
                690             695             700
His Met Met Gly Ser Pro Ala Gln Ala Pro Gly Met Gln Leu Gln Gln
705             710             715             720

Ser Gln His Gly Thr Thr Ser Ser Gly Pro Ser Ala Asn Thr Ser Pro
                725             730             735

Asn Ala Ser Asn Lys Arg Arg Arg Pro Ser Thr Val Lys Ala Glu Glu
                740             745             750

Asp Gly Gln Ala Asn Gly Thr Gly Lys Asn Asn Val Lys Pro Ser Pro
                755             760             765

Arg Ile Thr Lys Arg Gln Lys Gly Asn Pro Ala
                770             775

<210> SEQ ID NO 14
<211> LENGTH: 830
<212> TYPE: PRT
<213> ORGANISM: Sporotrichum thermophile

<400> SEQUENCE: 14

Met Met Ala Ser Met Gly Pro Gly Phe Ser Pro His Pro Ala Gly Met
1               5               10              15

Gln Gln His Pro Gly Ala Pro Pro Gly His Pro Met Ala Pro Ser Met
                20              25              30

Ala His Asn Pro Ser Gln Pro Gly Thr Thr Ala Gly Ala Met Pro His
                35              40              45

Gln Leu Val Gly His Met Ala Val Ser Gly Pro Gly Pro Gln Met Asn
    50              55              60

Ala Ala Thr Leu Met Gly Gly Met Pro Pro Gly Asn Pro Asn Ala His
65              70              75              80

Ala Ala Met Gln His Leu Asn Pro Ala Gln Val Gln Gln Met Phe His
                85              90              95

His Pro Gln Met Asn Gln Met Tyr Ala Ala Asn Ser Pro Ala Ala Gln
                100             105             110

Gln Met Gln Gln Gln Arg Leu Gln Ala Leu Gln Gln Gln Gln Gln Gln
                115             120             125

Ala Arg Ala Ala Leu Ile Ala Gln His Ala Val Tyr Gln Asn Leu Gly
    130             135             140

Ser Ala Gln Met Gly Val Pro Met Ser Gln Met Ser Pro Ala Gln Ala
145             150             155             160

Ala His Met Ala Ala Met Ser Arg Arg Met Pro Val Ala Pro Pro Phe
                165             170             175

His Leu Gln Gln Ala Gln Leu Ala Gln His Gln Gln Gly Gln Pro Met
                180             185             190

Asn Thr Asn Met Leu Ala Gln Gln Ile Ala Leu Gln Gln Gln Gln Arg
                195             200             205

Gln Gln Met Gln Met Gly Gln Gln Gly Gly Asn Pro Asn Gln His Gln
    210             215             220

Met Asn Pro Gln His Ile Asn Leu Gln Gln Ala Gln Ile Ala Ala Ile
225             230             235             240

Gln Ala Gln Gln Ala Gln His Ala Gln Gln Ala Gln Gln Ala Gln Gln
                245             250             255

Gln Gln Gln Gln Gln Gln Gln Gln Gln Gln His Gln Gln Gln Gln Gln
                260             265             270

Gln Gln Gln Gln Gln Gln Gln Gln His Gln Gln Gln Gln Gln Gln Gln
                275             280             285
```

```
Gln Gln Gln Gln Gln Gln Ala Gln Gln Ala Ala Gln Ala Ala
290                 295             300
Gln Ala Gln Gln Ala Gln Gln Gln Gly Gln Ala Gln Pro Gln Gln
305                 310             315                 320
Gln Gln Gln Gln Pro Gln Gln Pro Gln Gln Gln Gln Gln Pro Gln
                325             330                 335
Gln Pro Gln Gln Gln Pro Pro Gly Gln Pro Gln Gln Gln Gln
            340             345             350
Ser Gln Pro Gly Gln Pro Gly Pro Gly Ala Ser Thr Pro Ala Pro Thr
            355             360             365
Pro Gly Pro Pro Gly Gln Thr Pro Gln Pro Asn Pro Gln Gln Gln Pro
    370             375             380
Gln Val Pro Pro Gln Thr Pro Gln Thr Ser Gln Pro Gln His Gln Ala
385                 390             395                 400
Gln Leu Val Ala Gln Met Gln Ala Val Gln Gln Gln Gln His
                405             410                 415
Ala Ala Asn Met Ala Asn Leu Ala Gln Gln Arg Asn Leu Arg Gly
            420             425             430
Met Tyr Leu Leu Lys Leu Met Gln Phe Ser Glu His Leu Asn Gly Phe
    435             440             445
Pro Gly Ser Lys Gly Arg Asp Asp Leu Glu Tyr Trp His Asn Phe Val
    450             455             460
Arg Met Phe Phe Ser Pro Lys Gly Val Phe Lys His Ser Ile Leu Ile
465             470             475                 480
Arg Asp Gly Asp Gln Thr Gln Gln Lys His Tyr Glu Ile Ala Tyr
            485             490                 495
Pro Ala Ile Pro Arg Tyr Phe His Thr His Phe Asp Ser Gly Val Lys
            500             505             510
Ser Met Gln Leu Ile Met Asp Lys Gly Thr Ile Asp Arg Ile Met Pro
            515             520             525
Asn Asp Cys His Met Ile Trp Asn Asp Lys Thr Ser Leu Val Tyr Trp
            530             535             540
Phe Glu Asp Gly Ala His Leu Val Ala Thr Gly Thr Leu Arg Val His
545             550             555                 560
Phe Asp Ser Glu Gln Lys Phe Asp Ile Phe Glu Phe Thr Thr Gly
                565             570             575
His Glu Glu Tyr Val Ser Arg Arg Leu Val Ile Gln Ala Ala Arg Pro
            580             585             590
Ser His Asn Trp Val Lys Glu Trp Arg Asn Leu Asn Ala Gln Asp Pro
    595             600             605
Lys Gln Ser Pro Glu Met Ser Lys Lys Gly Lys Pro Lys Pro Ala Lys
    610             615             620
Ala Pro Pro Gly Pro Pro Asp Ile Glu Leu Pro His Ser Val Val
625             630             635                 640
Lys Ser Asn Met Gly Ile Thr Glu Ala Val Tyr Gln Phe Leu Glu Met
                645             650             655
Val Glu Ile Met Gly Gln Met Gly Pro Leu Phe Gly Tyr Tyr His Ala
            660             665             670
His Pro Gly Leu Ala Pro Tyr Ala Leu Asp Gln Tyr Leu Asn Gln
            675             680             685
Ile Asn Ala Ser Ala Gln Ala Gln Ser Met Asn Gly Gln Pro Met Ser
690             695             700
Gln Gly Gly Pro Arg Thr Pro Gly Phe Gly Gln Phe Gln Gly Val Gly
```

```
                    705                 710                 715                 720
Ala Ser Pro Ala Met Ala Asn Ala Met Leu Pro Gly Ser Pro His Val
                725                 730                 735

Ser Gly Ser Pro Ala Pro Ala Gln Met Ser Ala Pro Met Met Gln Leu
            740                 745                 750

Gln Ala Ser Gln Gln Gly Thr Ser Ser Gly Pro Ser Ala Asn Thr
        755                 760                 765

Ser Pro Ala Gln Asn Ser Asn Lys Arg Arg Pro Ser Thr Val Lys
    770                 775                 780

Ala Glu Glu Asp Thr Pro Ala Ser Ala Pro Thr Pro Gly Gln Val Gly
785                 790                 795                 800

Thr Pro Gln Leu Asn Gly Val Gln Ile Lys Gly Gly Lys Pro Pro Thr
                805                 810                 815

Pro Arg Met Pro Lys Arg His Lys Thr Gly Asn Asn Pro Val
                820                 825                 830

<210> SEQ ID NO 15
<211> LENGTH: 25
<212> TYPE: DNA
<213> ORGANISM: artificial sequence
<220> FEATURE:
<223> OTHER INFORMATION: primer

<400> SEQUENCE: 15
gaacctcccg gggtcgcctc acatc                                             25

<210> SEQ ID NO 16
<211> LENGTH: 24
<212> TYPE: DNA
<213> ORGANISM: artificial sequence
<220> FEATURE:
<223> OTHER INFORMATION: primer

<400> SEQUENCE: 16
gctgcaacga acgtcctttg catc                                              24

<210> SEQ ID NO 17
<211> LENGTH: 46
<212> TYPE: DNA
<213> ORGANISM: artificial sequence
<220> FEATURE:
<223> OTHER INFORMATION: primer

<400> SEQUENCE: 17
tgaagccgat gtcacacgcg tgaacctccc ggggtcgcct cacatc                      46

<210> SEQ ID NO 18
<211> LENGTH: 45
<212> TYPE: DNA
<213> ORGANISM: artificial sequence
<220> FEATURE:
<223> OTHER INFORMATION: primer

<400> SEQUENCE: 18
acgcagctag cagctggtac cgctgcaacg aacgtccttt gcatc                       45

<210> SEQ ID NO 19
<211> LENGTH: 20
<212> TYPE: DNA
<213> ORGANISM: artificial sequence
<220> FEATURE:
<223> OTHER INFORMATION: primer
```

```
<400> SEQUENCE: 19
ctctcgatga tgcgtgtaag                                               20

<210> SEQ ID NO 20
<211> LENGTH: 20
<212> TYPE: DNA
<213> ORGANISM: artificial sequence
<220> FEATURE:
<223> OTHER INFORMATION: primer

<400> SEQUENCE: 20
ccatactcgt agccatcatc                                               20

<210> SEQ ID NO 21
<211> LENGTH: 41
<212> TYPE: DNA
<213> ORGANISM: artificial sequence
<220> FEATURE:
<223> OTHER INFORMATION: primer

<400> SEQUENCE: 21
gtactgagag tgcaccatat gctctcgatg atgcgtgtaa g                       41

<210> SEQ ID NO 22
<211> LENGTH: 41
<212> TYPE: DNA
<213> ORGANISM: artificial sequence
<220> FEATURE:
<223> OTHER INFORMATION: primer

<400> SEQUENCE: 22
tcggttctta attaagaatt cccatactcg tagccatcat c                       41

<210> SEQ ID NO 23
<211> LENGTH: 20
<212> TYPE: DNA
<213> ORGANISM: artificial sequence
<220> FEATURE:
<223> OTHER INFORMATION: primer

<400> SEQUENCE: 23
gatgatggct acgagtatgg                                               20

<210> SEQ ID NO 24
<211> LENGTH: 20
<212> TYPE: DNA
<213> ORGANISM: artificial sequence
<220> FEATURE:
<223> OTHER INFORMATION: primer

<400> SEQUENCE: 24
gggaatcgag caagtaagag                                               20

<210> SEQ ID NO 25
<211> LENGTH: 27
<212> TYPE: DNA
<213> ORGANISM: artificial sequence
<220> FEATURE:
<223> OTHER INFORMATION: primer

<400> SEQUENCE: 25
ttgctagcat gggacatcct ggagttg                                       27

<210> SEQ ID NO 26
<211> LENGTH: 31
```

```
<212> TYPE: DNA
<213> ORGANISM: artificial sequence
<220> FEATURE:
<223> OTHER INFORMATION: primer

<400> SEQUENCE: 26
ttggtacctc aggccgggtt gcccttcatt c                                31

<210> SEQ ID NO 27
<211> LENGTH: 799
<212> TYPE: PRT
<213> ORGANISM: Penicillium chrysogenum

<400> SEQUENCE: 27
```

| Met | Met | Met | Thr | Gln | Pro | Phe | Pro | Ala | His | Gln | Gly | Met | Pro | Gln | His |
|---|---|---|---|---|---|---|---|---|---|---|---|---|---|---|---|
| 1 | | | | 5 | | | | | 10 | | | | | 15 | |

| Gly | Phe | Pro | Pro | Gly | His | Pro | Met | Ala | Ala | Gln | His | Pro | Asn | Gly | His |
|---|---|---|---|---|---|---|---|---|---|---|---|---|---|---|---|
| | | | 20 | | | | | 25 | | | | | 30 | | |

| Pro | Gly | Ala | Gly | Met | Val | Gln | Gln | Met | His | Pro | Gly | Val | Ser | Ala | Pro |
|---|---|---|---|---|---|---|---|---|---|---|---|---|---|---|---|
| | | 35 | | | | | 40 | | | | | 45 | | | |

| Gly | Gly | Pro | Gln | Val | Ser | Gln | Pro | Gly | Pro | Met | Met | Gly | Gly | Met | Pro |
|---|---|---|---|---|---|---|---|---|---|---|---|---|---|---|---|
| | 50 | | | | | 55 | | | | | 60 | | | | |

| Pro | Gly | Ala | Gly | Thr | Ala | Gly | Pro | Gly | Gly | Pro | Gly | Pro | Asn | Ala | His |
|---|---|---|---|---|---|---|---|---|---|---|---|---|---|---|---|
| 65 | | | | | 70 | | | | | 75 | | | | | 80 |

| Ala | Leu | Ser | His | Leu | Asn | Pro | Ala | Gln | Ala | His | Met | Leu | Gln | Asn | Pro |
|---|---|---|---|---|---|---|---|---|---|---|---|---|---|---|---|
| | | | | 85 | | | | | 90 | | | | | 95 | |

| Gln | Phe | Pro | Gln | Asn | Phe | Ala | Asn | Asn | Pro | His | Leu | Leu | His | Gln | Gln |
|---|---|---|---|---|---|---|---|---|---|---|---|---|---|---|---|
| | | | 100 | | | | | 105 | | | | | 110 | | |

| Gln | His | Gln | Gln | Gln | Leu | Met | Arg | Gln | Arg | Met | Met | Leu | Gln | His | Gln |
|---|---|---|---|---|---|---|---|---|---|---|---|---|---|---|---|
| | | 115 | | | | | 120 | | | | | 125 | | | |

| Gln | His | Gln | His | Gln | Gln | Gln | Gln | Gln | Gln | Gln | Gln | Gln | Gln | Gln | Gln |
|---|---|---|---|---|---|---|---|---|---|---|---|---|---|---|---|
| | 130 | | | | | 135 | | | | | 140 | | | | |

| Gln | Gln | Gln | Gln | Gly | Leu | Pro | Val | Ser | Met | Pro | Asn | Gly | Thr | Gln | Gly |
|---|---|---|---|---|---|---|---|---|---|---|---|---|---|---|---|
| 145 | | | | | 150 | | | | | 155 | | | | | 160 |

| Leu | Asn | Ala | Ala | Gln | Met | Ala | Ala | Met | Gln | Ala | Asn | Pro | Gly | Met | Arg |
|---|---|---|---|---|---|---|---|---|---|---|---|---|---|---|---|
| | | | | 165 | | | | | 170 | | | | | 175 | |

| Pro | Val | Asn | Met | Met | His | Leu | Gln | Gln | Gln | Met | Pro | His | Gly | Gln | Pro |
|---|---|---|---|---|---|---|---|---|---|---|---|---|---|---|---|
| | | | 180 | | | | | 185 | | | | | 190 | | |

| Pro | Ser | Leu | Gln | Gln | Gln | Gln | Gln | Phe | Phe | Ala | Ile | Gln | Gln | Ala | Gln |
|---|---|---|---|---|---|---|---|---|---|---|---|---|---|---|---|
| | | 195 | | | | | 200 | | | | | 205 | | | |

| Gln | Ala | Gln | His | Ala | Gln | Gln | Gln | Ala | Asn | Asn | Gly | Gln | Ser | Gly | Gln |
|---|---|---|---|---|---|---|---|---|---|---|---|---|---|---|---|
| | 210 | | | | | 215 | | | | | 220 | | | | |

| His | Thr | Pro | Gln | Arg | Thr | Ser | Ala | Gln | Pro | Pro | Asn | Met | His | Glu | Gln |
|---|---|---|---|---|---|---|---|---|---|---|---|---|---|---|---|
| 225 | | | | | 230 | | | | | 235 | | | | | 240 |

| Ser | Ala | Thr | Pro | Gln | Ser | Gln | His | Gly | Gly | Pro | Gly | Gly | Gly | Thr | Pro |
|---|---|---|---|---|---|---|---|---|---|---|---|---|---|---|---|
| | | | | 245 | | | | | 250 | | | | | 255 | |

| Gln | Pro | Ser | Gln | Thr | Ser | Gln | Pro | Pro | Ser | Thr | Gln | Pro | Pro | Gln | Ser |
|---|---|---|---|---|---|---|---|---|---|---|---|---|---|---|---|
| | | | 260 | | | | | 265 | | | | | 270 | | |

| Gln | Gly | Pro | Pro | Gln | Gly | Gln | Pro | Thr | Pro | Asn | Pro | Pro | Gln | Gln | Gln |
|---|---|---|---|---|---|---|---|---|---|---|---|---|---|---|---|
| | | 275 | | | | | 280 | | | | | 285 | | | |

| Leu | Pro | Gln | Ser | Gln | Gln | Pro | Gly | Gln | Gly | Gln | Ala | Gly | Pro | Gln |
|---|---|---|---|---|---|---|---|---|---|---|---|---|---|---|
| | 290 | | | | | 295 | | | | | 300 | | | |

| Pro | Gln | Pro | Pro | Gln | Ser | Ala | Gln | Gly | Gln | Gln | Pro | Gly | Pro | Gln | Asn |
|---|---|---|---|---|---|---|---|---|---|---|---|---|---|---|---|
| 305 | | | | | 310 | | | | | 315 | | | | | 320 |

| Gln | Gln | Met | Thr | Ala | Gln | Glu | Ala | Gln | Leu | Lys | Ala | Gln | Gln | His | Gln |
|---|---|---|---|---|---|---|---|---|---|---|---|---|---|---|---|
| | | | | 325 | | | | | 330 | | | | | 335 | |

```
Asn Ala Leu Met Met Gln Gln Gln Gln Gln Gln Arg Lys Asn Asn
            340                 345                 350

Ala Ile Leu Thr Ile His Ala Tyr Ala Glu His Leu Gly Asn Phe Gln
        355                 360                 365

Ser Arg Asn Glu Ala Gln Asp Leu Leu Tyr Trp Gln Ser Phe Val Asp
370                 375                 380

Arg Phe Tyr Ser Pro Val Gly Val Leu Arg Gln Gly Val Trp Asn Ser
385                 390                 395                 400

Thr Ile Gly Ser Lys Gln Phe Glu Ile Ala Thr Pro Ala Leu Ala Arg
                405                 410                 415

Tyr Tyr Leu Thr Gln Phe Thr Ser Gly Ile Ser His Ile Gln Met Val
            420                 425                 430

Val Glu Gly Ala Arg Glu Arg Glu Ser Gln Asn Gly Gly His Tyr Val
            435                 440                 445

Glu Ala Pro Lys Cys Ser Phe Ile Tyr Trp Phe Lys Asn Glu Cys Gln
        450                 455                 460

Leu Phe Thr Asn Gly Thr Leu Arg Ala His Phe Asp Met His Asn Lys
465                 470                 475                 480

Leu Glu Met Leu Asp Ile Asn Val Ile Ser His Asn Glu Phe Ile Pro
                485                 490                 495

Arg Ser Leu Leu Leu Ala Met Glu Ala Asp Ser Gln Lys Gln Ser Pro
            500                 505                 510

Lys Val Ala Lys Asn Ser Lys Arg Ala Leu Pro Lys Gln Ala Pro Ser
            515                 520                 525

Leu Val Pro Asp Ser Asn Val Thr Ala Asn Gly Val Pro Thr Pro Val
        530                 535                 540

Met Gly Phe Met Glu Val Ala Glu Thr Ile Ser Ala Met Gln Met Leu
545                 550                 555                 560

Phe Gln Phe Ser Gln Ala Asn Pro Gln Leu Ser Pro Pro Asp Ala Leu
                565                 570                 575

Arg Asn Leu Val Asn Thr Leu Gln Ser Gln Asn Pro Asn Pro Gly Phe
            580                 585                 590

Val Pro Pro Met Pro Met Asn Gln Gly Met Asn Pro Ala Met Asn Pro
        595                 600                 605

Gly Met Asn Pro Gly Met Asn Gln Gly Met Asn Pro Gly Met Ser Pro
        610                 615                 620

Gly Met Ser Pro Ser Met Asn Pro Gly Met Asn Pro Gly Met Asn Gln
625                 630                 635                 640

Gly Met Asn Pro Gly Met Asn Pro Ala Met Gln Pro Gly Met Ser Pro
                645                 650                 655

Gly Met Asn Pro Ala Met His Pro Gly Met Asn Pro Gly Met Asn Pro
            660                 665                 670

Gly Met Asn Pro Gly Met Gln Pro Met Gln Asn Val Arg Gly His Ser
            675                 680                 685

Met Gly Ala Pro Ser Gln Phe Ala Ser Pro Ala Met Ala His Leu Gly
        690                 695                 700

Leu Pro Gly Gln Gln Gly Ser Pro His Leu Thr Gly Ser Ala His Ala
705                 710                 715                 720

Ser Pro Ala Gln Ser Asn Leu Ala Gly Pro Gly Met Gln Pro Pro
                725                 730                 735

Met Gln Pro Ser Pro Ala Gly Val Asn Asn Ser Pro Asn Val Gly Gly
            740                 745                 750
```

-continued

```
Asn Lys Arg Arg Arg Ala Ser Thr Val Lys Met Glu Ser Glu Asp Gly
        755                 760             765

Gly Gly Val Glu Ala Asn Gly Ala Pro Gln Gln Gly Ser Gly Lys Val
    770             775             780

Lys Ala Ser Pro Arg Val Pro Lys Arg Gln Lys Gly Ala Ala Ala
785             790             795
```